(12) United States Patent
Besidski et al.

(10) Patent No.: US 7,645,784 B2
(45) Date of Patent: Jan. 12, 2010

(54) BENZIMIDAZOLE DERIVATIVES

(75) Inventors: Yevgeni Besidski, Sodertalje (SE); Inger Kers, Sodertalje (SE); Martin Nylöf, Sodertalje (SE); Didier Rotticci, Sodertalje (SE); Andis Slaitas, Sodertalje (SE); Mats Svensson, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 149 days.

(21) Appl. No.: 10/556,229

(22) PCT Filed: May 13, 2004

(86) PCT No.: PCT/SE2004/000738

§ 371 (c)(1),
(2), (4) Date: Nov. 9, 2005

(87) PCT Pub. No.: WO2004/100865

PCT Pub. Date: Nov. 25, 2004

(65) Prior Publication Data

US 2006/0287377 A1    Dec. 21, 2006

(30) Foreign Application Priority Data

May 16, 2003   (SE) .................... 0301446
Jan. 12, 2004   (SE) .................... 0400043

(51) Int. Cl.
A61K 31/4184  (2006.01)
C07D 235/04   (2006.01)

(52) U.S. Cl. ................. 514/394; 548/301.7; 548/302.7; 548/304.4; 548/309.7; 514/385; 514/393

(58) Field of Classification Search ............. 548/300.1, 548/301.7, 302.7, 304.4, 309.7; 514/385, 514/393, 394

See application file for complete search history.

(56) References Cited

U.S. PATENT DOCUMENTS

| | | | |
|---|---|---|---|
| 3,624,103 A | 11/1971 | Franco De Martiis | |
| 3,839,347 A | 10/1974 | Fisher et al. | |
| 4,722,929 A | 2/1988 | Austel et al. | |
| 4,738,981 A | 4/1988 | Horwell | |
| 6,794,404 B2 | 9/2004 | Beaulieu et al. | |
| 7,030,139 B2 | 4/2006 | Cheng et al. | |
| 7,501,447 B2 | 3/2009 | Liu | |
| 2003/0149050 A1 | 8/2003 | Jagtap et al. | |
| 2003/0158188 A1 | 8/2003 | Lee et al. | |
| 2004/0092569 A1 | 5/2004 | Demaine et al. | |
| 2004/0152690 A1 | 8/2004 | Balan et al. | |
| 2004/0248983 A1 | 12/2004 | Morie et al. | |
| 2006/0135554 A1 | 6/2006 | Cheng et al. | |
| 2006/0205802 A1 | 9/2006 | Liu et al. | |
| 2007/0066586 A1 | 3/2007 | Tokumasu et al. | |
| 2008/0015222 A1 | 1/2008 | Besidski et al. | |
| 2008/0171770 A1 | 7/2008 | Besidski | |
| 2008/0221188 A1 | 9/2008 | Brown et al. | |
| 2009/0111865 A1 | 4/2009 | Liu et al. | |

FOREIGN PATENT DOCUMENTS

| | | |
|---|---|---|
| DE | 2300521 | 7/1973 |
| EP | 0 149 200 | 12/1984 |
| EP | 149200 | 7/1985 |
| EP | 0 419 210 A1 | 3/1991 |
| EP | 1 312 601 A1 | 5/2003 |
| EP | 0882718 B1 | 8/2005 |
| GB | 1186504 | 4/1970 |
| WO | WO 94/22859 | 10/1994 |
| WO | WO 99/00115 | 1/1999 |
| WO | WO 01/12189 A1 | 2/2001 |
| WO | WO 01/85722 A1 | 11/2001 |
| WO | WO 01/96336 A2 | 12/2001 |
| WO | WO 02/50031 A1 | 6/2002 |
| WO | WO 02/072536 A1 | 9/2002 |
| WO | 02085866 A1 | 10/2002 |
| WO | WO 02/090326 A1 | 11/2002 |
| WO | 02/100819 A1 | 12/2002 |
| WO | WO 02/100822 A1 | 12/2002 |
| WO | WO 03/014064 A1 | 2/2003 |
| WO | WO 03/022809 A2 | 3/2003 |
| WO | 03027076 A2 | 4/2003 |
| WO | WO 03/049702 | 6/2003 |
| WO | WO 03/053945 A2 | 7/2003 |
| WO | WO 03/068749 A1 | 8/2003 |
| WO | WO 04/000828 A1 | 12/2003 |

(Continued)

OTHER PUBLICATIONS

McDonnell, et al., "7-Hydroxynaphthalen-1-yl-Urea and -Amide Antagonists of Human Vanilloid Receptor 1"; Bioorganic & Medicinal Chemistry Letters 14 (2004), pp. 531-534.

(Continued)

*Primary Examiner*—Golam M M Shameem
(74) *Attorney, Agent, or Firm*—Karen Kondrad

(57) ABSTRACT

Compounds of formula I,

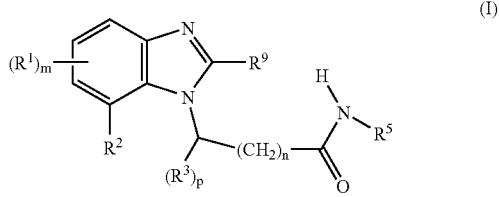

(I)

wherein $R^1$, m, $R^2$, $R^3$, p, n, $R^5$ and $R^9$ are as defined as in the specification, salts, solvates or solvated salts thereof, processes for their preparation, intermediates used in the preparation thereof, pharmaceutical formulations containing said compounds and the use of said compounds in therapy.

9 Claims, No Drawings

FOREIGN PATENT DOCUMENTS

| | | | |
|---|---|---|---|
| WO | WO 2004/024154 A1 | 3/2004 | |
| WO | WO 2004/024710 | 3/2004 | |
| WO | 2004108712 A1 | 12/2004 | |
| WO | 2005021539 A1 | 3/2005 | |
| WO | 2005095327 A1 | 10/2005 | |
| WO | 2006/007851 | 1/2006 | |
| WO | 2006033620 A1 | 3/2006 | |
| WO | 2007073303 A2 | 6/2007 | |
| WO | 2008/018827 A1 | 6/2008 | |

OTHER PUBLICATIONS

Musso, et al., "Indanylidenes. 1. Design and Synthesis of . . . and Analgesic Activity"; J. Med. Chem 2003, 46, pp. 399-408.

Yiangou, et al., "Capsaicin Receptor VR1 and ATP-Gated ion Channel P2X3, in Human Urinary Bladder"; BJU International (2001), 87, pp. 774-779.

Walker, et al., "The VR1 Antagonist Capsazepine . . . Inflammatory and Neuropathic Pain"; J. Pharmacology & Experimental Therapeutics, vol. 304, No. 1, pp. 56-62.

Rashid, et al., "Novel Expression of Vanilloid . . . in Neuropathic Pain"; J. Pharmacology & Experimental Therapeutics, vol. 304, No. 3, pp. 940-948.

Caterina, et al., "The Capsaicin Receptor: A Heat-Activated Ion Channel in the Pain Pathway"; Nature, vol. 389, Oct. 23, 1997, pp. 816-824.

Tominaga, et al., "The Cloned Capsaicin Receptor Integrates Multiple Pain-Producing Stimuli"; Neuron, vol. 21, Sep. 1998, pp. 531-543.

Hwang, et al., "Hot Channels in Airways: Pharmacology of the Vanilloid Receptor"; Respiratory, Curr Opin Pharmacol 2002, June, 2(3) pp. 235-242.

Szallasi, et al. "Vanilloid (Capsaicin) Receptors in Health and Disease"; Am J Clin Pathol 2002, 118, pp. 110-121.

T.L. Gilchrist, "Heterocyclic Chemistry", 2nd Edition, Longman Scientific and Technical (1992), pp. 248-282.

B. Bijaya Kumar, V. Malla Reddy, Indian Journal of Chemistry, vol. 24B, Oct. 1985, pp. 1098-1101, Table 1, Scheme I.

Anthony Gallard, et al., Journal of Enzyme Inhibition and Medicinal Chemistry, vol. 18, No. 2. 2003, "New N-Pyridinyl(methyl)-N1-Substituted . . . Systemic anti-Inflammatory Agents", pp. 201-208.

STN International, Accession No. 200:912544, Apr. 24, 2003, CHS 00297096, 1H-Benzimidazole-1-acetamide, N-[3-(trifluoromethyl)phenyl]-CAS Registry No. 294669-15-1.

STN International, Accession No. 2000:532079, Apr. 23, 2003, BAS 0238979, 1H-Benzimidazole-1-acetamide, N-(3-chlorophenyl)-CAS Registry No. 116488-26-7.

STN International, Accession No. 2001:10738, Apr. 24, 2003, NS11937, 1H-Indole-3-butananmide, N-(4-methylphenyl)-CAS Registry No. 313550-48-0.

STN International, Accession No. 2001:1505160, Apr. 29, 2003, AG-690/40696518, 1H-Benzimidazole-1-acetamide,N-(2,3-dichlorophenyl)-, CAS Registry No. 332384-60-8.

STN International, Accession No. 2002:2035573, Jul. 9, 2002, ASN 1816063, "1H-Benzimidazole-1-acetamide,N-(3-chloro-4-methylphenyl)" -CAS Registry No. 332908-87-9.

STN International, Accession No. 2002:2042451, Jul. 9, 2002, ASN 4428244, "1H-Benzimidazole-1-acetamide,N-(5-amino-2-methylphenyl)"—CAS registry No. 436095-70-4.

STN International, Accession No. 2003:454497, Apr. 30, 2003, ASN 5212034, "1H-Indole-3-acetamide, N-[4-(1-methylethyl)phenyl]"—CAS Registry No. 460336-68-9.

STN International, Accession No. 2003:454500, Apr. 30, 2003, ASN 5212038, 1H-Indole-3-acetamide, N-(3,5-dimethoxyphenyl)—CAS Registry No. 460336-71-4.

STN International, Accession No. 2003:1778448, Jul. 9, 2002, ASN 3067491, "1H-Benzimidazole-1-acetamide, N-(2-flurophenyl)"—CAS Registry No. 483326-88-1.

STN International, Accession No. 2003:1780032, Jul. 9, 2002, ASN 3110045, "1H-Benzimidazole-1-acetamide, 5,6-dimethyl-N-[2-(trifluoromethyl)phenyl]"—CAS Registry No. 483347-09-7.

STN International, Accession No. 2003:1780036, Jul. 9, 2002, ASN 3110053, "1H-Benzimidazole-1-acetamide,N-(2,4-dimethoxyphenyl)-5,6-dimethyl"—CAS Registry No. 483347-12-2.

STN International, Accession No. 2003:1780041, Jul. 9, 2002, ASN 3110088, 1H-Benzimidazole-1-acetamide, "N-[4-(dimethylamino)phenyl]-5,6-dimethyl"—CAS Registry No. 483347-17-7.

STN International, Accession No. 2003:1783073, Jul. 9, 2002, ASN 3212475, "1H-Benzimidazole-1-acetamide, N-(3-fluorophenyl)"—CAS Registry No. 483978-05-8.

STN International, Accession No. 2003:2842871, Apr. 30, 2003, BAS 5595011, "1H-Indole-3-acetamide, N-(3-fluoro-4-methylphenyl)"—CAS Registry No. 510764-85-9.

STN International, Accession No. 2003:3562090, Apr. 30, 2003, ZT-5586656, "1H-Indole-3-propanamide,N-[2-(1-methylethyl)phenyl]"—CAS Registry No. 556791-23-2.

STN International, Accession No. 2003:3425665, Apr. 30, 2003, ZT-2132403, "1H-Indole-3-propanamide, N-[4-(1,1-dimethylethyl)phenyl]"—CAS Registry No. 562052-38-4.

STN International, Accession No. 2003:3428083, Apr. 30, 2003, ZT-2150185, "1H-Indole-3-propanamide, N-(2-chloro-4-methylphenyl)"—CAS Registry No. 562794-00-7.

STN International, Accession No. 2002:737351, document No. 138:265138, Olgen, Sureyya, et al., "Synthesis and . . . indole-3-acetamide derivatives", & Archiv der Pharmzie (Weinheim, Germany) (2002), 335(7), 331-338.

STN International, Accession No. 2002:695939, document n o. 137:232452, Rotta Research Lab, S.p.A., "Preparation of benzamidines having antiinflammatory & immunosuppressive activity", & WO2002070468,A2,20020912.

STN International, Accession No. 2000:825244, document No. 134:147129, Jamieson, Craig, et al., "A rapid approach for the optimization of polymer supported reagents in synthesis", & Synlett (2000), (11), 1603-1607.

STN International, Accession No. 1988:610992, document No. 109:210992, Shah, V.H., et al., "Studies on acetamide derivatives. Part-II. Preparation . . . sulfamethazin-4-yl/acetamides", & Jr of the Indian Chemical Society (1987), 64(11), 678-81.

STN International, Accession No. 1958:31856, document n o. 52:31856, Cacace, Fulvio, et al., "Benzimidazole-N-acetic . . . growth activity", & Atti accad. nazl. Lincei. Rend., Classe sci. fiz., mat. e nat. (1957), 22, 510-13.

STN International, Accession No. 1993:102385, document No. 118:102385, Gallant, Michel, et al., "A stereoselective synthesis . . . of rebeccamycin", & Jr of Organic Chemistry (1993), 58(2), 343-9.

STN International, Accession No. 1998:227318, document No. 128:308402, Sanwa Kagaku Kenkyusho Co., Ltd., "Preparation of . . . as antiarteriosclerotics", & JP, A2, 10095766, 19980414.

STN International, Accession No. 1995:594439, document No. 123:9266, Interneuron Pharm, Inc., "Substituted tryptamines . . . and related compounds", & US,A,5403851,19950404.

International Search Report for International Application No. PCT/SE2004/000738.

International-Type Search Report.

Beilstein Institute for Organic Chemistry, Frankfurt-Main, Germany; XP002291482, BRN 838602 abstract and Kamel et al, J. Prakt. Chem., vol. 31, 1966, pp. 100-105.

Beilstein Institute for Organic Chemistry, Frankfurt-Main, Germany; XP002291483 BRN 926470 abstract and Osman: Kolor. ERT., vol. 11, 1969, p. 118.

Beilstein Institute for Organic Chemistry, Frankfurt-Main, Germany; XP002291484 BRN 311062 abstract & Pinnow; Wiskott: Chem. Ber., vol. 32, 1899, p. 900.

Beilstein Institute for Organic Chemistry, Frankfurt-Main, Germany; XP002291485 BRN 189489 abstract & Foster: J. Chem. Soc., 1957, pp. 4687-8.

Beilstein Institute for Organic Chemistry, Frankfurt-Main, Germany; XP002291490 BRN 326965 abstract & V. Walter; Kessler: J. Prak. Chem., vol. 2, No. 74, 1906, p. 198.

Collins et al., "Mucosal Tolerance to a Bacterial Superantigen Indicates a Novel AJ Toxic Shock", Infection and Immunity 70:2282-2287 (2002).

Lindberg, et al., "Long-Time Persistence of Superantigen-Producing Staphylococcus Aureus Strains in the Intestinal Microflora of Healthy Infants", Pediatric Research 48:741-747 (2000).

Patent Abstracts of Japan vol. 2000, No. 07, Sep. 29, 2000 (Sep. 29, 2000) & JP 2000 095767 A (Takeda Chem Ind Ltd), Apr. 4, 2000.

Rudin, et al., "Staphylococcal Enterotoxin B and High Dose Phytohemagglutinin Induce a Th1- Skewed Response in Neonates Irrespective of Atopic Status at 2 Years of Age", Scandinavian Journal of Immunology 52:415-461 (2000).

Sasaki, et al., "Prevention of collagen-induced arthritis with the superantigen Staphylococcal enterotoxin B", Pathophysiology 4:25-31 (1997).

Soos, et al., "Treatment PL/J mice with the superantingen, staphylococcal enterotoxin B, prevents development of experimental allergic encephalomyelitis", J Neuroimmunology 43:39-44 (1993).

Willitzer, H. et al., "Synthese und antivirale Wirsamkeit von substituierten 5-Ureido- und 5- Thioureidobenzimidazolderivaten" Pharmazie, VEB VERLAG VOLK und Gesundheit. Berlin, Germeny vol. 33, No. 1, Jan. 1978 (1078-01), pp. 30-38, XP002209435 ISSN: 0031-7144 English Abstract is cited as access No. 1978:424221.

STN International, File CAPLUS, accession No. 1978:424221, document No. 89:24221, Willitzer et al., "Synthesis and antiviral activity of substituted 5-ureido- and 5-thioureidobenzimidazole derivatives", & Pharmazie (1978), 33(1) 30-8.

STN International File Caplus, accession No. 1958:50566, document No. 52:50566, R. Foster, "1-Ethyl-2-methyl-5-nitrobenzimidazole", & Journal of the Chem. Society, Abstracts (1957) 4687-8.

STN International, File HCAPLUS, accession No. 2000:214835, document No. 132:265201, Takeda Chemical Industries Ltd., "Preparation of imidazole derivatives as gonadotropin-releasing hormone antagonists", & JP, A2,200095767, 20000404.

STN International File CAPLUS accession No. 1967:46373, document No. 66:46373, Takahashi, S. et al., "Benzimidazole N-oxides. VII. Reactivity of 1,2-dimethylbenzimidazole 3-oxide" & Chem & Pharm Bulletin (1966), 14 (11), 1219-27.

STN International, File CAPLUS, accession No. 1969:492626, doc No. 71:92626, Osman, M.A. "Benzimidazole derivatives as azoic diazo and coupling components", & Kolorisztikai Ertesito (1969) 11(5-6), 118-21.

STN Intl. CAPLUS, accession No. 1966:51996, document No. 64:51996, Kamel, M. et al., "New indazole and benzimidazole derivatives", Journal fuer Praktische Chemie (1966), 31(102), 100-8.

STN Intl. File Registry (Chemcats), compounds with Reg. Nos. 499119-26-5, 498538-36-6, 498535-73-2, 497242-15-6, 494202-99-2, 488804-38-2, 488095-08-5, 476326-10-0, 476325-77-6, 476281-13-7, 476279-49-9, 476275-91-9, 391218-48-7, 380905-60-2, 377757-95-4, 364625-75-2, 364054-61-5, 335397-26-7, 335397-24-5, 332899-59-9, 331840-20-1, 330466-04-1, 327971-85-7, 318512-58-2, 313535-67-0, 313509-05-6, 313508-99-5, 313367-31-6, 313275-92-2, 313275-91-1, 313275-90-0, 313275-89-7, 313275-88-6, 313275-87-5, 313241-54-2, 313241-53-1.

STN International, File Registry, see RN 743444-08-08, Sep. 13, 2004.

Non-final Office Action mailed on May 16, 2008, for U.S. Appl. No. 10/557,806, AstraZeneca reference No. 101101-1P US.

Co-pending U.S. Appl. No. 11/836,221, filed on Aug. 9, 2007.

Co-pending U.S. Appl. No. 11/614,346, filed on Dec. 21, 2006.

Co-pending U.S. Publication No. 2008-0015222, published on Jan. 17, 2008.

Co-pending U.S. Publication No. 2006-0205802, published on Sep. 14, 2006.

Non-final Office Action mailed on Jul. 23, 2008 for U.S. Appl. No. 10/557,806, AstraZeneca reference No. 101101-1P US.

STN International, File CAPLUS, Acession No. 2000:21922, Document No. 132:222537, "Preparation of Substituted Nitrogen-Containing Heterocyclic Compounds" Hovrath, A. et al. HU78019.

BENZIMIDAZOLE DERIVATIVES

FIELD OF THE INVENTION

The present invention relates to new compounds, to pharmaceutical formulations containing said compounds and to the use of said compounds in therapy. The present invention further relates to processes for the preparation of said compounds and to the use of intermediates in the preparation thereof.

BACKGROUND OF THE INVENTION

Pain sensation in mammals is due to the activation of the peripheral terminals of a specialized population of sensory neurons known as nociceptors. Capsaicin, the active ingredient in hot peppers, produces sustained activation of nociceptors and also produces a dose-dependent pain sensation in humans. Cloning of the vanilloid receptor 1 (VR1 or TRPV1) demonstrated that VR1 is the molecular target for capsaicin and its analogues. (Caterina, M. J., Schumacher, M. A., et.al. Nature (1997) v.389 p 816-824). Functional studies using VR1 indicate that it is also activated by noxious heat, tissue acidification) and other inflammatory mediators (Tominaga, M., Caterina, M. J. et. al. Neuron (1998) v.21, p. 531-543). Expression of VR1 is also regulated after peripheral nerve damage of the type that leads to neuropathic pain. These properties of VR1 make it a highly relevant target for pain and for diseases involving inflammation. While agonists of the VR1 receptor can act as analgesics through nociceptor destruction, the use of agonists, such as capsaicin and its analogues, is limited due to their pungency, neurotoxicity and induction of hypothermia. Instead, agents that block the activity of VR1 should prove more useful. Antagonists would maintain the analgesic properties, but avoid pungency and neurotoxicity side effects. Compounds with VR1 inhibitor activity are believed to be of potential use for the treatment and/or prophylaxis of disorders such as pain, especially that of inflammatory or traumatic origin such as arthritis, ischaemia, cancer, fibromyalgia, low back pain and post-operative pain (Walker et al J Pharmacol Exp Ther. (2003) January; 304(1):56-62). In addition to this visceral pains such as chronic pelvic pain, cystitis, irritable bowel syndrome (IBS), pancreatitis and the like, as well as neuropathic pain such as sciatia, diabetic neuropathy, HIV neuropathy, multiple sclerosis, and the like (Walker et al ibid, Rashid et al J Pharmacol Exp Ther. (2003) March; 304(3):940-8), are potential pain states that could be treated with VR1 inhibiton. These compounds are also believed to be potentially useful for inflammatory disorders like asthma, cough, inflammatory bowel disease (IBD) (Hwang and Oh Curr Opin Pharmacol (2002) June; 2(3):235-42). Compounds with VR1 blocker activity are also useful for itch and skin diseases like psoriasis and for gastro-esophageal reflux disease (GERD), emesis, cancer, urinary incontinence and hyperactive bladder (Yiangou et al BJU Int (2001) June; 87(9):774-9, Szallasi Am J Clin Pathol (2002) 118: 110-21). VR1 inhibitors are also of potential use for the treatment and/or prophylaxis of the effects of exposure to VR1 activators like capsaicin or tear gas, acids or heat (Szallasi ibid).

A further portential use relates to the treatment of tolerance to VR1 activators. VR1 inhibitors may also be useful in the treatment of interstitial cystitis and pain related to interstitial cystitis.

DETAILED DESCRIPTION OF THE INVENTION

The object of the present invention is to provide compounds exhibiting an inhibitory activity at the vanilloid receptor 1 (VR 1). Especially, derivatives substituted at the C-7 atom of the benzoimidazole ring show a significant increase in efficacy.

The present invention provides compounds of formula I

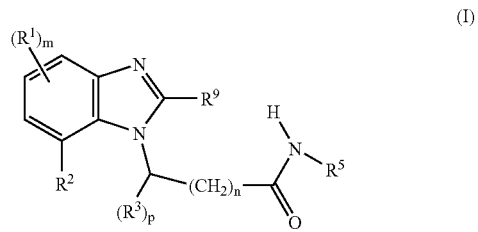

wherein:
$R^1$ is H, $NO_2$, halo, $NR^6R^7$, $C_{1-6}$alkyl, $C_{2-6}$alkenyl, $C_{2-6}$alkynyl, $C_{1-6}$haloalkyl,
$C_{1-6}$haloalkylO, $R^6OC_{0-6}$alkyl, $R^6CO$, $R^6OCO$ or $CONR^6R^7$;
m is 0, 1, 2 or 3;
$R^2$ is $NO_2$, halo, $NR^6R^7$, $C_{1-6}$alkyl, $C_{2-6}$alkenyl, $C_{2-6}$alkynyl, $C_{1-6}$haloalkyl,
$C_{1-6}$haloalkylO, cyano, $R^6OC_{0-6}$alkyl, $R^6CO$, $R^6OCO$, $R^6CONR^7$, $R^6R^7NCO$, $R^8SO_2$, $R^8SO_2HN$, aryl$C_{0-6}$alkyl or heteroaryl$C_{0-6}$alkyl;
$R^3$ and $R^9$ are each independently H or $C_{1-4}$alkyl;
p is 0, 1 or 2;
n is 0, 2, 3 or 4;
$R^5$ is $C_{1-10}$alkyl, $C_{6-10}$aryl$C_{0-6}$alkyl, $C_{3-7}$cycloalkyl$C_{0-6}$alkyl or $C_{5-6}$heteroaryl$C_{0-6}$alkyl, whereby any aryl, heteroaryl or cycloalkyl may be fused with aryl, heteroaryl, $C_{3-7}$cycloalkyl or $C_{3-7}$heterocycloalkyl, and which $R^5$ may be substituted with one or more A;
A is H, OH, $NO_2$, cyano, $R^6CO$, $R^6O(CO)$, halo, $C_{1-6}$alkyl, $NR^6R^7$, $C_{1-6}$haloalkyl,
$C_{1-6}$haloalkylO, $R^6OC_{0-6}$alkyl, hydroxy$C_{1-6}$alkyl, $R^8SO_2$, $R^8SO_2HN$, $C_{5-6}$arylO or $CONR^6R^7$;
$R^6$ and $R^7$ are each independently H or $C_{1-6}$alkyl; and
$R^8$ is $NR^6R^7$ or $C_{1-4}$alkyl, or salts, solvates or solvated salts thereof.

One embodiment of the invention relates to compounds of formula I wherein:
$R^1$ is H, halo, $NR^6R^7$, $C_{1-6}$alkyl, $C_{1-6}$haloalkyl, $C_{1-6}$haloalkylO, $R^6OC_{0-6}$alkyl, $R^6CO$, $R^6OCO$ or $CONR^6R^7$;
m is 0 or 1;
$R^2$ is $NO_2$, halo, $NR^6R^7$, $C_{1-6}$alkyl, $C_{1-6}$haloalkyl, cyano, $R^6OCO$, $R^6CONR^7$, $R^8SO_2$,
$R^8SO_2HN$ or heteroaryl$C_{0-6}$alkyl;
$R^3$ and $R^9$ are each independently H or $C_{1-4}$alkyl;
p is 0;
n is 0;
$R^5$ is $C_{1-10}$alkyl, $C_{6-10}$aryl$C_{0-6}$alkyl or $C_{5-6}$heteroaryl$C_{0-6}$alkyl, whereby any aryl may be fused with $C_{3-7}$cycloalkyl or $C_{3-7}$heterocycloalkyl, and which $R^5$ may be substituted with one or more A;

A is H, cyano, halo, $NO_2$, $C_{1-6}$alkyl, $NR^6R^7$, $C_{1-6}$haloalkyl, $C_{1-6}$haloalkylO, $R^6OC_{0-6}$alkyl, hydroxy$C_{1-6}$alkyl, $R^8SO_2$ or $C_{5-6}$arylO;

$R^6$ and $R^7$ are each independently H or $C_{1-6}$alkyl; and $R^8$ is $NR^6R^7$ or $C_{1-4}$alkyl, or salts, solvates or solvated salts thereof.

In another embodiment of the invention the benzoimidazole is substituted with 0, 1, 2 or 3 groups $R^1$, wherein the number of $R^1$ substituents is designated by the term m. In another embodiment of the invention m is 0 or 1.

In a further embodiment of the invention $R^1$ is hydrogen or halo.

In yet another embodiment $R^1$ is hydrogen. In a further embodiment $R^1$ is fluoro.

$R^2$ may be selected from the group comprising $NO_2$, halo, $NR^6R^7$, $C_{1-4}$alkyl, $C_{1-4}$haloalkyl, $C_{1-2}$haloalkylO, cyano, $R^6OC_{0-4}$alkyl, $R^6CO$, $R^6OCO$, $R^6CONR^7$, $R^6R^7NCO$, $R^8SO_2$, $R^8SO_2HN$, aryl$C_{0-6}$alkyl and heteroaryl and wherein $R^6$ and $R^7$ are each independently H or $C_{1-4}$alkyl and $R^8$ is $NR^6R^7$ or $C_{1-3}$alkyl.

In one embodiment of the invention $R^2$ is nitro.

In another embodiment $R^2$ is halo, which halo may be fluoro, bromo or chloro.

In yet another embodiment of the invention $R^2$ is $C_{1-3}$haloalkyl. In one embodiment $R^2$ is fluoroalkyl, whereby the alkyl may be substituted with 1 to 6 fluoro atoms.

In another embodiment $R^2$ is selected from the group containing fluoromethyl, difluoromethyl, trifluoromethyl, fluoroethyl, difluoroethyl, trifluoroethyl, tetrafluoroethyl and pentafluoroethyl.

In a further embodiment $R^2$ is $C_{1-4}$alkyl. In one embodiment $R^2$ is selected from the group consisting methyl, ethyl, propyl and isopropyl. In another embodiment $R^2$ is methyl. In yet another embodiment $R^2$ is a carboxylic acid alkyl ester. In another embodiment $R^2$ is carboxylic acid methyl ester.

In yet a further embodiment $R^2$ is a sulfonyl group. In one embodiment $R^2$ is an alkylsulfonyl, (alkyl)aminosulfonyl, (dialkyl)aminosulfonyl or an alkylsulfonylamino.

In another embodiment $R^2$ is methylsulfonyl, ethylsulfonyl or propylsulfonyl.

In a further embodiment $R^2$ is methyl-aminosulfonyl, (dimethyl)-aminosulfonyl, (diethyl)-aminosulfonyl or (methyl, ethyl)-aminosulfonyl.

In yet another embodiment $R^2$ is methylsulfonylamino.

In one embodiment $R^2$ is amino, alkylamino or dialkylamino. In another embodiment $R^2$ is methylamino, ethylamino, propylamino or isopropylamino. In a further embodiment $R^2$ is dimethylamino or diethylamino.

In yet another embodiment $R^2$ is a carboxamide. In one embodiment $R^2$ is acetylamino. In a further embodiment $R^2$ is cyano.

In one embodiment $R^2$ is a heteroaryl. In another embodiment $R^2$ is tetrazolyl.

One embodiment of the invention relates to compounds of formula I wherein $R^3$ and $R^9$ are H and p is 0 and n is 0.

In another embodiment $R^3$ is methyl or ethyl. In a further embodiment $R^3$ is methyl.

In one embodiment of the invention $R^5$ is $C_{1-6}$alkyl. In another embodiment $R^5$ is selected is from the group consisting methyl, ethyl, propyl, butyl, pentyl and hexyl. In a further embodiment $R^5$ is hexyl.

In yet another embodiment of the invention $R^5$ is $C_{6-10}$aryl$C_{0-4}$alkyl, which may be substituted with one or more A.

In one embodiment of the invention $R^5$ is phenyl$C_{0-4}$alkyl, which may be substituted by one or more A. In another embodiment $R^5$ is phenylmethyl or phenylethyl and A is selected from the group consisting halo, $C_{1-2}$haloalkyl, $C_{1-4}$alkyl and $C_{1-4}$alkoxy.

One embodiment of the invention relates to compounds of formula I wherein $R^5$ is $C_{6-10}$aryl fused with $C_{3-7}$cycloalkyl or $C_{3-7}$heterocycloalkyl, which may be substituted with one or more A.

In another embodiment $R^5$ is phenyl fused with a $C_{5-6}$heterocycloalkyl, which heterocycle contains one or more heteroatoms selected form N and O. In yet another embodiment $R^5$ is phenyl fused with dioxane.

In yet a further embodiment $R^5$ is phenyl fused with $C_{5-6}$cycloalkyl. In another embodiment $R^5$ indanyl.

One embodiment of the invention relates to compounds of formula I wherein $R^5$ is phenyl, which may be substituted with one or more A.

In one embodiment $R^5$ is phenyl.

In another embodiment $R^5$ is phenyl substituted with one or more A.

In a further embodiment $R^5$ is phenyl substituted with one or more A, which A is selected from the group comprising halo, alkoxy, haloalkoxy, haloalkyl, alkyl, alkanol, cyano, phenoxy, alkylsulfonyl and (di)alkylamino.

In another embodiment $R^5$ is substitituted by 1, 2, 3 or 4 A. In one embodiment $R^5$ is substituted by 1 or 2 A. In another embodiment A is substituted by 3 A.

In one embodiment A is selected from the group consisting fluoro, iodo, chloro, bromo, methoxy, ethoxy, trifluoromethyl, difluoromethoxy, trifluoromethoxy, tetrafluoroethoxy, methyl, ethyl, propyl, butyl, hydroxyethyl, cyano, phenoxymethylsulfonyl and dimethylamino.

A further embodiment of the invention relates to compounds selected from the group consisting N-(3-Fluoro-4-methoxy-phenyl)-2-(7-nitro-1H-benzimidazol-1-yl)-acetamide, N-[2-Fluoro-4-(trifluoromethyl)phenyl]-2-(7-nitro-1H-benzimidazol-1-yl)acetamide, N-(3-Chloro-4-iodophenyl)-2-(7-nitro-1H-benzimidazol-1-yl)acetamide, N-(3-Chloro-4-methoxyphenyl)-2-(7-nitro-1H-benzimidazol-1-yl)acetamide, N-[3-(Difluoromethoxy)phenyl]-2-(7-nitro-1H-benzimidazol-1-yl)acetamide, N-[3-Methoxy-5-(trifluoromethyl)phenyl]-2-(7-nitro-1H-benzimidazol-1-yl)acetamide, N-(3,5-Difluorophenyl)-2-(7-nitro-1H-benzimidazol-1-yl)acetamide, 2-(7-Nitro-1H-benzimidazol-1-yl)-N-[4-(trifluoromethoxy)phenyl]acetamide, 2-(7-Nitro-1H-benzimidazol-1-yl)-N-[3-(1,1,2,2-tetrafluoroethoxy)phenyl]acetamide, N-(4-tert-Butylphenyl)-2-(7-nitro-1H-benzimidazol-1-yl)acetamide, N-[3-(1-Hydroxyethyl)phenyl]-2-(7-nitro-1H-benzimidazol-1-yl)acetamide, 2-(7-Nitro-1H-benzimidazol-1-yl)-N-[4-(trifluoromethyl)phenyl]acetamide, N-(3-Chlorophenyl)-2-(7-nitro-1H-benzimidazol-1-yl)acetamide, N-Hexyl-2-(7-nitro-1H-benzimidazol-1-yl)acetamide, N-(3,4-Difluorophenyl)-2-(7-nitro-1H-benzimidazol-1-yl)acetamide, N-(4-Cyanophenyl)-2-(7-nitro-1H-benzimidazol-1-yl)acetamide, N-(2,3-Dihydro-1,4-benzodioxin-6-yl)-2-(7-nitro-1H-benzimidazol-1-yl)acetamide,
N-(2-Bromobenzyl)-2-(7-nitro-1H-benzimidazol-1-yl)acetamide,
2-(7-Nitro-1H-benzimidazol-1-yl)-N-[3-(trifluoromethyl)benzyl]acetamide,
N-(4-Methylpyridin-2-yl)-2-(7-nitro-1H-benzimidazol-1-yl)acetamide,
N-(3-Cyanophenyl)-2-(7-nitro-1H-benzimidazol-1-yl)acetamide,
N-(3,5-Dimethoxyphenyl)-2-(7-nitro-1H-benzimidazol-1-yl)acetamide,
N-(4-Methoxyphenyl)-2-(7-nitro-1H-benzimidazol-1-yl)acetamide,
N-(3-Ethoxyphenyl)-2-(7-nitro-1H-benzimidazol-1-yl)acetamide,
N-(3,4-Dimethoxyphenyl)-2-(7-nitro-1H-benzimidazol-1-yl)acetamide,
2-(7-Nitro-1H-benzimidazol-1-yl)-N-(3,4,5-trimethoxyphenyl)acetamide,
2-(7-Nitro-1H-benzimidazol-1-yl)-N-[3-(trifluoromethoxy)phenyl]acetamide,
2-(7-Nitro-1H-benzimidazol-1-yl)-N-(3-phenoxyphenyl)acetamide,
N-(4-Butylphenyl)-2-(7-nitro-1H-benzimidazol-1-yl)acetamide,
N-(2-Fluoro4-iodophenyl)-2-(7-nitro-1H-benzimidazol-1-yl)acetamide,
2-(7-Nitro-1H-benzimidazol-1-yl)-N-[2-(trifluoromethoxy)phenyl]acetamide,
N-(4-Methoxyphenyl)-2-(7-nitro-1H-benzimidazol-1-yl)acetamide,
2-(7-Nitro-1H-benzimidazol-1-yl)-N-(2-phenoxyphenyl)acetamide,
N-(4-Bromo-2-fluorophenyl)-2-(7-nitro-1H-benzimidazol-1-yl)acetamide,
N-[3-(Methylsulfonyl)phenyl]-2-(7-nitro-1H-benzimidazol-1-yl)acetamide,
N-[4-(Methylsulfonyl)phenyl]-2-(7-nitro-1H-benzimidazol-1-yl)acetamide,
2-(7-Nitro-1H-benzimidazol-1-yl)-N-[4-(trifluoromethyl)benzyl]acetamide,
N-(4-tert-Butylbenzyl)-2-(7-nitro-1H-benzimidazol-1-yl)acetamide,
N-(2,3-dihydro-1H-inden-5-yl)-2-(7-nitro-1H-benzimidazol-1-yl)acetamide,
2-(7-Nitro-1H-benzimidazol-1-yl)-N-[4-(trifluoromethoxy)benzyl]acetamide,
N-(4-Isopropylphenyl)-2-(7-nitro-1H-benzimidazol-1-yl)acetamide,
N-(3,4-Dimethylphenyl)-2-(7-nitro-1H-benzimidazol-1-yl)acetamide,
N-1,3-Benzodioxol-5-yl-2-(7-nitro-1H-benzimidazol-1-yl)acetamide,
N-[3-Bromo4-(trifluoromethoxy)phenyl]-2-(7-nitro-1H-benzimidazol-1-yl)acetamide,
N-(3-Fluoro-2-methoxyphenyl)-2-(7-nitro-1H-benzimidazol-1-yl)acetamide,
N-(3,5-dimethoxyphenyl)-2-(7-nitro-1H-benzimidazol-1-yl)propanamide,
N-(3-Ethoxyphenyl)-2-(7-nitro-1H-benzimidazol-1-yl)propanamide,
2-(7-Nitro-1H-benzimidazol-1-yl)-N-[3-(trifluoromethyl)phenyl]propanamide,
N-(3,5-Dimethylphenyl)-2-(7-nitro-1H-benzimidazol-1-yl)acetamide,
2-(7-Nitro-1H-benzimidazol-1-yl)-N-[3-(trifluoromethyl)phenyl]acetamide,
2-(7-Bromo-1H-benzimidazol-1-yl)-N-(3,5-dimethoxyphenyl)acetamide,
2-(7-Bromo-1H-benzimidazol-1-yl)-N-(3-methoxyphenyl)acetamide,
2-(7-Bromo-1H-benzimidazol-1-yl)-N-[3-(trifluoromethyl)phenyl]acetamide,
2-(7-Chloro-1H-benzimidazol-1-yl)-N-(3,5-dimethoxyphenyl)acetamide,
2-(7-Chloro-1H-benzimidazol-1-yl)-N-[3-(trifluoromethyl)phenyl]acetamide,
2-(7-Chloro-1H-benzimidazol-1-yl)-N-(4-methylphenyl)acetamide,
2-(7-Chloro-1H-benzimidazol-1-yl)-N-(2,3-dihydro-1H-inden-5-yl)acetamide,
2-(7-Methyl-1H-benzimidazol-1-yl)-N-(4-methylphenyl)acetamide,
N-(3,5-Dimethoxyphenyl)-2-(7-methyl-1H-benzimidazol-1-yl)acetamide,
2-(7-Methyl-1H-benzimidazol-1-yl)-N-[3-(trifluoromethyl)phenyl]acetamide,
N-(2,3-Dihydro-1H-inden-5-yl)-2-(7-methyl-1H-benzimidazol-1-yl)acetamide,
Methyl 1-{2-[(3,4-dimethylphenyl)amino]-2-oxoethyl}-1H-benzimidazole-7-carboxylate,
Methyl 1-[2-(2,3-dihydro-1H-inden-5-ylamino)-2-oxoethyl]-1H-benzimidazole-7-carboxylate,
Methyl 1-{2-[(4-tert-butylbenzyl)amino]-2-oxoethyl}-1H-benzimidazole-7-carboxylate,
Methyl 1-(2-{[3-methoxy-5-(trifluoromethyl)phenyl]amino}-2-oxoethyl)-1H-benzimidazole-7-carboxylate,
Methyl 1-{2-[(3,5-dimethoxyphenyl)amino]-2-oxoethyl}-1H-benzimidazole-7-carboxylate,
N-(3,5-Dimethoxyphenyl)-2-{7-[(dimethylamino)sulfonyl]-1H-benzimidazol-1-yl}acetamide,
2-{7-[(Dimethylamino)sulfonyl]-1H-benzimidazol-1-yl}-N-[3-(trifluoromethyl)phenyl]acetamide,
N-(3,5-Dimethoxyphenyl)-2-[7-(propylsulfonyl)-1H-benzimidazol-1-yl]acetamide,
2-[7-(Propylsulfonyl)-1H-benzimidazol-1-yl]-N-[3-(trifluoromethyl)phenyl]acetamide,
N-[3-Methoxy-5-(trifluoromethyl)phenyl]-2-[7-(methylsulfonyl)-1H-benzimidazol-1-yl]acetamide,
N-(3,5-Dimethoxyphenyl)-2-[7-(trifluoromethyl)-1H-benzimidazol-1-yl]acetamide,
N-(3,4-Dimethylphenyl)-2-[7-(trifluoromethyl)-1H-benzimidazol-1-yl]acetamide,
N-(4-tert-Butylbenzyl)-2-[7-(trifluoromethyl)-1H-benzimidazol-1-yl]acetamide,
N-(2,3-Dihydro-1H-inden-5-yl)-2-[7-(trifluoromethyl)-1H-benzimidazol-1-yl]acetamide,
2-(7-Cyano-1H-benzimidazol-1-yl)-N-(3,5-dimethoxyphenyl)acetamide,
2-(7-Cyano-1H-benzimidazol-1-yl)-N-(3-methoxyphenyl)acetamide,
2-(7-Cyano-1H-benzimidazol-1-yl)-N-[3-(trifluoromethyl)phenyl]acetamide,
2-(7-Cyano-1H-benzimidazol-1-yl)-N-(2,3-dihydro-1H-inden-5-yl)acetamide,
N-(2,3-Dihydro-1H-inden-5-yl)-2-(7-fluoro-1H-benzimidazol-1-yl)acetamide,
N-(3,5-Dimethoxyphenyl)-2-(7-fluoro-1H-benzimidazol-1-yl)acetamide,
N-(4-tert-Butylbenzyl)-2-(7-fluoro-1H-benzimidazol-1-yl)acetamide, 2-(7-Amino-1H-benzoimidazol-1-yl)-N-[3-(trifluoromethyl)phenyl]acetamide,
2-[7-(Acetylamino)-1H-benzoimidazol-1-yl]-N-[3-(trifluoromethyl)phenyl]acetamide,
2{(7-[(Methylsulfonyl)amino]-1H-benzoimidazol-1-yl }-N-[3-(trifluoromethyl)phenyl]acetamide,
2-[7-(Dimethylamino)-1H-benzoimidazol-1-yl]-N-[3-(trifluoromethyl)phenyl]acetamide,
2-[7-(Isopropylamino)-1H-benzoimidazol-1-yl]-N-[3-(trifluoromethyl)phenyl]acetamide,
N-(3,5-Dimethoxyphenyl)-2-[7-(1H-tetrazol-5-yl)-1H-benzimidazol-1-yl]acetamide, and
2-(6,7-Difluoro-1H-benzimidazol-1-yl)-N-[3-(trifluoromethyl)phenyl]acetamide, or salts, solvates or solvated salts thereof.

One embodiment of the invention relates to compounds selected from the group consisting 2-(1H-Benzimidazol-1-yl)-N-[3-(trifluoromethyl)phenyl]propanamide,
2-(1H-Benzimidazol-1-yl)-N-(3-chloro-4-fluorophenyl)acetamide,
2-(1H-Benzimidazol-1-yl)-N-(3-fluoro-4-methylphenyl)acetamide,
2-(1H-Benzimidazol-1-yl)-N-(3,4-difluorophenyl)acetamide,
2-(4-Methyl-1H-benzimidazol-1-yl)-N-[3-(trifluoromethyl)phenyl]acetamide,
2-(4,5-Difluoro-1H-benzimidazol-1-yl)-N-[3-(trifluoromethyl)phenyl]acetamide,
2-(1H-Benzimidazol-1-yl)-N-[3-(dimethylamino)phenyl]acetamide,
2-(1H-Benzimidazol-1-yl)-N-(4-tert-butylphenyl)acetamide,
2-(1H-Benzimidazol-1-yl)-N-[3-(trifluoromethyl)benzyl]acetamide,
2-(1H-Benzimidazol-1-yl)-N-(4-chlorobenzyl)acetamide,
2-(1H-Benzimidazol-1-yl)-N-(3,5-dimethoxyphenyl)acetamide,
3-(1H-Benzimidazol-1-yl)-N-(4-tert-butylphenyl)propanamide,
4-(1H-Benzimidazol-1-yl)-N-(4-tert-butylphenyl)butanamide,
2-(1H-Benzimidazol-1-yl)-N-(2-methyl-1,3-benzothiazol-5-yl)acetamide,
2-(1H-Benzimidazol-1-yl)-N-[3-(trifluoromethyl)phenyl]acetamide,
2-(4-Amino-1H-benzimidazol-1-yl)-N-[3-(trifluoromethyl)phenyl]acetamide,
2-(5-Fluoro-1H-benzimidazol-1-yl)-N-[3-(trifluoromethyl)phenyl]acetamide,
2-(6-Fluoro-1H-benzimidazol-1-yl)-N-[3-(trifluoromethyl)phenyl]acetamide,
2-(4-Nitro-1H-benzimidazol-1-yl)-N-[3-(trifluoromethyl)phenyl]acetamide, and
2-( 1H-Benzimidazol-1-yl)-N-heptylacetamide, or salts, solvates or solvated salts thereof.

Another embodiment of the invention relates to compounds selected from the group consisting.
2-(1H-Indol-1-yl)-N-[3-(trifluoromethyl)phenyl]acetamide,
2-(5-Fluoro-1H-indol-3-yl)-N-[3-(trifluoromethyl)phenyl]acetamide, and
2-(1-Methyl-1H-indol-3-yl)-N-[3-(trifluoromethyl)phenyl]acetamide, or salts, solvates or solvated salts thereof.

Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl. The term $C_{1-3}$ alkyl having 1 to 3 carbon atoms and may be methyl, ethyl, n-propyl, i-propyl or tert-butyl.

The term '$C_0$' means a bond or does not excist. For example when $R^3$ is Coalkyl, $R^3$ is a bond and "arylCoalkyl" is equivalent with "aryl", "$C_2$alkylO$C_0$alkyl" is equivalent with "$C_2$alkylO".

In this specification, unless stated otherwise, the term "alkenyl" includes both straight and branched chain alkenyl groups. The term "$C_{2-6}$alkenyl" having 2 to 6 carbon atoms and one or two double bonds, may be, but is not limited to vinyl, allyl, propenyl, butenyl, crotyl, pentenyl, or hexenyl, and a butenyl group may for example be buten-2-yl, buten-3-yl or buten4-yl.

In this specification, unless stated otherwise, the term "alkynyl" includes both straight and branched chain alkynyl groups. The term "$C_{2-6}$alkynyl" having 2 to 6 carbon atoms and one or two trippel bonds, may be, but is not limited to etynyl, propargyl, pentynyl or hexynyl and a butynyl group may for example be butyn-3-yl or butyn4-yl.

In this specification, unless stated otherwise, the term "cycloalkyl" refers to an optionally substituted, saturated cyclic hydrocarbon ring system. The term "$C_{3-7}$cycloalkyl" may be cyclopropyl, cyclobutyl, cyclopentyl, cyclohexyl or cycloheptyl.

The term "heterocycloalkyl" denotes a 3- to 7-membered, non-aromatic, partially or completely saturated hydrocarbon group, which contains one ring and at least one heteroatom. Examples of said heterocycle include, but are not limited to pyrrolidinyl, pyrrolidonyl, piperidinyl, piperazinyl, morpholinyl, oxazolyl, 2-oxazolidonyl or tetrahydrofuranyl.

In this specification, unless stated otherwise, the term "aryl" refers to an optionally substituted monocyclic or bicyclic hydrocarbon unsaturated aromatic ring system. Examples of "aryl" may be, but are not limited to phenyl and naphthyl.

In this specification, unless stated otherwise, the term "heteroaryl" refers to an optionally substituted monocyclic or bicyclic unsaturated aromatic ring system containing at least one heteroatom selected independently form N, O or S. Examples of "heteroaryl" may be, but are not limited to pyridyl, pyrrolyl, furyl, thienyl, imidazolyl, oxazolyl, isoxazolyl, thiazolyl, pyrazolyl, benzofuryl, indolyl, isoindolyl, benzimidazolyl, pyridazinyl, pyrimidinyl, pyrazinyl, tetrazolyl, triazolyl or oxazolyl.

In this specification, unless stated otherwise, the terms "arylalkyl" and "heteroarylalkyl" refer to a substituent that is attached via the alkyl group to an aryl or heteroaryl group. In this specification, unless stated otherwise, the terms "halo" and "halogen" may be fluoro, iodo, chloro or bromo.

In this specification, unless stated otherwise, the term "haloalkyl" means an alkyl group as defined above, which is substituted with halo as defined above. The term "$C_{1-6}$haloalkyl" may include, but is not limited to fluoromethyl, difluoromethyl, trifluoromethyl, fluoroethyl, difluoroethyl or bromopropyl. The term "$C_{1-6}$haloalkylO" may include, but is not limited to fluoromethoxy, difluoromethoxy, trifluoromethoxy, fluoroethoxy or difluoroethoxy.

The present invention relates to the compounds of formula I as hereinbefore defined as well as to the salts, solvates or solvated salts thereof. Salts for use in pharmaceutical formulations will be pharmaceutically acceptable salts, but other salts may be useful in the production of the compounds of formula I.

A suitable pharmaceutically acceptable salt of the compounds of the invention is, for example, an acid-addition salt, for example a salt with an inorganic or organic acid. In addition, a suitable pharmaceutically acceptable salt of the compounds of the invention is an alkali metal salt, an alkaline earth metal salt or a salt with an organic base. Other pharmaceutically acceptable salts and methods of preparing these salts may be found in, for example, Remington's Pharmaceutical Sciences (18$^{th}$ Edition, Mack Publishing Co.).

Some compounds of formula I may have chiral centres and/or geometric isomeric centres (E- and Z-isomers), and it is to be understood that the invention encompasses all such optical, diastereoisomeric and geometric isomers.

The invention also relates to any and all tautomeric forms of the compounds of formula I.

Methods of Preparation

Another aspect of the present invention provides processes for preparing compounds of formula I, or salts, solvates or solvated salts thereof.

Throughout the following description of such processes it is to be understood that, where appropriate, suitable protecting groups will be added to, and subsequently removed from, the various reactants and intermediates in a manner that will be readily understood by one:, skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). References and descriptions of other suitable reactions are described in textbooks of organic chemistry, for example, "Advanced Organic Chemistry", March, 4$^{th}$ ed. McGraw Hill (1992) or, "Organic Synthesis", Smith, McGraw Hill, (1994). For representative examples of heterocyclic chemistry see for example "Heterocyclic Chemistry", J. A. Joule, K. Mills, G. F. Smith, 3$^{rd}$ ed. Chapman and Hall (1995), p. 189-224 and "Heterocyclic Chemistry", T. L. Gilchrist, 2$^{nd}$ ed. Longinan Scientific and Technical (1992), p. 248-282.

The term "room temperature" and "ambient temperature" shall mean, unless otherwise specified, a temperature between 16 and 25° C.

Methods of Preparation

One embodiment of the invention relates to processes for the preparation of the compound of formula I according to Methods A and B, wherein $R^1$ to $R^9$, unless otherwise specified, are defined as in formula I, comprising;

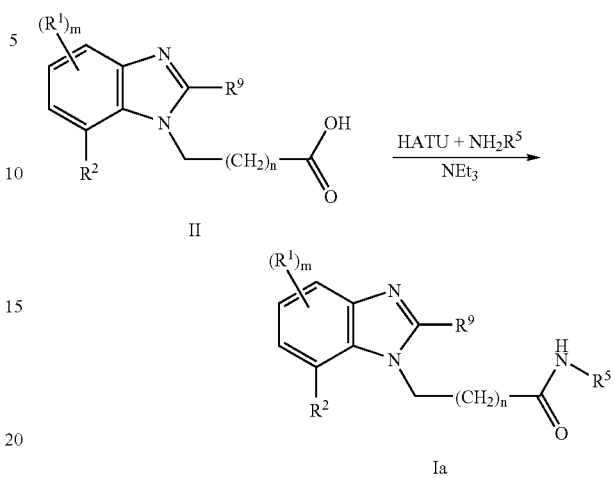

whereby the target compound of formula I is obtained from the acid of formula II or its deprotonated form, via its conversion into an activated form, i.e. either the acyl chloride by treatment with oxalyl chloride or the mixed anhydride by treatment with O-(7-azabenzotriazol1-yl)-N,N,N',N'-tetramethyluronium hexafluorophosphate and further treatment with an appropriate amine $NH_2R^5$. This reaction may be performed in any manner known to the skilled man in the art. The activation may be performed using any other similar activating reagent like 1,3-dicyclohexylcarbodiimide, 1-ethyl-3-(3-dimethylaminopropyl)carbodiimide hydrochloride or 1,1'-carbonyldiimidazole. Suitable solvents to be used for this reaction may be halogenated hydrocarbons such as chloroform, dichloromethane and dichloroethane or aromatic and heteroaromatic compounds such as benzene, toluene, xylene, pyridine and lutidine or ethers such as ethyl ether, tetrahydrofuran and dioxan or aprotic polar solvents like acetonitrile and dimethylformamide, or any mixtures thereof. Catalysts such as heteroaromatic bases like pyridine and lutidine or tertiary amines like triethylamine, N-methylmorpholine and ethyl diisopropylamine may be used as well. The temperature may be between −30 and 50° C. and the reaction time between 1 and 30 h.

Starting materials, the acids of formula II, may be obtained using multistep procedures described in detail in the following examples of synthesis starting from commercially available appropriately 1,2,3-trisubstituted benzenes. Or, Method B whereby the target compound of formula I is obtained from another compound of formula I by a chemical modification of the $R^2$ substituent using standard methods described in the literature, for example:

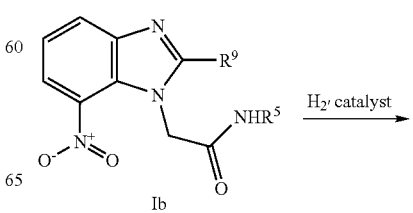

-continued
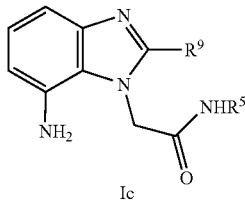
Ic
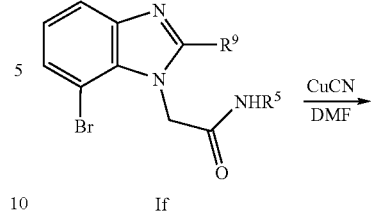
If
→ CuCN / DMF
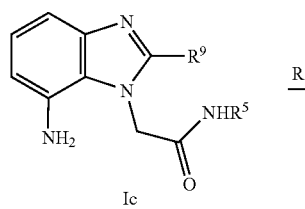
Ic
→ R⁶COCl or R⁶SO₂Cl
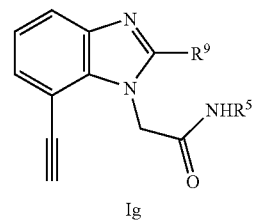
Ig
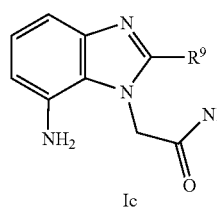
Id
R⁹ = COR⁶ or SO₂R⁶
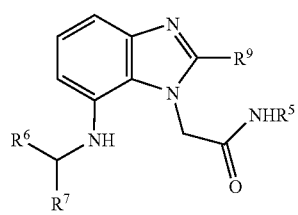
Ig
→ NaN₃/ZnBr₂
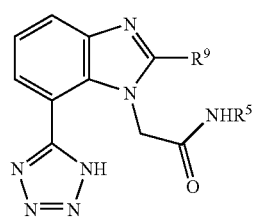
Ic
→ R⁶CHO or R⁶COR⁷ / NaCNBH₃
Ie
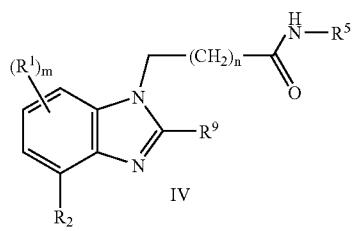
Ih
Method C
IV

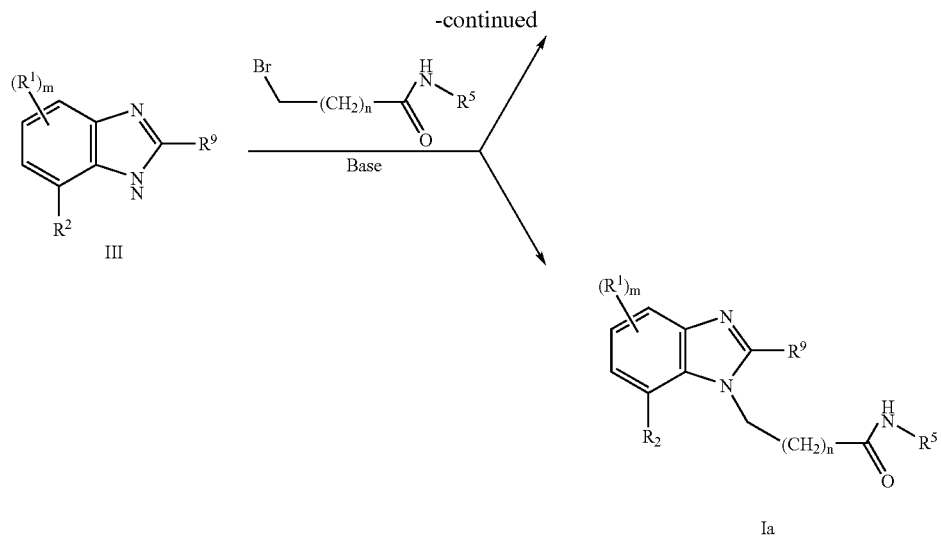

wherein, the target compound of formula I is obtained from an amidoalkylbromide and an appropriately substituted benzimidazole. Generally, this method yields a mixture of two regio-isomers, which can be separated by use of chromatography. Suitable solvents to be used for this reaction may be tertiary amides such as dimethylformnamide or dimethylacetamide or aromatic compounds such as benzene, toluene and xylene, or ethers such as ethyl ether, tetrahydrofuran and dioxan or alcohols such as methanol, ethanol and propanol, or any mixtures thereof. Bases such as potassium tert-butoxide, sodium methoxide and sodium hydride or tertiary amines like triethylamine, N-methylmorpholine and ethyl diisopropylamine may be used as well. The temperature may be between 0 and 100° C. and the reaction time between 1 and 30 h. The amidoalkylbromides mentioned may be obtained by amination of the corresponding carboxyalkyl bromides or their acyl chloride derivatives.

Intermediates

A further embodiment of the invention relates to compounds selected from the group consisting
(7-Nitro-1H-benzimidazol-1-yl)acetonitrile,
(7-Nitro-1H-benzimidazol-1-yl)acetic acid,
2-(7-Nitro-1H-benzimidazol-1-yl)propanenitrile,
2-(7-nitro-1H-benzimidazol-1-yl)propanoic acid,
2-[(2-Bromo-6-nitrophenyl)amino]ethanol,
2-[(2-Amino-6-bromophenyl)amino]ethanol,
2-(7-Bromo-1H-benzimidazol-1-yl)ethanol,
(7-Bromo-1H-benzimidazol-1-yl)acetic acid,
8-Chloro-3-oxo-3,4dihydroquinoxaline-1(2H)-carbaldehyde,
2-[(2-Amino-6-chlorophenyl)amino]ethanol,
2-(7-Chloro-1H-benzimidazol-1-yl)ethanol,
(7-Chloro-1H-benzimidazol-1-yl)acetic acid,
(2-Methyl-6-nitrophenyl)formamide,
Ethyl N-formyl-N-(2-methyl-6-nitrophenyl)glycinate,
Ethyl N-(2-amino-6-methylphenyl)-N-formylglycinate,
(7-Methyl-1H-benzimidazol-1-yl)acetic acid,
2-[(2-Hydroxyethyl)amino]-3-nitrobenzoic acid,
Methyl 2-[(2-hydroxyethyl)amino]-3-nitrobenzoate,
Methyl 1-(2-hydroxyethyl)-1H-benzimidazole-7-carboxylate,
3-Carboxymethyl-3H-benzimidazole4-carboxylic acid methyl ester,
2-Chloro-N,N-dimethyl-3-nitrobenzenesulfonamide,
2-[(2-Hydroxyethyl)amino]-N,N-dimethyl-3-nitrobenzenesulfonamide,
3-Amino-2-[(2-hydroxyethyl)amino]-N,N-dimethylbenzenesulfonamide,
1-(2-Hydroxyethyl)-N,N-dimethyl-1H-benzimidazole-7-sulfonamide,
(7-Dimethylsulfamoyl-benzimidazol-1-yl)-acetic acid,
2-Chloro-1-nitro-3-(propylsulfonyl)benzene,
2-{[2-Nitro-6-(propylsulfonyl)phenyl]amino}ethanol,
2-{[2-Amino-6-(propylsulfonyl)phenyl]amino}ethanol,
[7-(Propylsulfonyl)-1H-benzimidazol-1-yl]acetic acid,
[7-(Methylsulfonyl)-1H-benzimidazol-1-yl]acetic acid,
2-(7-(Methylsulfonyl)-1H-benzimidazol-1-yl)-ethanol,
2-{[2-Nitro-6-(trifluoromethyl)phenyl]amino}ethanol,
2-{[2-amino-6-(trifluoromethyl)phenyl]amino}ethanol,
2-[7-(Trifluoromethyl)-1H-benzimidazol-1-yl]ethanol,
[7-(Trifluoromethyl)-1H-benzimidazol-1-yl]acetic acid,
2-[(2-hydroxyethyl)amino]-3-nitrobenzonitrile,
1-(2-hydroxyethyl)-1H-benzimidazole-7-carbonitrile,
(7-Cyano-1H-benzimidazol-1-yl)acetic acid,
2-[(2-Fluoro-6-nitrophenyl)amino]ethanol,
2-(7-Fluoro-1H-benzoimidazol-1-yl)ethanol, and
(7-Fluoro-1H-benzimidazol-1-yl)acetic acid,
which may be used as intermediates in the preparation of compounds suited for the treatment of VR1 mediated disorders, especially for use as intermediates for the preparation of compounds of formula I.

Pharmaceutical Composition

According to one embodiment of the present invention there is provided a-pharmaceutical composition comprising as active ingredient a therapeutically effective amount of the compound of formula I, or salts, solvates or solvated salts thereof, in association with one or more pharmaceutically acceptable diluents, excipients and/or inert carriers.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration e.g. as an ointment, patch or cream, for rectal administration e.g. as a suppository or for inhalation.

In general the above compositions may be prepared in a conventional manner using one or more conventional excipients, pharmaceutical acceptable diluents and/or inert carriers. Suitable daily doses of the compounds of formula I in the treatment of a mammal, including man, are approximately 0.01 to 250 mg/kg bodyweight at peroral administration and 0.001 to 250 mg/kg bodyweight at parenteral administration. The typical daily dose of the active ingredient varies within a wide range and will depend on various factors such as the relevant indication, severity of the illness being treated, the route of administration, the age, weight and sex of the patient and the particular compound being used, and may be determined by a physician.

Examples of Pharmaceutical Composition

The following illustrate representative pharmaceutical dosage forms containing a compound of formula I, or salts, solvates or solvated salts thereof, (hereafter compound X), for preventive or therapeutic use in mammals:

| (a): Tablet | mg/tablet |
|---|---|
| Compound X | 100 |
| Lactose | 182.75 |
| Croscarmellose sodium | 12.0 |
| Maize starch paste (5% w/v paste) | 2.25 |
| Magnesium stearate | 3.0 |

| (b): Capsule | mg/capsule |
|---|---|
| Compound X | 10 |
| Lactose | 488.5 |
| Magnesium stearate | 1.5 |

| (c): Injection | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | up to 100% |

The above compositions may be obtained by conventional procedures well known in the pharmaceutical art.

Medical Use

Suprisingly, it has been found that the compounds according to the present invention are useful in therapy. The compounds of formula I, or salts, solvates or solvated salts thereof, as well as their corresponding active metabolites, exhibit a high degree of potency and selectivity for individual vanilloid receptor 1 (VR1) groups. Accordingly, the compounds of the present invention are expected to be useful in the treatment of conditions associated with excitatory activation of vanilloid receptor 1 (VR1). The compounds may be used to produce an inhibitory effect of VR1 in mammals, including man.

VR1 are highly expressed the peripheral nervous system and in other tissues. Thus, it is expected that the compounds of the invention are well suited for the treatment of VR1 mediated disorders.

The compounds of formula I are expected to be suitable for the treatment of acute and chronic pain, acute and chronic neuropathic pain and acute and chronic inflammatory pain.

Examples of such disorder may be selected from the group comprising arthritis, fibromyalgia, low back pain, post-operative pain, visceral pains like chronic pelvic pain, cystitis, including interstitial cystitis, bowel syndrome (IBS), pancreatitis, ischearnic, sciatia, diabetic neuropathy, multiple sclerosis, HIV neuropathy, asthma, cough and inflammatory bowel disease (IBD).

Further relevant disorders may be selected from the group comprising gastro-esophageal reflux disease (GERD), psoriasis, cancer, emesis, urinary incontinence and hyperactive bladder.

Other relevant disorders are related to respiratory diseases and may be selected from the group comprising asthma, chronic obstructive lung disease and emphysema, lung fibrosis and interstitial lung disease.

The respiratory disease may be an acute and chronic illness and may be related to infection(s) and/or exposure to environmental pollution and/or irritants. The compounds of formula I may also be used as antitoxin to treat (over-) exposure to VR1 activators like capsaicin, tear gas, acids or heat. Regarding heat, there is a potential use for VR1 antagonists in (sun-) burn induced pain, or inflammatory pain resulting from bum injuries.

The compounds may further be used for treatment of tolerance to VR1 activators.

One embodiment of the invention relates to the use of the compounds of formula I as hereinbefore defined, in therapy.

Another embodiment of the invention relates to the use of the compounds of formula I as hereinbefore defined, for treatment of VR1 mediated disorders.

A further embodiment of the invention relates to the use of the compounds of formula I as hereinbefore defined, for treatment of acute and chronic pain disorders.

Yet another embodiment of the invention relates to the use of the compounds of formula I as hereinbefore defined, for treatment of acute and chronic neuropathic pain.

Yet a further embodiment of the invention relates to the use of the compounds of formula I as hereinbefore defined, for treatment of acute and chronic inflammatory pain.

One embodiment of the invention relates to the use of the compounds of formula I as hereinbefore defined, for treatment of arthritis, fibromyalgia, low back pain, post-operative pain, visceral pains like chronic pelvic pain, cystitis, IBS, pancreatitis or ischeamic.

Another embodiment of the invention relates to the use of the compounds of formula I as hereinbefore defined, for treatment of sciatia, diabetic neuropathy, multiple sclerosis or HIV neuropathy.

A further embodiment of the invention relates to the use of the compounds of formula I as hereinbefore defined, for treatment of asthma, cough, IBD, psoriasis, GERD, psoriasis, cancer, emesis, urinary incontinence or hyperactive bladder.

Yet another embodiment of the invention relates to the use of the compounds of formula I as hereinbefore defined, for treatment of interstitial cystitis and pain related to interstitial cystitis.

Yet a further embodiment of the invention relates to the use of the compound of formula I as hereinbefore defined, for the treatment of respiratory diseases selected from the group comprising asthma, chronic obstructive lung disease and emphysema, lung fibrosis and interstitial lung disease.

One embodiment of the invention relates to the use of the compound of formula I as hereinbefore defined, in the manufacture of a medicament for treatment of VR1 mediated disorders and for treatment of acute-and chronic pain disorders, acute and chronic neuropathic pain, acute and chronic inflammatory pain, and respiratory diseases, and any other disorder mentioned above.

Another embodiment of the invention relates to a method of treatment of VR1 mediated disorders and acute and chronic pain disorders, acute and chronic neuropathic pain, acute and chronic inflammatory pain, and respiratory diseases, and any other disorder mentioned above, comprising administrering to a mammal, including man in need of such treatment, a therapeutically effective amount of the compounds of formula I, as hereinbefore defined.

A further embodiment of the invention relates to a pharmaceutical composition comprising a compound of formula I as hereinbefore defined, for use in treatment of VR1 mediated disorders and for treatment of acute and chronic pain disorders, acute and chronic neuropathic pain, acute and chronic inflammatory pain, and respiratory diseases, and any other disorder mentioned above.

In the context of the present specification, the term "therapy" and "treatment" includes prevention and prophylaxis, unless there are specific indications to the contrary. The terms "treat","therapeutic" and "therapeutically" should be construed accordingly.

In this specification, unless stated otherwise, the term "inhibitor" and "antagonist" mean a compound that by any means, partly or completely, blocks the transduction pathway leading to the production of a response by the ligand.

The term "disorder", unless stated otherwise, means any condition and disease associated with vanilloid receptor activity.

Non-Medical Use

In addition to their use in therapeutic medicine, the compounds of formula I, or salts, solvates or solvated salts thereof, are also useful as pharmacological tools in the development and standardisation of in vitro and in vivo test systems for the evaluation of the effects of inhibitors-of VR1 related activity in laboratory animals such as cats, dogs, rabbits, monkeys, rats and mice, as part of the search for new therapeutics agents.

EXAMPLES

The invention will now be illustrated by the following non-limiting examples.

General Methods

All starting materials are commercially available or described in the literature. The $^1$H NMR spectra were recorded on Brucker at 400 MHz. The mass spectra were recorded utilising electrospray (LC-MS; LC:Waters 2790, column XTerra MS $C_8$ 2.5 µm 2.1×30 mm, buffer gradient $H_2O$+0.1% TFA:$CH_3CN$+0.04% TFA, MS: micromass ZMD// ammonium acetate buffer) ionisation techniques.

Synthesis of the key intermediates: 7- substituted benzimidazol-1-yl-acetic acids 1) (7-Nitro-1H-benzimidazol-1-yl)acetic acid (triethylammonium salt)

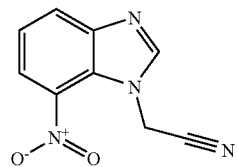

A. (7-Nitro-1H-benzimidazol-1-yl)acetonitrile

A solution (1 M) of potassium tert-butoxide (16.1 mL)) was slowly added to a solution of 4(7)-nitro-1H-benzoimidazole (2.50 g, 15.3 mmol) in dry DMF (100 mL) at 0-5° C. and the resulting dark-red solution was stirred for 15 min at room temperature. Bromoacetonitrile (1.12 mL, 16.1 mmol) was added in one portion and the reaction mixture was stirred for an additional hour, then quenched with dry ice and poured into 400 mL of cold water. The resulting clear solution was repeatedly extracted with $CHCl_3$ (4×80 mL). Organic extracts were pooled and washed with water (3×50 mL) and brine, dried over $Na_2SO_4$ and concentrated, yielding a 1:1 mixture of (4-nitro-1H-benzoimidazol-1-yl)acetonitrile and (7-nitro-1H-benzoimidazol-1-yl)acetonitrile. The regioisomers were separated on preparative HPLC (XTerra $C_8$ column 19×300 mm, 0.1 M aqueous $NH_4Ac/CH_3CN$), to yield (7-nitro-1H-benzoimidazol-1-yl)acetonitrile, 1.15 g (37%). MS (ESI) m/z: 203.05 [M+H].

$^1$H NMR (400 MHz, DMSO-D6) δ ppm 5.68 (s, 2H) 7.50 (t, J=7.8 Hz, 1H) 8.16 (m, 1 H) 8.18 (dd, J=8.1, 1.0 Hz, 1H) 8.57 (s, 1H).

B. (7-nitro-1H-benzoimidazol-1-yl)acetonitrile (1.1 g, 5.4 mmol) was dissolved in 18% hydrochloric acid (30 mL), the solution was transferred into a vial, which was sealed and heated at 105° C. for 6 h. The vial was cooled, the volatiles were removed under reduced pressure and the residue was co-evaporated two times with acetonitrile. To the residue were added dichloromethane (15 mL) and triethylamine (1 mL), and the slurry was purified on a silica gel column using a mixture of dichloromethane/methanol/triethylamine 84:15:1 (v/v/v) as an eluent to yield the title compound, 1.2 g (69%). MS (ESI) m/z: 221.98 [M-$Et_3$N+H]. $^1$H NMR (400 MHz, DMSO-D6) δ ppm 1.14 (t, J=7.1 Hz, 9 H) 2.97 (q, J=7.1 Hz, 6 H) 5.01 (s, 2H) 7.36 (t, J=8.1 Hz, 1H) 7.93 (dd, J=8.1, 1.0 Hz, 1H 8.06 (m, 1H) 8.37 (s,1H).

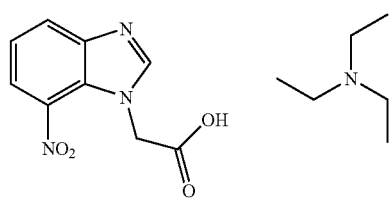

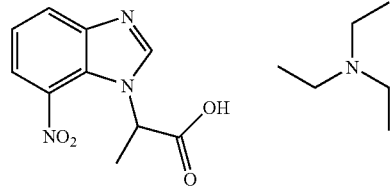

2) 2-(7-Nitro-1H-benzimidazol-1-yl)propanoic acid
(triethylammonium salt)

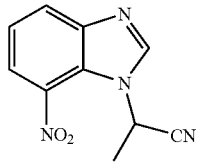

A. 2-(7-nitro-1H-benzimidazol-1-yl)propanenitrile

The compound was synthesised from 4(7)-nitro-1H-benzimidazole (1.0 g, 6.1 mmol) and 2-bromopropanenitrile (0.58 mL, 6.5 mmol) according to the procedure described for the synthesis of (7-Nitro-1H-benzimidazol-1-yl)acetic acid triethylammonium salt, part A, in a is 0.14 g (11%) yield. MS (ESI) m/z: 217.16 [M+H]. $^1$H NMR (400 MHz, DMSO-D6) δ ppm 2.01 (d, J=7.0 Hz, 3H) 6.08 (q, J=7.1 Hz, 1H) 7.48 (t, J=8.1 Hz, 1H) 8.09 (m, 1H) 8.16 (dd, J=8.0, 1.0 Hz, 1H) 8.89 (s, 1H).

B. The title compound was synthesized from 2-(7-nitro-1H-benzimidazol-1-yl)propanenitrile according to the procedure described for the synthesis of (7-Nitro-1H-benzimidazol-1-yl)acetic acid triethylammonium salt, part B, to yield 0.15 g (69%). MS (ESI) m/z: 236.08 [M-Et$_3$N+H].

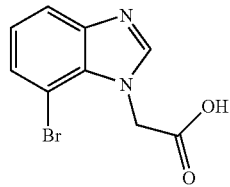

3)(7-Bromo-1H-benzimidazol-1-yl)acetic acid

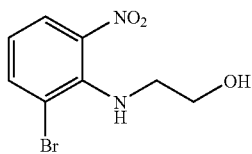

A. 2-[(2-bromo-6-nitrophenyl)amino]ethanol

A solution of 1-bromo-2-chloro-3-nitrobenzene (0.34 g, 1.4 mmol) and ethanolamine (0.22 mL, 3.5 mmol) in dry ethanol (3.8 mL) was irradiated in a microwave oven at 135° C. for 180 min. After the reaction mixture was concentrated under reduced pressure. The residue was dissolved in ethyl acetate, the organic phase was washed with potassium bisulfate (0.1 M), water and brine, dried over Na$_2$SO$_4$ and concentrated. Purification was performed using flash chromatography on a silica column and 25% ethyl acetate in heptane as an eluent to yield 2-[(2-bromo-6-nitrophenyl)amino]ethanol as red oil, 0.24 g (65%). $^1$H NMR (400 MHz, DMSO-D6) δ ppm 3.13 (q, J=5.2 Hz, 2H) 3.51 (q, J=5.1 Hz, 2H) 4.87 (t, J=5.1 Hz, 1H) 6.18 (t, J=5.1 Hz, 1H) 6.80 (t, J=8.1 Hz, 1H) 7.84 (dd, J=7.8, 3.3 Hz, 2H).

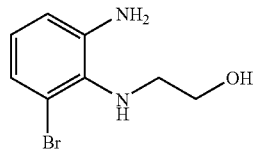

B. 2-[(2-amino-6-bromophenyl)amino]ethanol

To a solution of 2-[(2-bromo-6-nitrophenyl)amino]ethanol (1.95 g, 7.5 mmol) in a mixture of methanol (30 mL) and water (15 mL) sodium acetate trihydrate (56 g) was added. To this mixture titanium trichloride (65 mL, as 15% solution in 10% aqueous HCl) was added drop-wise over period of 20 min. The resulting dark solution was allowed to stir for additional 2 h, and then carefully neutralized with saturated aqueous sodium bicarbonate. The solids were filtered off, and washed with ethyl acetate. The combined organic phase was washed with water and brine, dried over Na$_2$SO$_4$ and concentrated yielding 2-[(2-amino-6-bromophenyl)amino]ethanol as pale-yellow oil (1.61 g, 93%) that was used in the next step without further purification. MS (ESI) m/z: 231.01[M+H].

C. 2-(7-Bromo-1H-benzimidazol-1-yl)ethanol

2-[(2-Amino-6-bromophenyl)amino]ethanol (0.14 g, 0.54 mmol) was dissolved in formic acid (3 mL) and irradiated in microwave oven at 135° C. for 2 h. The mixture was cooled and treated with 37% hydrochloric acid (1 mL) at 50° C. for 0.5 h. The volatiles were removed under reduced pressure. The residue was partitioned between ethyl acetate and to saturated aqueous sodium bicarbonate. The organic phase was washed with water and brine, dried over sodium sulfate and concentrated to yield 2-(7-bromo-1H-benzimidazol-1-yl)ethanol, 0.14 g (90%). MS (ESI) m/z: 241.09 [M+H]$^+$. $^1$H NMR (400 MHz, DMSO-d6) δ 3.76 (q, J=5.5 Hz, 2H) 4.55 (t, J=5.4 Hz, 2H) 4.97 (t, J=5.4 Hz, 1H) 7.12 (m, 1H) 7.43 (m, 1H) 7.66 (dd, J=8.0, 1.0 Hz, 1H) 8.19 (s, 1H).

D. To a solution of 2-(7-bromo-1H-benzimidazol-1-yl)ethanol (1.1 g, 4.6 mmol) in acetone (150 mL) Jones reagent (a mixture of CrO$_3$ 0.5 g, 5 mmol; H$_2$SO$_4$ 0.5 mL in a minimal amount of water to form a clear solution) was added. The reaction mixture was stirred for 6 h, quenched with 2-propanol (2 mL) and concentrated to a quarter of the initial volume. The residue was partitioned between ethyl acetate and aqueous potassium hydrosulfate (0.1 M). The aqueous phase was extracted 3-4 times with ethyl acetate and the combined organic extract was washed with brine, dried over Na$_2$SO$_4$ and concentrated. The oily residue was dissolved in a mixture of dichloromethane (15 mL) and triethylamine (2 mL) and the resulting slurry was loaded onto a flash silica column and eluted with a mixture of dichloromethane/methanol/triethylamine 84:15:1. Fractions containing product were pooled, diluted with dioxane (20 mL), evaporated to dryness and dried in vacuo at 40° C. to yield the title product, 0.79 g (48%). MS (ESI) m/z: 254.99 [M-Et$_3$N+H]. $^1$H NMR (400 MHz, DMSO-D6) δ ppm 5.28 (s, 2H) 7.14 (t, J=7.8 Hz, 1H) 7.42 (d, J=7.6 Hz, 1 H) 7.67 (d, J=8.1 Hz, 1H) 8.24 (s, 1H).

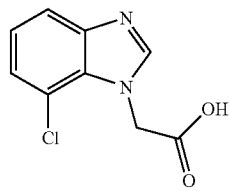

4)(7-Chloro-1H-benzimidazol-1-yl)acetic acid

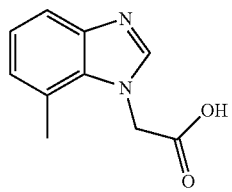

6) (7-Methyl-1H-benzimidazol-1-yl)acetic acid

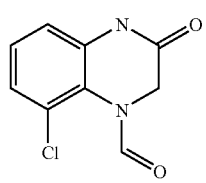

A. 8-Chloro-3-oxo-3,4-dihydroquinoxaline-1(2H)-carbaldehyde To a solution of N-(2-chloro-6-nitrophenyl)glycine (300 mg, 1.30 mol) in formic acid (16 mL) tin chloride (1.47 g, 6.50 mmol) was added at 60° C., and the mixture was stirred at this temperature for 1.5 h. The volatiles were removed in vacuo, and the residue was partitioned between a 1 M solution of sodium hydroxide and ethyl acetate. The organic phase was dried over magnesium sulfate, and concentrated. The crude product was purified by column chromatography using heptane/ethyl acetate, 1:1 as an eluent affording 8-chloro-3-oxo-3,4-dihydroquinoxaline-1(2H)-carbaldehyde (89 mg). MS (ESI) m/z: 209.2 [M−H]. $^1$H NMR (400 MHz, acetone-D6) δ ppm 4.42 (s, 2H), 7.12 (dd, J=1.5, 7.6 Hz, 1H), 7.22 (dd, J=1.5, 8.1 Hz, 1H), 7.27 (t, J=8.1 Hz, 1H), 8.62 (s, 1H), 9.8 (br.s, 1H)

B. 8-chloro-3-oxo-3,4-dihydroquinoxaline-1(2H)-carbaldehyde (89 mg) was dissolved in a mixture of formic acid (1 mL) and 37% hydrochloric acid (1 mL) and the mixture was heated at 100-105° C. for 6 h. The volatiles were removed in vacuo, and the residue was co-evaporated several times with acetonitrile affording 100 mg (31%) of the title compound as a white solid. MS (ESI) m/z: 211.0 [M+H]. $^1$H NMR (400 MHz, DMSO-D6) δ ppm 5.38 (s, 2H), 7.32 (t, J=7.8 Hz, 1H), 7.40 (d, J=7.6 Hz, 1H), 7.72 (d, J=7.8 Hz, 1H), 8.63 (s, 1H).

5)(7-Chloro-1H-benzimidazol-1-yl)acetic acid

Alternatively, the title compound was synthesised according to the procedure described for the synthesis of (7-bromo-1H-benzimidazol-1-yl)acetic acid (parts A-D) starting from 1,2-dichloro-3-nitrobenzene. The new intermediates isolated were:

2-[(2-Amino-6-chlorophenyl)amino]ethanol. MS (ESI) m/z: 187 [+H]. $^1$H NMR (400 MHz, DMSO-D6) δ 6.69 (t, J=8.0 Hz, 1H), 6.59-6.54 (m, 2H), 5.02 (broad s, 2H), 4.75 (t, J=5.2 Hz, 1H), 3.84 (t, J=7.2 Hz, 1H), 3.53-3.49 (m, 2H), 2.95-2.91 (m, 2H), and 2-(7-Chloro-1H-benzimidazol-1-yl)ethanol. MS (ESI) m/z: 197 [M+H]. $^1$H NMR (400 MHz, DMSO-d6) δ 3.75 (q, J=5.6 Hz, 2H) 4.53 (t, J=5.6 Hz, 2H) 4.96 (t, J=5.1 Hz, 1H) 7.18 (t, J=8.1 Hz, 1H) 7.27 (dd, J=8.0, 1.0 Hz, 1H) 7.62 (dd, J=8.0, 1.0 Hz, 1H) 8.18 (s, 1H).

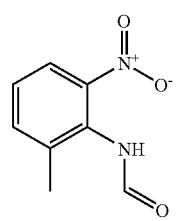

A. (2-Methyl-6-nitrophenyl)formamide

Formic acid (0.97 g, 21.0 mmol) was added to acetic anhydride (1.74 g, 17.1 mmol) and the mixture was heated at 50° C. for 0.5 h. 2-Methyl-6-nitroaniline (1.0 g, 6.57 mmol) was added, and the mixture was heated at 50° C. for additional 1.5 h. Volatiles were removed in vacuo, and the residue was partitioned between water and ethyl acetate. The organic phase was washed with a saturated solution of sodium bicarbonate and brine, dried over magnesium sulfate. The volatiles were removed in vacuo affording 1.10 g of a solid residue. The crude product was recrystallized from ethyl acetate/heptane (1: 1) affording 0.57 g (48% yield) of (2-methyl-6-nitrophenyl)formamide as a white solid. MS (ESI) m/z 179 [M−H]. $^1$H NMR (400 MHz, CDCl$_3$) δ ppm 2.37 (s, 3H), 7.33 (t, J=8.0 Hz, 1H), 7.56 (d, J=7.3 Hz, 1H), 7.88 (d, J=7.8 Hz, 1H), 8.50-8.20 m (2H).

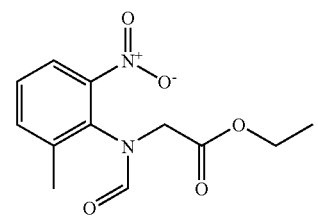

B. Ethyl N-formyl-N-(2-methyl-6-nitrophenyl)glycinate

To a mixture of (2-methyl-6-nitrophenyl)formamide (180 mg, 1.0 mmol), potassium carbonate (276 mg, 2.0 mmol), potassium iodide (5 mg) and N,N-dimethylformamide (1 mL) a solution of ethyl bromoacetate (184 mg, 1 mmol) in N,N-dimethylformamide (1 mL) was added at room temperature. The mixture was heated at 60° C. for 3 h, then cooled to room temperature. The mixture was partitioned between water and ethyl acetate. The organic layer was separated, washed with brine and dried over magnesium sulfate. The volatiles were removed in vacuo. The crude product was purified by column chromatography using heptane/ethyl acetate (70:30→50:50) as an eluent affording ethyl N-formyl-N-(2-methyl-6-nitrophenyl)glycinate, 167 mg (63% yield) as an oil. MS (1S) m/z 267 [M+H].

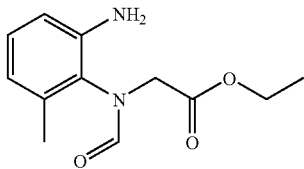

C. Ethyl N-(2-amino-6-methylphenyl)-N-formylglycinate

A solution of ethyl N-formyl-N-(2-methyl-6-nitrophenyl) glycinate (154 mg, 0.58 mmol) in methanol containing 5% Pd/C (35 mg) was hydrogenated at 1 atmosphere for 1 h. The mixture was filtered through a pad of celite, and the solvent was removed in vacuo affording ethyl N-(2-amino-6-methylphenyl)-N-formylglycinate, 127 mg (93%) as an oil. MS (ESI) m/z 237 [M+H]. $^1$H NMR (400 MHz, CDCl$_3$) δ ppm 1.30 (t, J=7.2Hz, 3H), 2.14 (s, 3H), 3.60 (d, J=17 Hz, 1H), 4.32-4.18 (m, 2H), 4.70 (br. s, 2 H), 4.77 (d, J=17 Hz, 1H), 6.60 (app t, J=8.0 Hz, 2H), 7.05 (t, J=7.8 Hz, 1H), 8.11 (s, D. A solution of ethyl N-(2-amino-6-methylphenyl)-N-formylglycinate (115 mg, 0.49 mmol) in formic acid (5 mL) was heated at reflux for 1 h, then allowed to cool to room temperature. The volatiles were removed in vacuo. The residue was dissolved in hydrochloric acid (6 M, 4 mL) and the solution was heated at reflux for 1 h. The volatiles were removed in vacuo, and the residue was co-evaporated several times with acetonitrile. The residue was suspended in acetonitrile, filtered, and dried in vacuo affording the title compound, 96 mg (86%) as a solid. MS (ESI) m/z 189 [M−H]. $^1$H NMR (400 MHz, DMSO-D6) δ ppm 2.63 (s, 3H), 5.55 (s, 2H), 7.34 (d, J=7.3 Hz, 1H), 7.46 (t, J=7.8 Hz, 1H), 7.71 (d, J=8.3 Hz, 1H), 9.43 (s, 1H).

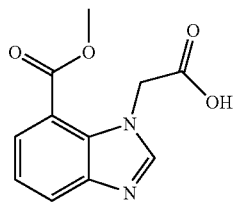

7) 3-Carboxymethyl-3H-benzimidazole4-carboxylic acid methyl ester

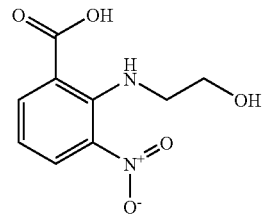

A. 2-[(2-Hydroxyethyl)amino]-3-nitrobenzoic acid

2-Chloro-3-nitrobenzoic acid (5.0 g, 24.8 mmol) was suspended in ethanol (90 mL) and ethanolamine (4.5 mL, 74.8 mmol) was added. The resulting clear solution was heated at 100° C. for two days. The volatiles were removed under reduced pressure. The residue was treated with water (40 mL) and the mixture was acidified with 1M hydrochloric acid to pH 2. A yellow precipitate formed was collected by filtration and washed with water to yield 2-(2-hydroxyethylamino)-3-nitrobenzoic acid, 5.14 g (92%). MS (ESI) m/z 225 [M−H]. $^1$H NMR (400 MHz, CD$_3$OD) δ ppm 3.04 (t, J=5.31 Hz, 2H), 3.69 (t, J=5.31 Hz, 2H), 6.71 (t, J=7.96 Hz, 1H), 7.93 (dd, J=8.21, 1.64 Hz, 1H), 8.13 (dd, J=7.71, 1.64 Hz, 1H).

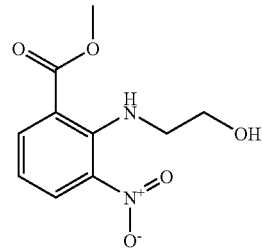

B. Methyl 2-[(2-hydroxyethyl)amino]-3-nitrobenzoate 2-(2-Hydroxyethylamino)-3-nitrobenzoic acid (5.14 g, 22.7 mmol) was dissolved in methanol (200 mL) and concentrated H$_2$SO$_4$ (10 mL) was added. The mixture was heated at reflux for 2.5 h. The solvent was removed at reduced pressure. The residue was treated with water (100 ml) and extracted with ethyl acetate (3×150 mL). The combined organic phase was dried and concentrated. Purification by column chromatography on silica using heptane ethyl acetate 1:1 as an eluent afforded methyl 2-[(2-hydroxyethyl)amino]-3-nitrobenzoate, 3.92 g (72%). MS NISI) m/z 241 [M+H]. $^1$H NMR (400 MHz, CDCl$_3$) δ ppm 3.12 (t, J=5.10 Hz, 2H), 3.84 (t, J=5.15 Hz, 2H), 3.91 (s, 3H), 6.69 (t, J=7.96 Hz, 1H), 7.95 (dd, J=8.34, 1.52 Hz, 1H), 8.08 (dd, J=7.83, 1.52 Hz, 1H).

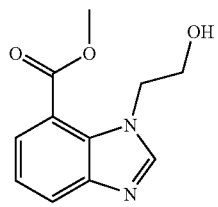

C. Methyl 1-(2-hydroxyethyl)-1H-benzimidazole-7-carboxylate

Suspension of methyl 2-[(2-hydroxyethyl)amino]-3-nitrobenzoate (3.06 g, 12.7 mmol) in methanol (130 mL) was hydrogenated at atmospheric pressure over 10% palladium on activated charcoal for 10 min. The mixture was filtered through a pad of Celite and the solvent was removed in vacuum. The residue was dissolved in formic acid (60 mL) and heated at 100° C. for 45 min and then kept at ambient temperature overnight. Excess of the formic acid was removed under reduced pressure. The residue was dissolved in methanol (100 mL) and treated with concentrated ammonia in methanol (20 mL) for 50 min followed by evaporation of the volatiles. Purification by column chromatography on silica using dichloromethane in methanol 95:5 afforded methyl 1-(2-hydroxyethyl)-1H-benzimidazole-7-carboxylate, 2.31 g (83%). %). MS (ESI) m/z 221 [M+H]. $^1$H NMR (400 MHz, CD$_3$OD) δ ppm 3.78 (t, J=5.05 Hz, 2H), 3.96 (s, 3H), 4.70 (t, J=5.05 Hz, 2H), 7.33 (t, J=7.83 Hz, 1H), 7.84-7.91 (m, 2H), 8.20 (s, 1H).

D. To a solution of methyl 1-(2-hydroxyethyl)-1H-benzimidazole-7-carboxylate (2.83 g, 12.8 mmol) in acetone (140 mL) a solution of CrO$_3$ (1.77 g, 17.7 mmol) and concentrated H$_2$SO$_4$ (1.77 mL) in water (5 mL) was added. The resulting yellow solution was stirred at ambient temperature for 1 h, while the mixture had changed colour to blue green, and then was quenched by the addition of isopropanol. The volatiles were removed in vacuum. The residue was treated with brine and pH of the solution was adjusted to 3 by addition of aqueous sodium bicarbonate. The water phase was repeatedly extracted with ethyl acetate containing 5% methanol. Drying of the organic phase with sodium sulfate, evaporation of solvent and purification of the residue by column chromatography on silica using a gradient of 10-25% methanol in dichloromethane afforded the title compound, 1.44 g (48%). MS (ESI) m/z 235 [M+H]. $^1$H NMR (400 MHz, D$_2$O) δ ppm 3.95 (s, 3H), 5.17 (s, 2H), 7.57 (t, J=7.95 Hz, 1H), 7.96-8.05 (m, 2H), 8.79 (s, 1H).

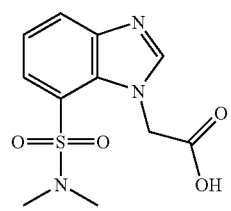

8) (7-Dimethylsulfamoyl-benzimidazol-1-yl)-acetic acid

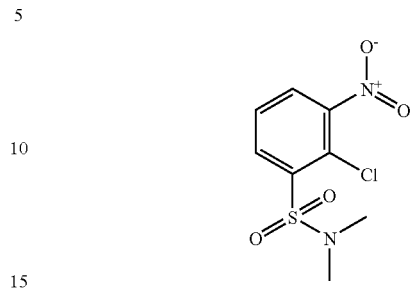

A. 2-Chloro-N,N-dimethyl-3-nitrobenzenesulfonamide

2-Chloro-3-nitrobenzenesulfonyl chloride (235 mg, 0.918 mmol) was treated with a 2 M solution of dimethylamine in methanol (0.55 mL, 1.10 mmol), and triethylamine (0.13 mL, 0.918 mmol) in methanol (1 mL), and the suspension was stirred at room temperature for 2.5 h. The volatiles were removed in vacuo, and the residue was purified by column chromatography using heptane/ethyl acetate, 70:30-50:50 as an eluent, affording 2-chloro-N,N-dimethyl-3-nitrobenzenesulfonamide, 202 mg (83%) as a white solid. MS (ESI) m/z 265 [M+H]. $^1$H NMR (400 MHz, CDCl$_3$) δ ppm 2.95 (s, 6H); 7.56 (t, J=8.0 Hz, 1H), 7.88 (dd, J=8.1, 1.5 Hz, 1H), 8.31 (dd, J=8.1, 1.5 Hz, 1H).

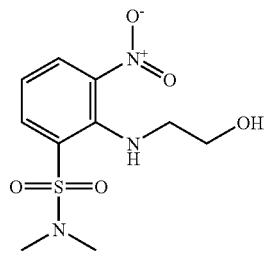

B. 2-[(2-Hydroxyethyl)amino]-N,N-dimethyl-3-nitrobenzenesulfonamide

A solution of 2-chloro-N,N-dimethyl-3-nitrobenzenesulfonamide (170 mg, 0.642 mmol) and ethanolamine (196 mg, 3.21 mmol) in ethanol (6 mL) was heated at reflux for 4 h. The solvent was removed in vacuo, and the residue was purified by column chromatography using heptane/ethyl acetate, 1:1 as an eluent affording 2-[(2-hydroxyethyl)amino]-N,N-dimethyl-3-nitrobenzenesulfonamide, 161 mg (87%). MS (ESI) mm/z 288 [M–H]. $^1$H NMR (400 MHz, CDCl$_3$) δ ppm 1.92 (t, J=5.6 Hz, 1H), 2.83 (s, 6 H), 3.10-3.06 (m, 2H), 3.84-3.80 (m, 2H), 6.83 (t, J=8.0 Hz, 1H), 6.87 (broad s, 1H), 7.91-7.87 (m, 2H).

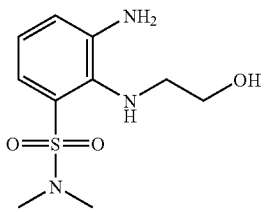

C. 3-Amino-2-[(2-hydroxyethyl)amino]-N,N-dimethylbenzenesulfonamide

To a solution of 2-[(2-hydroxyethyl)amino]-N,N-dimethyl-3-nitrobenzenesulfonamide (107 mg, 0.37 mmol) in methanol (2 mL) a solution of 85% sodium hydrosulfite (0.30 g, 1.5 mmol) in water (1.2 mL) was added. The obtained suspension was heated at 60° C. for 10 min. The volatiles were removed in vacuo, and the residue was partitioned between a saturated solution of sodium bicarbonate and ethyl acetate. The organic phase was dried over magnesium sulfate and concentrated in vacuo affording 3-amino-2-[(2-hydroxyethyl)amino]-N,N-dimethylbenzenesulfonamide, 69 mg (72 %) as an oil: MS (ESI) m/z 260 [M+H].

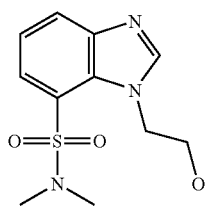

D. 1-(2-Hydroxyethyl)-N,N-dimethyl-1H-benzimidazole-7-sulfonamide

A solution of 3-amino-2-[(2-hydroxyethyl)amino]-N,N-dimethylbenzenesulfonamide (69 mg, 0.266 mmol) in formic acid (2 mL) and 2 M hydrochloric acid (2 mL) was heated at reflux for 1 h. The volatiles were removed in vacuo, and the residue was partitioned between an aqueous sodium hydroxide solution and ethyl acetate. The organic phase was dried over magnesium sulfate and concentrated in vacuo affording 1-(2-hydroxyethyl)-N,N-dimethyl-1H-benzimidazole-7-sulfonamide, 66 mg. MS (ES) m/z 270 [M+H]⁺.

E. To a solution of 1-(2-hydroxyethyl)-N,N-dimethyl-1H-benzimidazole-7-sulfonamide (66 mg) in acetone (3 mL) 2.6 M solution of Jones reagent (0.28 mL, 0.74 mmol; a stock solution was prepared by dissolving 0.52 g of CrO₃ and 0.52 mL of concentrated H₂SO₄ in water to a total volume of 2.0 mL) was added. The reaction mixture was stirred at room temperature for 2 h, then quenched with 2-propanol. The volatiles were removed in vacuo. The residue was treated with brine, and basicified with aqueous solution of sodium hydroxide to pH 4. The aqueous phase was extracted twice with ethyl acetate. The combined organic phase was dried over magnesium sulfate and concentrated affording the title compound, 51 mg (74%). MS (ES) m/z 282 [M−H].

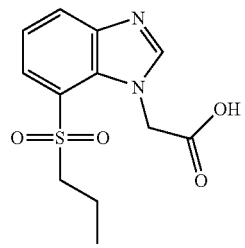

9) [7-(Propylsulfonyl)-1H-benzimidazol-1-yl]acetic acid

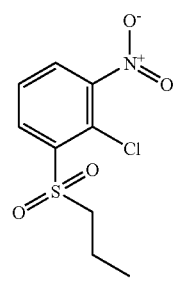

A. 2-Chloro-1-nitro-3-(propylsulfonyl)benzene

To an ice-cooled solution of 2-chloro-1-nitro-3-(propylthio)benzene (0.71 g, 3.06 mmol) in N,N-dimethylformamide (10 mL) m-chloroperbenzoic acid (2.1 g, 9.19 mmol) was added in portions. The ice-bath was removed, and the reaction mixture was stirred at ambient temperature for 24 h. The volatiles were removed in vacuo. The residue was treated with 1 M solution of sodium hydroxide and extracted with ethyl acetate. The organic phase was dried over magnesium sulfate and concentrated to leave a crude product, 0.88 g as an oil. Purification by column chromatography on silica using heptane/ethyl acetate, 70:30 as an eluent afforded 2-chloro-1-nitro-3-(propylsulfonyl)benzene, 657 mg (81%) as a white solid. ¹H NMR (400 MHz, CDCl₃) δ ppm 1.06 (t, J=7.4 Hz, 3H), 1.84-1.74 (m, 2H), 3.45-3.41 (m, 2H), 7.65 (t, J=8.1 Hz, 1H), 7.99 (dd, J=8.1, 1.5 Hz, 1H), 8.37 (dd, J=8.1, 1.5 Hz, 1H).

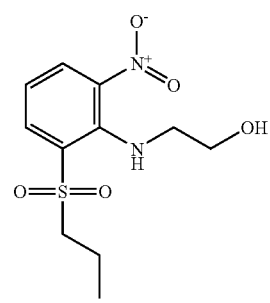

B. 2-{[2-Nitro-6-(propylsulfonyl)phenyl]amino}ethanol

The compound was synthesized in 99% yield according to the procedure described for the synthesis of (7-dimethylsulfamoyl-benzoimidazol-1-yl)-acetic acid, part B, starting from 2-chloro-1-nitro-3-(propylsulfonyl)benzene. MS (ESI) m/z 289 [M+H]. ¹H NMR (400 MHz, CDCl₃) δ ppm 1.02 (t, J=7.4 Hz, 3H), 1.80-1.70 (m, 3H), 3.13-3.09 (m, 2H), 3.27-3.23 (m, 2H), 3.87-3.84 (m, 2H), 6.88 (t, J=8.0 Hz, 1H), 6.95 (broad s, 1H), 7.91 (dd, J=8.1, 1.5 Hz, 1H), 7.99 (dd, J=7.8, 1.8 Hz, 1H).

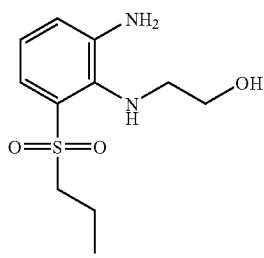

C. 2-{[2-Amino-6-(propylsulfonyl)phenyl]amino}ethanol

The compound was synthesized in 52% yield according to the procedure described for the synthesis of (7-dimethylsulfamoyl-benzimidazol-1-yl)-acetic acid, part C, starting from 2-{[2-nitro-6-(propylsulfonyl)phenyl]amino}ethanol. MS (ESI) m/z 259 [M+H]. ¹H NMR (400 MHz, CDCl₃/CD₃OD) δ ppm 1.00 (t, J=7.3 Hz, 3H), 1.82-1.72 (m, 2H), 3.15-3.11 (m, 2H), 3.29-3.27 (m, 2H), 3.80-3.77 (m, 2H), 6.92-6.90 (m, 1H), 6.96 (t, J=7.8 Hz, 1H), 7.23 (dd, J=7.7, 1.6 Hz, 1H)

D. The title compound was synthesized according to the procedure described for the synthesis of (7-Dimethylsulfamoyl-benzimidazol-1-yl)-acetic acid part D and E, starting from 2-{[2-amino-6-(propylsulfonyl)phenyl]amino}ethanol. MS (ESI) m/z 281 [M−H].

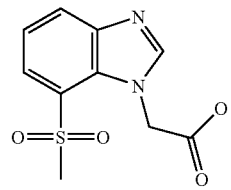

11)
[7-(Methylsulfonyl)-1H-benzimidazol-1-yl]acetic acid

A. 2-(7-(Methylsulfonyl)-1H-benzimidazol-1-yl)-ethanol

This compound was synthesized according to the procedure described for the synthesis of [7-(propylsulfonyl)-1H-benzimidazol-1-yl]acetic acid starting from 2-chloro-1-nitro-3-(methylthio)benzene. MS (ESI) m/z 241 [M+H]. ¹H NMR (400 MHz, DMSO-D6) δ 8.39 (s, 1H), 8.05 (dd, J=8.1, 1.0 Hz, 1H), 7.86 (dd, J=7.8, 1.0 Hz, 1H), 7.42 (t, J=8.0 Hz, 1H), 5.01 (t, J=5.1 Hz, 1H), 4.71 (t, J=5.2 Hz, 2H), 3.79-3.76 (m, 2H), 3.46 (s, 3H).

B. The title compound was synthesized from 2-(7-(methylsulfonyl)-1H-benzimidazol-1-yl)-ethanol according to the procedure described for the synthesis (7-dimethylsulfamoyl-benzimidazol-1-yl)-acetic acid, part E, and used as such without further purification in the synthesis of the target compound.

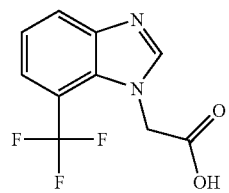

11)
[7-(Trifluoromethyl)-1H-benzimidazol-1-yl]acetic acid

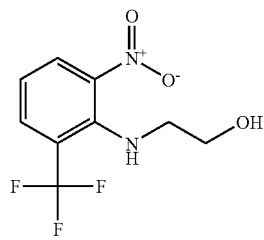

A. 2-{[2-Nitro-6-(trifluoromethyl)phenyl]amino}ethanol

To a suspension of sodium perborate tetrahydrate (7.69 g, 50 mmol) in acetic acid (30 mL) a solution of 3-amino-2-nitrobenzotrifluoride (2.06 g, 10 mmol) in acetic acid (25 mL) was added dropwise at 55° C. over 1.5 h. The mixture was stirred at 55° C. overnight. Precipitated material was filtered off, and the filtrate was concentrated in vacuo. The residue was suspended in 2 M hydrochloric acid and filtered. The precipitate was washed with 2 M hydrochloric acid and water, and then dried in vacuum at room temperature affording a yellow solid, 1.14 g. This material was suspended in ethanol (10 mL), and a solution of ethanolarine (1.10 g, 18.1 mmol) in ethanol (10 mL) was added. The reaction mixture was heated at reflux for 20 min, and then allowed to cool to room temperature. The volatiles were removed in vacuo. The residue was purified by column chromatography on silica using heptane/ethyl acetate, 80:20 as an eluent affording 0.72 g (29% yield) of 2-{[2-nitro-6-(trifluoromethyl)phenyl]amino}ethanol as an orange oil. MS (ESI) m/z 249 (M−H). ¹H NMR (400 MHz, CDCl₃) δ ppm 3.38-3.34 (m, 2H), 3.85-3.82 (m, 2H), 6.88-6.84 (m, 2H), 7.77 (dd, J=7.8, 1.3 Hz, 1H), 8.11 (dd, J=8.3, 1.5 Hz, 1H).

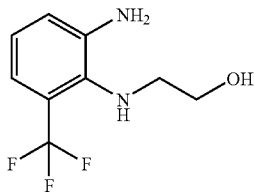

B. 2-{[2-amino-6-(trifluoromethyl)phenyl]amino}ethanol

To a solution of 2-{[2-nitro-6-(trifluoromethyl)phenyl]amino}ethanol (0.72 g, 2.88 mmol) in methanol (30 mL) a suspension of 85% sodium hydrosulfite (2.0 g, 9.8 mmol) in water (6 mL) was added. Additional water (4 mL) was added, and the mixture was heated at 60° C. for 15 min. The reaction mixture was cooled and concentrated in vacuo. The residue was extracted with ethyl acetate, and the organic phase was dried over magnesium sulfate. The solvent was removed in vacuo affording 0.57 g of 2-{[2-amino-6-(trifluoromethyl)phenyl]amino}ethanol: MS (ES) m/z 219 [M−H].

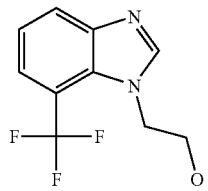

C. 2-[7-(Trifluoromethyl)-1H-benzimidazol-1-yl]ethanol

A solution of 2-{[2-amino-6-(trifluoromethyl)phenyl]amino}ethanol (0.57 g) in formic acid (20 mL) was heated at reflux for 20 min. The excess of formic acid was removed in vacuo; the residue was dissolved in a 2 M hydrochloric acid, and heated at reflux for 10 min. The solution was concentrated in vacuum and the residue was co-evaporated with acetonitrile and ethanol. The residue was treated with a saturated solution of sodium bicarbonate and extracted twice with ethyl acetate. The organic phase was washed with brine, dried over magnesium sulfate and concentrated. The crude product was purified by column chromatography on silica using ethyl acetate as an eluent affording 2-[7-(trifluoromethyl)-1H-benzimidazol-1-yl]ethanol, 0.36 g (55% yield) as a white solid. MS (ESI) m/z 231 [M+H]. $^1$H NMR (400 MHz, DMSO-D6) δ ppm 3.74-3.70 (m, 2H), 4.37 (t, J=5.3 Hz, 2H), 5.06 (t, J=4.8 Hz, 1H), 7.39 (t, J=7.8 Hz, 1H), 7.67 (d, J=7.8 Hz, 1H), 8.01 (d, J=8.1 Hz, 1H), 8.33 (s, 1H).

D. To a solution of 2-[7-(trifluoromethyl)-1H-benzimidazol-1-yl]ethanol (55 mg, 0.239 mmol) in acetone (4 mL) a 2.6 M solution of Jones reagent (0.28 mL, 0.72 mmol; a stock solution was prepared by dissolving 0.52 g of CrO$_3$ and 0.52 mL of conc. H$_2$SO$_4$ in water to a total volume of 2.0 mL) was added. The mixture was stirred at room temperature for 30 min. Another 0.1 mL of Jones reagent was added, and the mixture was stirred for a further 15 min. The reaction mixture was quenched by dropwise addition of 2-propanol (0.2 mL), stirred for 5 min, and then decanted. Remaining chromium salts were washed with 2-propanol. The combined organic phase was concentrated in vacuum. The residue was treated with brine and basicified with 1 M solution of sodium hydroxide to pH 4. The water phase was extracted twice with ethyl acetate. The organic phase was dried over magnesium sulfate and concentrated in vacuum affording the title compound (42 mg) as a solid. MS (ESI) m/z 243 [M−H].

12) (7-Cyano-1H-benzimidazol-1-yl)acetic acid

A. 2-[(2-Hydroxyethyl)amino]-3-nitrobenzonitrile

2-[(2-hydroxyethyl)amino]-3-nitrobenzonitrile was prepared starting from 2-chloro-3-nitrobenzonitrile [prepared as described in WO 97/38983] (0.89 g) according to the procedure described for the synthesis of 2-[(2-bromo-6-nitrophenyl)amino]ethanol. Yield 1.06 g (99 %). $^1$H NMR (400 MHz, CD$_3$CN) δ ppm: 3.00 (t, J=4.8 Hz, 1H), 3.68 (q, J=4.7 Hz, 2H), 3.81 (m, 2H), 6.70 (dd, J=8.6, 7.6 Hz, 1H), 7.75 (dd, J=7.6, 1.5 Hz, 1H), 8.28 (dd, J=8.6, 2.0 Hz, 1H), 8.41 (bs, 1H).

B. 1-(2-Hydroxyethyl)-1H-benzimidazole-7-carbonitrile 1-(2-Hydroxyethyl)-1H-benzimidazole-7-carbonitrile was prepared in two steps starting from 2-[(2-hydroxyethyl)amino]-3-nitrobenzonitrile (0.99 g) according to the procedure described for the synthesis of 2-(7-bromo-1H-benzimidazol-1-yl)ethanol. Yield 0.49 g (55 %). MS (ESI) m/z 188.1 [M+H]. $^1$H NMR (400 MHz, DMSO-D6) δ ppm: 3.81 (q, J=5.1 Hz, 2H), 4.53 (t, J=5.3 Hz, 2H), 5.03 (t, J=5.1 Hz, 1H) 7.36 (t, J=7.8 Hz, 1H), 7.76 (dd, J=7.6, 1.0 Hz, 1H), 8.04 (dd, J=8.1, 1.0 Hz, 1H), 8.37 (s, 1H).

C. (7-Cyano-1H-benzimidazol-1-yl)acetic acid was prepared starting from 1-(2-hydroxyethyl)-1H-benzimidazole-7-carbonitrile (89 mg) according to the procedure described for the synthesis of (7-bromo-1H-benzoimidazol-1-yl)acetic acid. Yield 38 mg (39 %). MS (ESI) m/z 202.0 [M+H]. $^1$H NMR (400 MHz, DMSO-D6) δ ppm: 5.31 (s, 2 H), 7.37 (dd, J=8.1, 7.7 Hz, 1H), 7.75 (dd, J=7.6, 0.8 Hz, 1H), 8.04 (dd, J=8.1, 1.1 Hz, 1H), 8.38 (s, 1H), 13.43 (bs, 1H).

13) (7-Fluoro-1H-benzimidazol-1-yl)acetic acid

A. 2-[(2-Fluoro-6-nitrophenyl)amino]ethanol

2-[(2-Fluoro-6-nitrophenyl)amino]ethanol was prepared starting from 1,2-difluoro-3-nitrobenzene (0.66 g) according to the procedure described for the synthesis of 2-[(2-bromo-6-nitrophenyl)amino]ethanol. Yield 0.78 g (95%). MS (ESI) m/z 201.1 [M+H]. $^1$H NMR (400 MHz, DMSO-D6) δ ppm: 3.56 (m, 4 H), 4.91 (m, 1H), 6.70 (m, 1H), 7.46 (m, 1H), 7.85 (bs, 1H), 7.89 (m, 1H).

B. 2-(7-Fluoro-1H-benzoimidazol-1-yl)ethanol

To a solution of 2-[(2-fluoro-6-nitrophenyl)amino]ethanol (0.78 g ) in methanol (15 mL) 10% palladium on carbon (200 mg) was added. The mixture was hydrogentated at hydrogen pressure 1 bar until the consumption of hydrogen gas ceased (60 min). The reaction mixture was filtered through a pad of Celite, which was further washed with methanol and acetonitrile. The filtrate was concentrated to dryness and the residue was dissolved in formic acid (4 mL). The solution was transferred into a microwave vial, which was sealed and irradiated for 15 min at 135° C. The solvent was removed in vacuum, the residue was dissolved in methanol (4 mL) and a 7 M solution of ammonia in methanol (4 mL) was added. After 10 min the mixture was concentrated to dryness and the residue was purified on a short silica column. Yield 0.65 g (93%). MS (ESI) m/z 181.1 [M+H]. $^1$H NMR (400 MHz, DMSO-D6) δ ppm: 3.60 (t, J=5.3 Hz, 2H), 4.21 (t, J=5.3 Hz, 2H), 6.92 (dd, J=12.1, 8.1 Hz, 1H), 7.02 (m, 1H), 7.34 (d, J=8.1 Hz, 1H), 8.03 (s, 1H), 8.26 (s, 1H).

C. (7-Fluoro-1H-benzimidazol-1-yl)acetic acid was prepared according to the procedure described for the synthesis of (7-bromo-1H-benzoimidazol-1-yl)acetic acid. MS (ESI) m/z 195.0 [M+H]. $^1$H NMR (400 MHz, DMSO-D6) δ ppm: 5.32 (s, 2H), 7.30 (dd, J=11.6, 8.1 Hz, 1H), 7.40 (m, 1H), 7.62 (d, J=8.1 Hz, 1H), 8.97 (s, 1H). $^{19}$F NMR (376 MHz, DMSO-D6) δ ppm: −133.66 (s, 1 F).

Synthesis of the Target Compounds

General Method.

To an ice-cooled solution of a 7-substituted (1H-benzimidazol-1-yl)acetic acid, prepared as described above (0.14 mmol), triethylamine (0.80 mL, 0.56 mmol) and an appropriate amine (0.2 mmol) in acetonitrile (2 mL) O-(7-azabenzotriazol-1-yl)-N,N,N',N'-tetramethyluronium hexafluorophosphate (69 mg, 0.18 mmol) ) was added. The ice-bath was removed, and the reaction mixture was stirred at ambient temperature for 0.5-2 h. The mixture was quenched with methanol and the volatiles were removed in vacuo. The residue was purified by column chromatography on silica using a solution of 0-10% methanol in ethyl acetate as an eluent affording the title compound. Alternatively, the residue was purified by preparative BPLC on XTerra $C_8$ column (19×300 mm) using 0.1 M aqueous $NH_4OAc/CH_3CN$ as an eluent.

| Example number | Name | MW calcd | MW found [M + 1] or [M − 1] | $^1$H NMR |
|---|---|---|---|---|
| 1 | N-(3-Fluoro-4-methoxyphenyl)-2-(7-nitro-1H-benzoimidazol-1-yl)-acetamide | 344.3 | 345.1 | (400MHz, CDCl$_3$/CD$_3$OD) δ ppm 3.79(s, 3H), 5.30(s, 2H), 6.82-6.92(m, 1H), 7.10-7.19(m, 1H), 7.28-7.42(m, 2H), 8.01-8.13(m, 3H) |
| 2 | N-[2-Fluoro-4-(trifluoromethyl)phenyl]-2-(7-nitro-1H-benzimidazol-1-yl)acetamide | 382.4 | no | (400MHz, CDCl$_3$/CD$_3$OD) δ ppm 5.42(s, 2H), 7.27-7.40(m, 3H), 8.02-8.11(m, 3H), 8.12-8.23(m, 1H) |
| 3 | N-(3-Chloro-4-iodophenyl)-2-(7-nitro-1H-benzimidazol-1-yl)acetamide | 456.6 | no | (400MHz, CDCl$_3$/CD$_3$OD) δ ppm 5.27(s, 2H), 7.08(dd, J=2.5, 8.6Hz, 1H), 7.33(t, J=8.1Hz, 1H), 7.65(d, J=8.6Hz, 1H), 7.68(d, J=2.5Hz, 1H), 7.99-8.04(m, 3H) |
| 4 | N-(3-Chloro-4-methoxyphenyl)-2-(7-nitro-1H-benzimidazol-1-yl)acetamide | 360.8 | no | (400MHz, DMSO-d6) δ ppm 3.80(s, 3H), 5.37(s, 2H), 7.11(d, J=9.1Hz, 1H), 7.36(dd, J=2.5, 9.1Hz, 1H), 7.42(t, J=8.1Hz, 1H), 7.64(d, J=2.5Hz, 1H), 8.02(d, J=8.1Hz, 1H), 8.13(dd, J=1.0, 8.1Hz, 1H), 8.44(s, 1H), 10.4(br.s, 1H) |
| 5 | N-[3-(Difluoromethoxy)phenyl]-2-(7-nitro-1H-benzimidazol-1-yl)acetamide | 362.3 | no | (400MHz, CDCl$_3$/CD$_3$OD) δ ppm 5.30(s, 2H), 6.45(t, J=74Hz, 1H), 6.74-6.82(m, 1H), 7.16-7.30(m, 3H), 7.31-7.40(m, 1H), 8.00-8.09(m, 2H), 8.09-8.17(m, 1H) |
| 6 | N-[3-methoxy-5-(trifluoromethyl)phenyl]-2-(7-nitro-1H-benzimidazol-1-yl)acetamide | 394.3 | no | (400MHz, CDCl$_3$/CD$_3$OD) δ ppm 3.73(s, 3H), 5.32(s, 2H), 6.80(br.s, 1H), 7.24(br.s, 1H), 7.35(t, J=8.1Hz, 1H), 7.38(br.s, 1H), 8.01-8.08(m, 2H), 8.15(br.s, 1H) |
| 7 | N-(3,5-Difluorophenyl)-2-(7-nitro-1H-benzimidazol-1-yl)acetamide | 332.3 | no | (400MHz, CDCl$_3$/CD$_3$OD) δ ppm 5.32(s, 2H), 6.43-6.52(m, 1H), 7.03-7.13(m, 2H), 7.33-7.42(m, 1H), 8.01-8.10(m, 2H), 8.19(s, 1H) |
| 8 | 2-(7-Nitro-1H-benzimidazol-1-yl)-N-[4-(trifluoromethoxy)phenyl]acetamide | 380.3 | no | (400MHz, CDCl$_3$/CD$_3$OD) δ ppm 5.29(s, 2H), 7.07(d, J=8.8Hz, 2H), 7.33(t, J=8.1Hz, 1H), 7.47(d, J=8.9Hz, 2H), 8.00-8.06(m, 2H), 8.08(s, 1H) |
| 9 | 2-(7-Nitro-1H-benzimidazol-1-yl)-N-[3-(1,1,2,2-tetrafluoroethoxy)phenyl]acetamide | 412.3 | no | (400MHz, CDCl$_3$/CD$_3$OD) δ ppm 5.32(s, 2H), 5.85(t, J=52Hz, 1H), 6.85-6.92(m, 1H), 7.18-7.35(m, 3H), 7.43(s, 1H), 7.99-8.08(m, 2H), 8.14(s, 1H) |
| 10 | N-(4-tert-Butylphenyl)-2-(7-nitro-1H-benzimidazol-1-yl)acetamide | 352.4 | no | (400MHz, CDCl$_3$/CD$_3$OD) δ ppm 1.22(s, 9H), 5.29(s, 2H), 7.24(d, J=8.6Hz, 2H), |

-continued

| Example number | Name | MW calcd | MW found [M + 1] or [M − 1] | ¹H NMR |
|---|---|---|---|---|
| 11 | N-[3-(1-Hydroxyethyl)phenyl]-2-(7-nitro-1H-benzimidazol-1-yl)acetamide | 340.3 | 341.2 | 7.34(d, J=8.7Hz, 3H), 7.99-8.05(m, 2H), 8.10(s, 1H) (400MHz, CD₃CN) δ ppm 1.36(d, J=6.1Hz, 3H), 4.72-4.79(m, 1H), 5.30(s, 2H), 7.07(d, J=7.6Hz, 1H), 7.23(t, J=7.6Hz, 1H), 7.33-7.37(m, 1H), 7.36(t, J=8.1Hz, 1H), 7.46-7.48(m, 1H), 8.01(d, J=8.1Hz, 1H), 8.06(dd, J=1.1, 8.1Hz, 1H), 8.06(s, 1H), 8.55(br.s, 1H) |
| 12 | 2-(7-Nitro-1H-benzimidazol-1-yl)-N-[4-(trifluoromethyl)phenyl]acetamide | 364.3 | 365.0 | (400MHz, DMSO-d6) δ ppm 5.44(s, 2H), 7.43(t, J=8.1Hz, 1H), 7.68(d, 8.4Hz, 2H), 7.73(d, J=8.4Hz, 2H), 8.03(d, J=8.1Hz, 1H), 8.15(d, J=8.1Hz, 1H), 8.45(s, 1H), 10.8(br.s, 1H) |
| 13 | N-(3-Chlorophenyl)-2-(7-nitro-1H-benzimidazol-1-yl)acetamide | 330.7 | no | (400MHz, CD₃CN) δ ppm 5.32(s, 2H), 7.10-7.14(m, 1H), 7.28-7.33(m, 1H), 7.36-7.40(m, 1H), 7.41(t, J=8.1Hz, 1H), 7.52-7.65(m, 1H), 8.04(d, J=8.1Hz, 1H), 8.09(dd, J=1.0, 8.1Hz, 1H), 8.11(s, 1H), 8.78(br.s, 1H) |
| 14 | N-Hexyl-2-(7-nitro-1H-benzimidazol-1-yl)acetamide | 304.4 | 305.1 | (400MHz, CD₃CN) δ ppm 0.88(t, J=7.1Hz, 3H), 1.23-1.33(m, 6H), 1.38-1.46(m, 2H), 3.08-3.14(m, 2H), 5.09(s, 2H), 6.58(br.s, 1H), 7.36(t, J=8.1Hz, 1H), 7.98(dd, J=1.0, 8.1Hz, 1H), 8.04(s, 1H), 8.05(dd, J=1.0, 8.1Hz, 1H) |
| 15 | N-(3,4-Difluorophenyl)-2(7-nitro-1H-benzimidazol-1-yl)acetamide | 332.3 | 333.1 | (400MHz, CD₃CN) δ ppm 5.29(s, 2H), 7.07-7.17(m, 2H), 7.37(t, J=8.1Hz, 1H), 7.51-7.58(m, 1H), 8.02(d, J=8.1Hz, 1H), 8.07(s, 1H), 8.08(d, J=8.1Hz, 1H), 8.73(br.s, 1H) |
| 16 | N-(4-Cyanophenyl)-2-(7-nitro-1H-benzimidazol-1-yl)acetamide | 321.3 | 320.2 | (400MHz, CD₃CN) δ ppm 5.33(s, 2H), 7.38(t, J=8.1Hz, 1H), 7.59(d, J=8.9Hz, 2H), 7.65(d, J=8.7Hz, 2H), 8.03(d, J=8.1Hz, 1H), 8.07(s, 1H), 8.08(d, J=8.0Hz, 1H), 8.96(br.s, 1H) |
| 17 | N-(2,3-Dihydro-1,4-benzodioxin-6-yl)-2-(7-nitro-1H-benzimidazol-1-yl)acetamide | 354.3 | no | (400MHz, DMSO-d6) δ ppm 4.15-4.23(m, 4H), 5.34(s, 2H), 6.77(d, J=8.6Hz, 1H), 6.87(dd, J=2.5, 8.6Hz, 1H), 7.10(d, J=2.5Hz, 1H), 7.41(t, J=8.1Hz, 1H), 8.01(dd, J=1.0, 8.1Hz, 1H), 8.12(dd, J=1.0, 7.6Hz, 1H), 8.44(s, 1H), 10.2(br.s, 1H) |
| 18 | N-(2-Bromobenzyl)-2-(7-nitro-1H-benzimidazol-1-yl)acetamide | 389.2 | 391.0 | (400MHz, CD₃CN) δ ppm 4.40(d, J=6.1Hz, 2H), 5.21(s, 2H), 6.99-7.06(m, 1H), 7.12-7.18(m, 1H), 7.28-7.38(m, 3H), 7.53(d, J=7.6Hz, 1H), 7.99(d, J=8.1Hz, 1H), 8.04(d, J=8.1Hz, 1H), 8.05(s, 1H) |
| 19 | 2-(7-Nitro-1H-benzimidazol-1-yl)-N-[3-(trifluoromethyl)benzyl]acetamide | 378.3 | 379.0 | (400MHz, CD₃CN) δ ppm 4.41(d, J=6.1Hz, 2H), 5.19(s, 2H), 7.07-7.14(m, 1H), 7.35(t, J=8.1Hz, 1H), 7.44-7.57(m, 4H), 7.99(dd, J=1.0, |

-continued

| Example number | Name | MW calcd | MW found [M + 1] or [M − 1] | ¹H NMR |
|---|---|---|---|---|
| 20 | N-(4-Methylpyridin-2-yl)-2-(7-nitro-1H-benzimidazol-1-yl)acetamide | 311.3 | 312.1 | (400MHz, CD₃CN) δ ppm 2.28(s, 3H), 5.39(s, 2H), 6.90(d, J=5.1Hz, 1H), 7.38(t, J=8.1Hz, 1H), 7.75-7.82(m, 1H), 8.03(d, J=8.1Hz, 1H), 8.04(dd, J=1.0, 8.1Hz, 1H), 8.05(s, 1H), 8.08(d, J=8.1Hz, 1H), 8.08(s, 1H), 8.13(d, J=5.1Hz, 1H), 8.87(br.s, 1H) |
| 21 | N-(3-Cyanophenyl)-2-(7-nitro-1H-benzimidazol-1-yl)acetamide | 321.3 | 322.1 | (400MHz, CDCl₃/CD₃OD) δ ppm 5.28(s, 2H), 7.25-7.35(m, 3H), 7.67-7.72(m, 1H), 7.79(br.s, 1H), 8.02(s, 1H), 7.96-8.06(m, 2H) |
| 22 | N-(3,5-Dimethoxyphenyl)-2-(7-nitro-1H-benzimidazol-1-yl)acetamide | 356.3 | 357.0 | (400MHz, CDCl₃) δ ppm 3.73(s, 6H), 5.26(s, 2H), 6.21-6.24(m, 1H), 6.66-6.70(m, 2H), 7.37(t, J=8.1Hz, 1H), 7.69(br.s, 1H), 8.01(s, 1H), 8.09(d, J=8.1Hz, 1H), 8.13(d, J=8.1Hz, 1H) |
| 23 | N-(3-Methoxyphenyl)-2-(7-nitro-1H-benzimidazol-1-yl)acetamide | 326.3 | 327.2 | (400MHz, DMSO-d6) δ ppm 3.69(s, 3H), 5.39(s, 2H), 6.62-6.66(m, 1H), 7.02-7.06(m, 1H), 7.18-7.23(m, 2H), 7.42(t, J=8.1Hz, 1H), 8.02(d, 8.1Hz, 1H), 8.13(dd, J=1.0, 8.1Hz, 1H), 8.45(s, 1H), 10.4(br.s, 1H) |
| 24 | N-(3-Ethoxyphenyl)-2-(7-nitro-1H-benzimidazol-1-yl)acetamide | 340.3 | 341.2 | (400MHz, DMSO-d6) δ ppm 1.28(t, J=6.8Hz, 3H) 3.95(q, J=6.7Hz, 2H) 5.38(s, 2H) 6.62(dd, J=7.8, 2.3Hz, 1H) 7.01(m, 1H) 7.19(m, 2H) 7.42(t, J=7.8Hz, 1H) 8.02(dd, J=8.1, 1.0Hz, 1H) 8.14(m, 1H) 8.45(s, 1H) 10.37(s, 1H) |
| 25 | N-(3,4-Dimethoxyphenyl)-2-(7-nitro-1H-benzimidazol-1-yl)acetamide | 356.3 | 357.2 | (400MHz, DMSO-d6) δ ppm 3.68(s, 3H) 3.70(s, 3H) 5.36(s, 2H) 6.88(d, J=9.1Hz, 1H) 6.99(dd, J=8.8, 2.3Hz, 1H) 7.19(d, J=2.5Hz, 1H) 7.42(t, J=7.8Hz, 1H) 8.01(d, J=7.6Hz, 1H) 8.13(m, 1H) 8.45(s, 1H) 10.24(s, 1H) |
| 26 | 2-(7-Nitro-1H-benzimidazol-1-yl)-N-(3,4,5-trimethoxyphenyl)acetamide | 386.4 | 387.2 | (400MHz, DMSO-d6) δ ppm 3.60(s, 3H) 3.70(s, 6H) 5.37(s, 2H) 6.88(s, 2H) 7.42(t, J=8.1Hz, 1H) 8.02(d, J=8.1Hz, 1H) 8.13(dd, J=8.1, 1.0Hz, 1H) 8.45(s, 1H) 10.35(s, 1H) |
| 27 | 2-(7-Nitro-1H-benzimidazol-1-yl)-N-[3-(trifluoromethoxy)phenyl]acetamide | 380.3 | 381.1 | (400MHz, DMSO-d6) δ ppm 5.42(s, 2H) 7.05(m, 1H) 7.43(m, 3H) 7.66(s, 1H) 8.03(d, J=8.1Hz, 1H) 8.15(m, 1H) 8.44(s, 1H) 10.71(s, 1H) |
| 28 | 2-(7-Nitro-1H-benzimidazol-1-yl)-N-(3-phenoxyphenyl)acetamide | 388.4 | 389.2 | (400MHz, DMSO-d6) δ ppm 5.36(s, 1H) 6.71(m, 1H) 7.02(m, 2H) 7.13(t, J=7.3Hz, 1H) 7.21(t, J=2.0Hz, 1H) 7.28(m, 2H) 7.39(m, 3H) 8.01(d, J=7.6Hz, 1H) 8.12(dd, J=8.1, 1.0Hz, 1H) 8.42(s, 1H) 10.47(s, 1H) |
| 29 | N-(4-Butylphenyl)-2-(7-nitro-1H-benzimidazol-1-yl)acetamide | 352.4 | 353.2 | (400MHz, DMSO-d6) δ ppm 0.87(t, J=7.3Hz, 3H) 1.27(m, 2H) 1.50(m, 2H) 2.52(m, 2H) 5.37(s, 2H) 7.10(d, J=8.6Hz, 2H) 7.41(m, 3H) |

-continued

| Example number | Name | MW calcd | MW found [M + 1] or [M − 1] | ¹H NMR |
|---|---|---|---|---|
| 30 | N-(2-Fluoro-4-iodophenyl)-2-(7-nitro-1H-benzimidazol-1-yl)acetamide | 440.2 | 441.0 | (400MHz, DMSO-d6) δ ppm 5.46(s, 2H) 7.41(t, J=8.1Hz, 1H) 7.49(m, 1H) 7.59(t, J=8.3Hz, 1H) 7.70(dd, J=10.1, 2.0Hz, 1H) 8.02(dd, J=8.1, 1.0Hz, 1H) 8.13(dd, J=8.1, 1.0Hz, 1H) 8.45(s, 1H) 10.35(s, 1H) |
| 31 | 2-(7-Nitro-1H-benzimidazol-1-yl)-N-[2-(trifluoromethyl)benzyl]acetamide | 378.3 | 379.2 | (400MHz, DMSO-d6) δ ppm 4.44(d, J=5.6Hz, 2H) 5.32(s, 2H) 7.40(t, J=8.1Hz, 1H) 7.48(d, J=7.6Hz, 1H) 7.55(d, J=8.1Hz, 1H) 7.68(m, 2H) 8.00(d, J=8.1Hz, 1H) 8.11(dd, J=8.1, 1.0Hz, 1H) 8.44(s, 1H) 8.86(t, J=5.8Hz, 1H) |
| 32 | N-(4-Methoxyphenyl)-2-(7-nitro-1H-benzimidazol-1-yl)acetamide | 326.3 | 325 | (400MHz, DMSO-D6) δ ppm 3.71(s, 3H), 5.37(s, 2H), 6.88(d, J=9.1Hz, 2H), 7.44-7.40(m, 3H), 8.02(d, J=7.8Hz, 1H), 8.14(d, J=7.8Hz, 1H), 8.45(s, 1H), 10.24(s, 1H) |
| 33 | 2-(7-Nitro-1H-benzimidazol-1-yl)-N-[2-(trifluoromethoxy)phenyl]acetamide | 380.3 | 381 | (400MHz, DMSO-D6) δ ppm 5.49(s, 2H), 7.27-7.23(m, 1H), 7.37-7.33(m, 1H), 7.45-7.41(m, 2H), 7.80(dd, J=8.1, 1.5Hz, 1H), 8.03(dd, J=8.1, 0.8Hz, 1H), 8.14(dd, J=8.0, 0.9Hz, 1H), 8.50(s, 1H), 10.25(s, 1H) |
| 34 | 2-(7-Nitro-1H-benzimidazol-1-yl)-N-(2-phenoxyphenyl)acetamide | 388.4 | 389 | (400MHz, DMSO-D6) δ ppm 5.45(s, 2H), 6.87-6.85(m, 1H), 7.09-7.04(m, 4H), 7.18(t, J=7.4Hz, 1H), 7.44-7.40(m, 3H), 7.90-7.87(m, 1H), 8.02(d, J=7.3Hz, 1H), 8.13(dd, J=8.0, 0.9Hz, 1H), 8.45(s, 1H), 10.07(s, 1H) |
| 35 | N-(4-Bromo-2-fluorophenyl)-2-(7-nitro-1H-benzimidazol-1-yl)acetamide | 393.2 | 391 | (400MHz, DMSO-D6) δ ppm 5.48(s, 2H), 7.37(d, J=8.8Hz, 1H), 7.43(t, J=8.1Hz, 1H), 7.63(dd, J=10.5, 2.2Hz, 1H), 7.75(t, J=8.7Hz, 1H), 8.03(d, J=7.6Hz, 1H), 8.14(dd, J=8.1, 0.8Hz, 1H), 8.46(s, 1H) 10.39(s, 1H) |
| 36 | N-[3-(Methylsulfonyl)phenyl]-2-(7-nitro-1H-benzimidazol-1-yl)acetamide | 374.4 | 373 | (400MHz, DMSO-D6) δ ppm 3.18(s, 3H), 5.45(s, 2H), 7.44(t, J=8.1Hz, 1H), 7.64-7.59(m, 2H), 7.83-7.80(m, 1H), 8.05(dd, J=8.1, 1.0Hz, 1H), 8.17-8.15(m, 2H), 8.47(s, 1H), 10.85(s, 1H) |
| 37 | N-[4-(Methylsulfonyl)phenyl]-2-(7-nitro-1H-benzimidazol-1-yl)acetamide | 374.4 | 373 | (400MHz, DMSO-D6) δ ppm 3.16(s, 3H), 5.46(s, 2H), 7.44(t, J=8.1Hz, 1H), 7.77(d, J=8.8Hz, 2H), 7.87(d, J=8.8Hz, 2H), 8.04(d, J=7.3Hz, 1H), 8.16(dd, J=8.1, 1.0Hz, 1H), 8.46(s, 1H), 10.90(s, 1H) |
| 38 | N-(3,5-Dimethylphenyl)-2-(7-nitro-1H-benzimidazol-1-yl)acetamide | 324.3 | 323 | (400MHz, DMSO-D6) δ ppm 2.21(s, 6H), 5.38(s, 2H), 6.71(s, 1H), 7.13(s, 2H), 7.43(t, J=8.1Hz, 1H), 8.03(dd, J=8.1, 0.8Hz, 1H), 8.14(dd, J=7.8, 1.0Hz, 1H), 8.46(s, 1H), 10.24(s, 1H) |

-continued

| Example number | Name | MW calcd | MW found [M + 1] or [M − 1] | ¹H NMR |
|---|---|---|---|---|
| 39 | 2-(7-Nitro-1H-benzimidazol-1-yl)-N-[4-(trifluoromethyl)benzyl]acetamide | 378.3 | 377 | (400MHz, DMSO-D6) δ ppm 4.37(d, J=5.8Hz, 2H) 5.29(s, 2H), 7.41(t, J=8.0Hz, 1H), 7.48(d, J=7.8Hz, 2H), 7.68(d, J=8.1Hz, 2H), 8.01(d, J=8.1Hz, 1H), 8.12(d, J=8.1Hz, 1H), 8.43(s, 1H), 8.87(t, J=5.7Hz, 1H) |
| 40 | N-(4-tert-Butylbenzyl)-2-(7-nitro-1H-benzimidazol-1-yl)acetamide | 366.4 | 367 | (400MHz, CD₃OD) δ ppm 1.30(s, 9H), 4.33(s, 2H), 5.33(s, 2H), 7.21(d, J=8.34Hz, 2H), 7.35(d, J=8.34Hz, 2H), 7.44(t, J=8.08Hz, 1H), 8.04-8.09(m, 2H), 8.31(s, 1H) |
| 41 | N-(2,3-dihydro-1H-inden-5-yl)-2-(7-nitro-1H-benzimidazol-1-yl)acetamide | 336.4 | 337 | (400MHz, CD₃OD) δ ppm 2.00-2.10(m, 2H), 2.80-2.88(m, 4H), 5.43(s, 2H), 7.10-7.20(m, 2H), 7.35(s, 1H), 7.44(t, J=8.08Hz, 1H), 8.05-8.10(m, 2H), 8.35(s, 1H) |
| 42 | 2-(7-Nitro-1H-benzimidazol-1-yl)-N-[4-(trifluoromethoxy)benzyl]acetamide | 394.3 | 395 | (400MHz, CD₃OD) δ ppm 4.39(s, 2H), 5.35(s, 2H), 7.21(d, J=7.83Hz, 2H), 7.39(d, J=8.59Hz, 2H), 7.44(t, J=8.08Hz, 1H), 8.04-8.09(m, 2H), 8.32(s, 1H) |
| 43 | N-(4-Isopropyl-phenyl)-2-(7-nitro-1H-benzoimidazol-1-yl)-acetamide N-(4-Isopropylphenyl)-2-(7-nitro-1H-benzimidazol-1-yl)acetamide | 338.4 | 339 | (400MHz, CD₃OD) δ ppm 1.21(d, J=6.82Hz, 6H), 2.80-2.91(m, J=6.86Hz, 1H), 5.44(s, 2H), 7.16(d, J=8.59Hz, 2H), 7.38(d, J=8.59Hz, 2H), 7.44(t, J=8.08Hz, 1H), 8.08(d, J=8.08Hz, 2H), 8.35(s, 1H) |
| 44 | N-(3,4-Dimethylphenyl)-2-(7-nitro-1H-benzimidazol-1-yl)acetamide | 324.3 | 325 | (400MHz, CD₃OD) δ ppm 2.20(s, 3H), 2.22(s, 3H), 5.49(s, 2H), 7.04(d, J=8.34Hz, 1H), 7.19(d, J=8.08Hz, 1H), 7.25(s, 1H), 7.56(t, J=8.08Hz, 1H), 8.10-8.19(m, 2H), 8.73(s, 1H) |
| 45 | N-1,3-Benzodioxol-5-yl-2-(7-nitro-1H-benzimidazol-1-yl)acetamide | 340.3 | 341 | (400MHz, CD₃OD) δ ppm 5.42(s, 2H), 5.91(s, 2H), 6.74(d, J=8.34Hz, 1H), 6.85(dd, J=8.34, 2.02Hz, 1H), 7.09(d, J=2.02Hz, 1H), 7.45(t, J=8.08Hz, 1H), 8.08(d, J=8.08, 2H), 8.34(s, 1H) |
| 46 | N-(3-Bromo-4-trifluoromethoxy-phenyl)-2-(7-nitro-1H-benzoimidazol-1-yl)-acetamide N-[3-Bromo-4-(trifluoromethoxy)phenyl]-2-(7-nitro-1H-benzimidazol-1-yl)acetamide | 459.2 | 460 | (400MHz, CD₃OD) δ ppm 5.46(s, 2H), 7.33-.37(m, 1H), 7.46(t, J=8.08Hz, 1H), 7.55(dd, J=9.09, 2.53Hz, 1H), 7.97(d, J=2.53Hz, 1H), 8.07-8.11(m, 2H), 8.35(s, 1H), |
| 47 | N-(3-Fluoro-2-methoxyphenyl)-2-(7-nitro1H-benzimidazol-1-yl)acetamide | 344.3 | 345 | (400MHz, CD₃OD) δ ppm 3.96(d, J=1.52Hz, 3H), 5.55(s, 2H), 6.91-7.01(m, 2H), 7.45(t, J=8.08Hz, 1H), 7.66(d, J=8.34Hz, 1H), 8.09(d, J=8.08Hz, 2H), 8.37(s, 1H) |
| 48 | N-(3,5-Dimethoxyphenyl)-2-(7-nitro-1H-benzimidazol-1-yl)propanamide | 370.4 | 371.1 | (400MHz, CD₃CN) δ ppm 1.96(d, 3H) 3.73(s, 6H) 5.57(q, J=7.2Hz, 1H) 6.25(t, J=2.3Hz, 1H) 6.75(d, J=2.0Hz, 2H) 7.39(t, J=8.1Hz, 1H) 7.96(m, 1H) 8.07(dd, J=8.1, 1.0Hz, 1H) 8.40(s, 1H) 8.57(s, 1H) |

-continued

| Example number | Name | MW calcd | MW found [M + 1] or [M − 1] | ¹H NMR |
|---|---|---|---|---|
| 49 | N-(3-Ethoxyphenyl)-2-(7-nitro-1H-benzimidazol-1-yl)propanamide | 354.4 | 355.1 | (400MHz, CD$_3$CN) δ ppm 1.33(t, J=6.8Hz, 3H) 1.96(d, J=7.1Hz, 3H) 3.99(q, J=7.1Hz, 2H) 5.58(q, J=7.2Hz, 1H) 6.65(m, 1H) 7.03(dd, J=8.1, 1.5Hz, 1H) 7.19(m, 2H) 7.38(t, J=8.1Hz, 1H) 7.95(dd, J=8.1, 1.0Hz, 1H) 8.07(dd, J=8.1, 1.0Hz, 1H) 8.41(s, 1H) 8.61(s, 1H) |
| 50 | 2-(7-Nitro-1H-benzimidazol-1-yl)-N-[3-(trifluoromethyl)phenyl]propanamide | 378.3 | 379.1 | (400MHz, CD$_3$CN) δ ppm 1.98(d, J=7.6Hz, 3H) 5.63(q, J=7.2Hz, 1H) 7.40(m, J=7.92, 7.92, 7.92Hz, 2H) 7.51(t, J=8.1Hz, 1H) 7.71(d, J=8.1Hz, 1H) 7.96(m, 2H) 8.08(dd, J=8.1, 1.0Hz, 1H) 8.42(s, 1H) 8.89(s, 1H) |
| 51 | 2-(7-Nitro-1H-benzimidazol-1-yl)-N-[3-(trifluoromethyl)phenyl]acetamide | 364.1 | 365.0 | (400MHz, CD$_3$CN) δ ppm 5.43(s, 2H), 7.43(m, 2H), 7.56(t, J=8.1Hz, 1H), 7.71(d, J=8.1Hz, 1H), 7.98(s, 1H), 8.03(dd, J=8.1, 0.76Hz, 1H), 8.15(dd, J=7.8, 1.0Hz, 1H), 8.45(s, 1H), 10.76(s, 1H). |
| 52 | 2-(7-Bromo-1H-benzimidazol-1-yl)-N-(3,5-dimethoxyphenyl)acetamide | 390.2 | 390.0 | (400MHz, DMSO-D6) δ ppm 3.68(s, 6H) 5.38(s, 2H) 6.22(t, J=2.3Hz, 1H) 6.81(d, J=2.0Hz, 2H) 7.14(t, J=8.1Hz, 1H) 7.41(d, J=7.6Hz, 1H) 7.69(d, J=7.6Hz, 1H) 8.26(s, 1H) 10.40(s, 1H). |
| 53 | 2-(7-Bromo-1H-benzimidazol-1-yl)-N-(3-methoxyphenyl)acetamide | 360.2 | 360.0 | (400MHz, DMSO-D6) δ ppm 5.44(m, 2H) 7.15(m, 1H) 7.42(m, 2H) 7.57(m, 1H) 7.70(dd, J=8.1, 0.9Hz, 1H) 7.75(m, J=8.6, 1.2Hz, 1H) 8.04(s, 1H) 8.27(m, 1H) 10.81(s, 1H) |
| 54 | 2-(7-Bromo-1H-benzimidazol-1-yl)-N-[3-(trifluoromethyl)phenyl]acetamide | 398.2 | 398.0 | (400MHz, DMSO-D6) δ ppm 3.69(s, 3H) 5.40(s, 2H) 6.64(ddd, J=8.3, 2.5, 0.9Hz, 1H) 7.08(ddd, J=8.1, 1.9, 0.8Hz, 1H) 7.14(m, 1H) 7.21(t, J=8.1Hz, 1H) 7.26(m, 1H) 7.41(dd, J=7.7, 0.7Hz, 1H) 7.69(dd, J=8.0, 1.0Hz, 1H) 8.27(s, 1H) 10.43(s, 1H) |
| 55 | 2-(7-Chloro-1H-benzimidazol-1-yl)-N-(3,5-dimethoxyphenyl)acetamide | 345.8 | 346.1 | (400MHz, CD$_3$CN) δ ppm 3.73(s, 6H), 5.29(s, 2H), 6.26(t, J=2.2Hz, 1H), 6.78(d, J=2.1Hz, 2H), 7.19-7.27(m, 2H), 7.66(dd, J=1.2, 7.6Hz, 1H), 7.97(s, 1H), 8.64(br.s, 1H) |
| 56 | 2-(7-Chloro-1H-benzimidazol-1-yl)-N-[3-(trifluoromethyl)phenyl]acetamide | 353.7 | 354.0 | (400MHz, CD$_3$CN) δ ppm 5.42(s, 2H), 7.15-7.30(m, 2H), 7.41(d, J=7.9Hz, 1H), 7.56(t, J=8.1Hz, 1H), 7.73(d, J=8.1Hz, 1H), 7.80(d, J=7.9Hz, 1H), 7.98(s, 1H), 8.02(s, 1H) 8.92(s, 1H) |
| 57 | 2-(7-Chloro-1H-benzimidazol-1-yl)-N-(4-methylphenyl)acetamide | 299.8 | 300.1 | (400MHz, CD$_3$CN) δ ppm 2.27(s, 3H), 5.31(s, 2H), 7.12(d, J=8.2Hz, 2H), 7.19-7.27(m, 2H), 7.46(d, J=8.2Hz, 2H), 7.66(dd, J=1.2, 7.6Hz, 1H), 7.97(s, 1H), 8.64(br.s, 1H) |
| 58 | 2-(7-chloro-1H-benzimidazol-1-yl)-N-(2,3-dihydro-1H-inden-5-yl)acetamide | 325.8 | 325 | (400MHz, DMSO-D6) δ 10.29(s, 1H), 8.27(s, 1H), 7.66(dd, J=7.8, 1.0Hz, 1H), 7.47(s, 1H), |

-continued

| Example number | Name | MW calcd | MW found [M + 1] or [M − 1] | ¹H NMR |
|---|---|---|---|---|
| 59 | 2-(7-Methyl-1H-benzimidazol-1-yl)-N-(4-methylphenyl)acetamide | 279.3 | 278 | 7.28-7.25(m, 2H), 7.20(t, J=7.8Hz, 1H), 7.14(d, J=8.0Hz, 1H), 5.37(s, 2H), 2.83-2.77(m, 4H), 2.03-1.95(m, 2H) (400MHz, DMSO-D6) δ ppm 2.25(s, 3H), 2.55(s, 3H), 5.29(s, 2H), 6.95(d, J=7.3Hz, 1H), 7.07(t, J=7.7Hz, 1H), 7.12(d, J=8.3Hz, 2H), 7.45-7.49(m, 3H), 8.11(s, 1H), 10.34(s, 1H) |
| 60 | N-(3,5-Dimethoxyphenyl)-2-(7-methyl-1H-benzimidazol-1-yl)acetamide | 325.4 | 326 | (400MHz, DMSO-D6) δ ppm 2.54(s, 3H), 3.70(s, 6H), 5.29(s, 2H), 6.24(t, J=2.0Hz, 1H), 6.83(d, J=2.0Hz, 2H), 6.95(d, J=7.3Hz, 1H), 7.07(t, J=7.6Hz, 1H), 7.48(d, J=8.1Hz, 1H), 8.11(s, 1H), 10.42(s, 1H) |
| 61 | 2-(7-Methyl-1H-benzimidazol-1-yl)-N-[3-(trifluoromethyl)phenyl]acetamide | 333.3 | 334 | (400MHz, DMSO-D6) δ ppm 2.55(s, 3H), 5.36(s, 2H), 6.96(d, J=7.3Hz, 1H), 7.08(t, J=7.7Hz, 1H), 744(d, J=7.8Hz, 1H), 7.49(d, J=8.1Hz, 1H), 7.59(t, J=8.1Hz, 1H), 7.79(d, J=8.1Hz, 1H), 8.07(s, 1H), 8.13(s, 1H), 10.81(s, 1H) |
| 62 | N-(2,3-Dihydro-1H-inden-5-yl)-2-(7-methyl-1H-benzimidazol-1-yl)acetamide | 305.4 | 304 | (400MHz, DMSO-D6) δ 10.31(s, 1H), 8.11(s, 1H), 7.48-7.47(m, 2H), 7.28(dd, J=8.2, 2.0Hz, 1H), 7.15(d, J=8.0Hz, 1H), 7.07(t, J=7.4Hz, 1H), 6.95(d, J=7.2Hz, 1H), 5.28(s, 2H), 2.83-2.78(m, 4H), 2.54(s, 3H), 2.03-1.95(m, 2H) |
| 63 | Methyl 1-{2-[(3,4-dimethylphenyl)amino]-2-oxoethyl}-1H-benzimidazole-7-carboxylate | 337.4 | 338 | (400MHz, CD₃OD) δ ppm 2.19(s, 3H), 2.21(s, 3H), 3.81(s, 3H), 5.48(s, 2H), 7.03(d, J=8.01Hz, 1H), 7.22(dd, J=8.10, 2.25Hz, 1H), 7.26(d, J=1.76Hz, 1H), 7.34(t, J=7.81Hz, 1H), 7.86(dd, J=7.62, 1.17Hz, 1H), 7.91(dd, J=8.01, 1.17Hz, 1H), 8.22(s, 1H) |
| 64 | Methyl 1-[2-(2,3-dihydro-1H-inden-5-ylamino)-2-oxoethyl]-1H-benzimidazole-7-carboxylate | 349.4 | 350 | (400MHz, CD₃OD) δ ppm 2.00-2.08(m, J=7.37Hz, 2H), 2.80-2.87(m, 4H), 5.48(s, 2H), 3.81(s, 3H), 7.11(d, J=8.00, 1H), 7.20(dd, J=8.20, 1.95Hz, 1H), 7.34(t, J=7.91Hz, 1H), 7.38(s, 1H), 7.86(dd, J=7.71, 1.07Hz, 1H), 7.91(dd, 1=8.10, 1.07Hz, 1H), 8.22(s, 1H) |
| 65 | Methyl 1-{2-[(4-tert-butylbenzyl)amino]-2-oxoethyl}-1H-benzimidazole-7-carboxylate | 379.5 | 380 | (400MHz, CD₃OD) δ ppm 1.29(s, 9H), 4.31(s, 2H), 3.75(s, 3H), 5.37(s, 2H), 7.21(d, J=8.59Hz, 2H), 7.30-7.36(m, 3H), 7.84-7.92(m, 2H), 8.19(s, 1H) |
| 66 | Methyl 1-(2-{[3-methoxy-5-(trifluoromethyl)phenyl]amino}-2-oxoethyl)-1H-benzimidazole-7-carboxylate | 407.4 | 408 | (400MHz, CD₃OD) δ ppm 3.81(s, 3H), 3.81(s, 3H), 5.53(s, 2H), 6.90(s, 1H), 7.36(t, J=7.91Hz, 1H), 7.47(s, 1H), 7.45(t, J=1.95Hz, 1H), 7.87-7.95(m, 2H), 8.23(s, 1H) |
| 67 | Methyl 1-{2-[(3,5-dimethoxyphenyl)amino]-2-oxoethyl}-1H-benzimidazole-7- | 369.4 | | (400MHz, DMSO-d6) δ ppm 3.68(s, 6H), 3.74(s, 3H), 5.39(s, 2H), 6.21(t, J=2.0Hz, 1H), 6.77(d, J=2.0Hz, 2H), 7.30(t, |

-continued

| Example number | Name | MW calcd | MW found [M + 1] or [M − 1] | ¹H NMR |
|---|---|---|---|---|
| | carboxylate | | | J=7.8Hz, 1H), 7.72(d, J=7.6Hz, 1H), 7.93(dd, J=1.0, 8.1Hz, 1H), 8.29(s, 1H), 10.28(s, 1H) |
| 68 | N-(3,5-Dimethoxyphenyl)-2-{7-[(dimethylamino)sulfonyl]-1H-benzimidazol-1-yl}acetamide | 418.5 | 417 | (400MHz, CDCl₃) δ ppm 2.89(s, 6H), 3.74(s, 6H), 5.42(s, 2H), 6.23(s, 1H), 6.72(d, J=2Hz, 2H), 7.39(t, J=8.0Hz, 1H), 7.70(d, J=7.6Hz, 1H), 8.05(broad s, 1H), 8.09(d, J=7.8Hz, 1H), 8.17(s, 1H) |
| 69 | 2-{7-[(Dimethylamino)sulfonyl]-1H-benzimidazol-1-yl}-N-[3-(trifluoromethyl)phenyl]acetamide | 426.4 | 427 | (400MHz, DMSO-D6) δ ppm 2.69(s, 6H), 5.59(s, 2H), 7.45-7.40(m, 2H), 7.57(t, J=8.0Hz, 1H), 7.73-7.69(m, 2H), 8.08-8.05(m, 2H), 8.37(s, 1H), 10.70(s, 1H) |
| 70 | N-(3,5-Dimethoxyphenyl)-2-[7-(propylsulfonyl)-1H-benzimidazol-1-yl]acetamide | 417.5 | 416 | (400MHz, DMSO-D6) δ ppm 0.77(t, J=7.4Hz, 3H), 1.62-1.52(m, 2H), 3.29-3.24(m, 2H), 3.69(s, 6H), 5.60(s, 2H), 6.23(t, J=2.2Hz, 1H), 6.82(d, J=2.3Hz, 2H), 7.47(t, J=7.8Hz, 1H), 7.82(dd, J=7.8, 0.8Hz, 1H), 8.11(dd, J=8.1, 1.0Hz, 1H), 8.41(s, 1H), 10.49(s, 1H) |
| 71 | 2-[7-(Propylsulfonyl)-1H-benzimidazol-1-yl]-N-[3-(trifluoromethyl)phenyl]acetamide | 425.4 | 426 | (400MHz, DMSO-D6) δ ppm 0.74(t, J=7.4Hz, 3H), 1.60-1.50(m, 2H), 3.29-3.24(m, 2H), 5.64(s, 2H), 7.43(d, J=7.8Hz, 1H), 7.48(t, J=7.8Hz, 1H), 7.58(t, J=8.0Hz, 1H), 7.73(d, J=8.6Hz, 1H), 7.82(d, J=7.8Hz, 1H), 8.09(s, 1H), 8.12(dd, J=8.1, 1.0Hz, 1H), 8.42(s, 1H), 10.88(s, 1H) |
| 72 | N-[3-Methoxy-5-(trifluoromethyl)phenyl]-2-[7-(methylsulfonyl)-1H-benzimidazol-1-yl]acetamide | 427.4 | 426 | (400MHz, DMSO-D6) δ 10.77(s, 1H), 8.42(s, 1H), 8.10(d, J=7.3Hz, 1H), 7.86(d, J=7.6Hz, 1H), 7.55(s, 1H), 7.47(t, J=8.0Hz, 1H), 7.42(s, 1H), 6.95(s, 1H), 5.60(s, 2H), 3.80(s, 3H), 3.30(s, 3H) |
| 73 | N-(3,5-Dimethoxyphenyl)-2-[7-(trifluoromethyl)-1H-benzimidazol-1-yl]acetamide | 379.3 | 378 | (400MHz, DMSO-D6) δ ppm 3.69(s, 6H), 5.28(s, 2H), 6.22(t, J=2.3Hz, 1H), 6.78(d, J=2.3Hz, 2H), 7.41(t, J=7.8Hz, 1H), 7.65(d, J=7.6Hz, 1H), 8.04(d, J=8.1Hz, 1H), 8.37(s, 1H), 10.41(s, 1H) |
| 74 | N-(3,4-Dimethylphenyl)-2-[7-(trifluoromethyl)-1H-benzimidazol-1-yl]acetamide | 347.3 | 348 | (400MHz, DMSO-D6) δ 10.26(s, 1H), 8.37(s, 1H), 8.04(d, J=8.1Hz, 1H), 7.65(d, J=7.8Hz, 1H), 7.41(t, J=7.8Hz, 1H), 7.31(d, J=1.8Hz, 1H), 7.24(dd, J=8.3, 2.0Hz, 1H), 7.04(d, J=8.1Hz, 1H), 5.27(s, 2H), 2.16(s, 3H), 2.15(s, 3H) |
| 75 | N-(4-tert-Butylbenzyl)-2-[7-(trifluoromethyl)-1H-benzimidazol-1-yl]acetamide | 389.4 | 388 | (400MHz, DMSO-D6) δ 8.70(broad t, J=5.7Hz, 1H), 8.34(s, 1H), 8.02(d, J=8.1Hz, 1H), 7.64(d, J=7.6Hz, 1H), 7.39(t, J=7.8Hz, 1H), 7.35(d, J=8.3Hz, 2H), 7.19(d, J=8.3Hz, 2H), 5.12(s, 2H), 4.25(d, J=5.6Hz, 2H), 1.27(s, 9H) |

-continued

| Example number | Name | MW calcd | MW found [M + 1] or [M − 1] | ¹H NMR |
|---|---|---|---|---|
| 76 | N-(2,3-Dihydro-1H-inden-5-yl)-2-[7-(trifluoromethyl)-1H-benzimidazol-1-yl]acetamide | 359.4 | 360 | (400MHz, DMSO-D6) δ 10.29(s, 1H), 8.37(s, 1H), 8.04(d, J=8.1Hz, 1H), 7.65(d, J=7.8Hz, 1H), 7.43-7.39(m, 2H), 7.23(dd, J=8.0, 1.6Hz, 1H), 7.13(d, J=8.1Hz, 1H), 5.28(s, 2H), 2.82-2.77(m, 4H), 2.02-1.95(m, 2H) |
| 77 | 2-(7-Cyano-1H-benzimidazol-1-yl)-N-(2,3-dihydro-1H-inden-5-yl)acetamide | 316.4 | 317.1 | (400MHz, DMSO-D6) δ ppm: 1.79(m, 2H), 2.60(q, J=7.3Hz, 4H), 5.19(s, 2H), 6.94(d, J=8.1Hz, 1H), 7.05(dd, J=8.1, 2.0Hz, 1H), 7.17(t, J=8.0Hz, 1H), 7.27(bs, 1H), 7.54(dd, J=7.6, 1.0Hz, 1H), 7.85(dd, J=8.2, 0.9Hz, 1H), 8.21(s, 1H), 10.16(s, 1H). |
| 78 | N-(3,5-Dimethoxyphenyl)-2-(7-fluoro-1H-benzimidazol-1-yl)acetamide | 329.3 | 330.1 | (400MHz, CD₃CN) δ ppm 3.65(s, 6H), 5.05(s, 2H), 6.18(bs, 1H), 6.71(d, J=2.0Hz, 2H), 6.93(dd, J=11.6, 8.1Hz, 1H), 7.11(m, 1H), 7.43(d, J=8.1Hz, 1H), 7.88(s, 1H), 8.60(bs, 1H). |
| 79 | N-(4-tert-Butylbenzyl)-2-(7-fluoro-1H-benzimidazol-1-yl)acetamide | 339.4 | 340.1 | (400MHz, CD₃CN) δ ppm: 1.21(s, 9H), 4.25(d, J=6.1Hz, 2H), 4.92(s, 2H), 6.92(dd, J=11.1, 8.1Hz, 1H), 7.00(s, 1H), 7.10(m, 3H), 7.28(m, 2H), 7.41(d, J=8.1Hz, 1H), 7.85(s, 1H). |
| 80 | N-(2,3-Dihydro-1H-inden-5-yl)-2-(7-fluoro-1H-benzimidazol-1-yl)acetamide | 309.3 | 310.1 | (400MHz, CD₃CN) δ ppm: 2.04(m, 2H), 2.85(q, J=8.1Hz, 4H), 5.12(s, 2H), 7.01(dd, J=11.6, 8.1Hz, 1H), 7.19(m, 3H), 7.42(bs, 1H), 7.51(d, J=8.1Hz, 1H), 7.96(s, 1H), 8.53(bs, 1H). |

Example 81

2-(7-Amino-1H-benzoimidazol-1-yl)-N-[3-(trifluoromethyl)phenyl]acetamide

To a solution of 2-(7-nitro-1H-benzoimidazol-1-yl)-N-[3-(trifluoromethyl)phenyl]acetamide, described above, (0.4 g, 1.1 mmol) in methanol (15 mL) 10% Pd/C (60 mg) was added. The mixture was hydrogenated at atmospheric pressure until the consumption of hydrogen ceased (1 h). The catalyst was removed by filtration through Celite, and the resulting clear solution was concentrated to dryness to yield the title compound, 0.36 g (99%). MS (ESI) m/z: 335.07 [M+H]. ¹H NMR (400 MHz, DMSO-D6) δ ppm 4.91 (s, 2H) 5.33 (s, 2H) 6.50 (m, 1H) 6.89 (t, J=7.6 Hz, 1H) 6.97 (m, 1H) 7.41 (d, J=7.6 Hz, 1H) 7.56 (t, J=7.8 Hz, 1H) 7.77 (m, 1H) 7.99 (s, 1H) 8.07 (s, 1H) 10.84 (s, 1H).

Example 82

2-[7-(acetylamino)-]H-benzoimidazol-1-yl]-N-[3-(trifluoromethyl)phenyl]acetamide To a chilled (0° C.) solution of 2-(7-amino-1H-benzoimidazol-1-yl)-N-[3-(trifluoromethyl)phenyl]acetamide (Example 81) (15 mg, 45 μmol) and triethylamine (13 μL, 90 μmol) in dry dichloromethane (0.5 mL) acetyl chloride 3.7 μL, 50 μmol) was added and the reaction mixture was allowed to warm up to ambient temperature. After 30 min methanol (1 mL) was added and the volatiles were removed under reduced pressure. The title compound was Purification on preparative HPLC yielded the title compound, 11 mg (65%). MS (ESI) m/z: 377.13 [M+H]. ¹H NMR (400 MHz, DMSO-D6) δ ppm 1.98 (s, 3H) 5.20 (s, 2H) 6.90 (m, 1H) 7.15 (m, 1H) 7.41 (m, 1H) 7.56 (m, 2H) 7.70 (m, 1H) 8.07 (s, 1H) 8.12 (s, 1H) 9.83 (s, 1H) 10.73 (s, 1H).

Example 83

2-[7-[(methylsulfonyl)amino]-1H-benzoimidazol-1-yl]-N-[3-(trifluoromethyl)phenyl]acetamide To a chilled (0° C.) solution of 2-(7-amino-1H-benzoimidazol-1-yl)-N-[3-(trifluoromethyl)phenyl]acetamide (Example 81) (15 mg, 45 μmol) and triethylamine (13 μL, 90 μmol) in dry dichloromethane (0.5 mL) methanesulfonyl chloride (8 μL, 100 μmol) was added and the reaction mixture was allowed to warm up to ambient temperature. After 30 min methanol (1 mL) was added, and the volatiles were removed under reduced pressure. The residue was dissolved in methanol (2 mL) and aqueous benzyltrimethylammonium hydroxide (40%, 200 μL) was added, the mixture was kept at room temperature for 1 h, then partitioned between ethyl acetate and phosphate buffer (pH 7). The organic phase was dried over magnesium sulfate and concentrated. Purification on preparative HPLC yielded the title compound, 13 mg (71%). MS (ESI) m/z: 413.03 [M+H]. $^1$H NMR (400 MHz, CD$_3$CN) δ ppm 3.02 (s, 3H) 5.37 (s, 2H) 7.20 (dd, J=7.6, 1.0 Hz, 1H) 7.27 (t, J=7.8 Hz, 1H) 7.41 (d, J=8.1 Hz, 1H) 7.51 (t, J=7.8 Hz, 1H), 7.69 (dd, J=8.1, 1.0 Hz, 1H) 7.73 (d, J=8.6 Hz, 1H) 7.96 (s, 1H) 7.98 (s, 1H) 9.13 (s, 1H).

Example 84

2-[7-(dimethylamino)-1H-benzoimidazol-1-yl]-N-[3-(trifluoromethyl)phenyl]acetamide To a solution of 2-(7-amino-1H-benzoimidazol-1-yl)-N-[3-(trifluoromethyl)phenyl]acetamide (Example 81) (22 mg, 66 μmol) and 37% aqueous formaldehyde (100 μL, 1.2 mmol) in ethanol (1 mL), acetic acid (60 μL) and sodium cyanoborohydride (30 mg, 0.5 mmol) were added. After 30 min the volatiles were removed under reduced pressure, and the residue was purified on preparative HPLC to yield the title compound, 8.5 mg (36%). MS (ESI) m/z: 363.18 [M+H]. $^1$H NMR (400 MHz, CD$_3$CN) δ ppm 2.66 (s, 6 H) 5.25 (s, 2H) 7.13 (d, J=8.1 Hz, 1H) 7.19 (t, J=7.8 Hz, 1H) 7.40 (d, J=8.1 Hz, 1H) 7.45 (m, 1H) 7.50 (t, J=8.1 Hz, 1H) 7.75 (d, J=8.1 Hz, 1H) 7.92 (s, 1H) 7.97 (s, 1H) 8.93 (s, 1H).

Example 85

2-[7-(Isopropylamino)-1H-benzoimidazol-1-yl]-N-[3-(trifluoromethyl)phenyl]acetamide The title compound was prepared in 15 mg (59%) yield according to the procedure described in Example 84, using acetone (100 μL) instead of formaldehyde. MS (ESI) m/z: 377.20 [M+H]. $^1$H NMR (400 MHz, CD$_3$OD) δ ppm 1.16 (d, J=6.1 Hz, 6H) 3.59 (m, 1H) 5.34 (s, 2H) 6.70 (m, 1H) 7.13 (m, 2H) 7.40 (d, J=8.1 Hz, 1H) 7.51 (t, J=8.1 Hz, 1H) 7.79 (d, J=8.1 Hz, 1H) 7.98 (s, 1H) 7.99 (s, 1H).

Example 86

2-(7-Cyano-1H-benzoimidazol-1-yl)-N-(3,5-dimethoxyphenyl)acetamide

To a solution of 2-(7-bromo-1H-benzoimidazol-1-yl)-N-(3,5-dimethoxyphenyl)acetamide (Example 52) (50 mg, 0.13 mmol) in dry DMF (0.64 mL) copper(I) cyanide (23 mg, 0.26 mmol) was added. The mixture was irradiated in a microwave oven at 200° C. for 60 min. The reaction mixture was partitioned between ethyl acetate and water. The organic extract was concentrated and the residue was purified by preparative HPLC to yield the title compound, 20 mg (46%). MS (ESI) m/z: 337.2 [M+H]. $^1$H NMR (400 MHz, DMSO-D6) δ ppm 3.69 (s, 6 H) 5.39 (s, 2H) 6.23 (t, J=2.3 Hz, 1H) 6.80 (d, J=2.0 Hz, 2 H) 7.37 (t, J=7.8 Hz, 1H) 7.74 (d, J=7.1 Hz, 1H) 8.05 (dd, J=8.1, 1.0 Hz, 1H) 8.40 (s, 1H) 10.47 (s, 1H).

Example 87

2-(7-Cyano-1H-benzoimidazol-1-yl)-N-(3-methoxyphenyl)acetamide

The title compound was prepared in 4.2 mg (23 %) yield from 2-(7-bromo-1H-benzoimidazol-1-yl)-N-(3-methoxyphenyl)acetamide (Example 53) according to the procedure described in Example 86. MS (ESI) m/z: 307.12 [M+H]. $^1$H NMR (400 MHz, CD$_3$CN) δ ppm 3.75 (s, 3H) 5.32 (s, 2H) 6.69 (dd, J=8.3, 1.8 Hz, 1H) 7.06 (dd, J=7.8, 1.3 Hz, 1H) 7.24 (m, 2H) 7.37 (t, J=7.8 Hz, 1H) 7.67 (dd, J=7.6, 1.0 Hz, 1 H) 8.02 (dd, J=8.1, 1.0 Hz, 1H) 8.09 (s, 1H) 8.70 (s, 1H).

Example 88

2-(7-Cyano-1H-benzoimidazol-1-yl)-N-[3-(trifluoromethyl)phenyl]acetamide

The title compound was prepared in 3.5 mg (18%) yield from 2-(7-bromo-1H-benzoimidazol-1-yl)-N-[3-(trifluoromethyl)phenyl]acetamide (Example 54) according to the procedure described in Example 86. MS (ESI) m/z: 345.05 [M+H]. $^1$H NMR (400 MHz, CD$_3$CN) δ ppm 5.36 (s, 2H) 7.38 (dd, J=8.2, 7.7 Hz, 1H) 7.43 (m, 1H) 7.53 (t, J=7.8 Hz, 1H) 7.68 (dd, J=7.6, 0.8 Hz, 1H) 7.74 (m, 1H) 7.96 (s, 1H) 8.02 (dd, J=8.3, 1.0 Hz, 1H) 8.11 (s, 1H) 8.96 (s, 1H).

Example 89

N-(3,5-Dimethoxyphenyl)-2-[7-(1H-tetrazol-5-yl)-1H-benzimidazol-1-yl]acetamide

To a suspension of 2-(7-cyano-1H-benzoimidazol-1-yl)-N-(3,5-dimethoxyphenyl)acetamide (Example 86) (12 mg, 36 μmol) in water (0.2 mL) sodium azide (6.6 mg, 100 μmol) and zinc bromide (22.5 mg, 100 μmol) were added. The mixture was heated in a sealed vial at 105° C. under vigorous stirring for 24 h. After cooling the mixture was acidified to pH 4 with 2M HCl, and extracted with ethyl acetate. The extract was washed with water, brine, dried over sodium sulfate and concentrated. Purification by preparative HPLC yielded the title compound, 3.5 mg (26%). MS (ESI) m/z: 380.1 [M+H].

Example 90

2-(6,7-Difluoro-1H-benzimidazol-1-yl)-N-[3-(trifluoromethyl)phenyl]acetamide

To a suspension of 4,5-difluoro-1H-benzimidazole (20 mg, 0.13 mmol) in toluene (260 μL), triethylamine (18 μL, 0.13 mmol) and 2-bromo-N-[3-(trifluoromethyl)phenyl]acetamide (37 mg, 0.13 mmol) were added. The reaction mixture was microwave-irradiated in a sealed vial at 120° C. for 30 min. The vial was cooled, opened and the contents dissolved in 20 mL ethyl acetate. The solution was washed with water (5 mL), saturated aqueous NaHCO$_3$ (5 mL) and brine (5 mL), dried over anhydrous Na$_2$SO$_4$ and concentrated under reduced pressure. Separation of the isomers in the crude product was performed on flash silica column using neat ethyl acetate to yield the title compound (11.3 mg, 25%). MS (ESI) m/z: 355.8 [M+H] $^1$H NMR (400 MHz, MeOD) δ ppm 5.31 (s, 2H), 7.20 (ddd, J=11.4, 9.0, 7.5 Hz, 1H), 7.40 (d, J=7.8 Hz, 1H), 7.47 (ddd, J=8.9, 3.7, 1.3 Hz, 1H), 7.52 (t, J=8.1 Hz, 1H), 7.79 (d, J=8.8 Hz, 1H), 7.96 (s, 1H), 8.20 (s, 1H).

Example 91

2-(1H-Benzimidazol-1-yl)-N-[3-(trifluoromethyl)phenyl]propanamide

Part A: Synthesis of 2-bromo-N-(3-trifluoromethyl-phenyl)-propionamide 2-Bromoproponyl bromide (430 mg, 2.1 mmol) was added under stirring to a solution of 3-trifluoromethyl-aniline (320 mg, 2.0 mmol) and triethylamine (0.3 mL, 2.1 mmol) in dichloromethane (15 mL). The reaction was stirred for 1 h at ambient temperature and the solvent was evaporated. The crude product was purified by flash chromatography (silica, 20% heptane in ethyl acetate) to afford 2-bromo-N-(3-trifluoromethyl-phenyl)-propionamide (0.50 g, 85%). Mass spectrum (ESI) m/z: 296.9, 297.9. $^1$H NMR (400 MHz, CDCl$_3$) δ ppm 2.0 (d, J=7.1 Hz, 3H), 4.5 (q, J=7.1 Hz, 1 H), 7.4 (d, J=7.6 Hz, 1H), 7.5 (t, J=7.8 Hz, 1H), 7.7 (d, J=7.9 Hz, 1H), 7.8 (s, 1 H), 8.2 (s, 1H).

Part B: Synthesis of the title compound

A solution of potassium tert-butoxide (0.25 mL of 1 M solution in THF, 0.25 mmol) was added to a solution of 1H-benzoimidazole (30 mg, 0.25 mmol) in anhydrous dioxane (10 mL) and anhydrous DMF (1 mL) under argon at ambient temperature. The mixture was stirred for 5 min before a solution of bromo-N-(3-trifluoromethyl-phenyl)-propionamide (59 mg, 0.2 mmol) in anhydrous dioxane (3 mL) was added. The mixture was stirred for 4 h, filtered and concentrated in vacuum. The crude product was purified on a preparative HPLC (XTerra C$_8$ column 19×300 mm, 0.1 M aqueous NH$_4$Ac/CH$_3$CN). Product-containing fractions were pooled and lyophilized to afford 40 mg (60%) of the title compound. $^1$H NMR (400 MHz, CDCl$_3$) δ ppm 1.8 (d, J=7.1 Hz, 3H), 5.1 (q, J=7.4 Hz, 1 H), 7.2 (m, 4 H), 7.4 (d, J=7.1 Hz, 1H), 7.5 (m, 2H,) 7.7 (m, 1H), 7.9 (s, 1H), 1/02 (s, 1 H).

Example 92

2-(1H-Benzimidazol-1-yl)-N-(3-chloro-4-fluorophenyl)acetamide

Part A: Synthesis of tert-Butyl 1H-benzimidazol-1-ylacetate

A solution of potassium tert-butoxide (0.6 mmol) in THF (0.6 mL) was added to a solution of 1H-benzoimidazole (71 mg, 0.6 mmol) in dioxane (15 mL) under stirring. tert-Butyl bromoacetate (97 mg, 0.5 mmol) was added to the white suspension and the mixture was stirred overnight at ambient temperature. The solvents were removed in vacuum and the product was purified on a silica gel column using a gradient of ethyl acetate in heptane) to afford benzimidazol-1-yl-acetic acid tert-butyl ester (110 mg, 95%). Mass spectrum (ESI) m/z: 233.0. $^1$H NMR (400 MHz, MeOD) δ ppm 1.5 (s, 9 H), 5.0 (s, 2 H), 7.3 (m, 2H), 7.4 (d, J=7.1 Hz, 1H), 7.7 (d, J=6.6 Hz, 1H), 8.1 (s, 1H).

Part B: Synthesis of 3-carboxymethyl-3H-benzoimidazol-1-ium trifluoro-acetate tert-Butyl 1H-benzimidazol-1-ylacetate (110 mg, 0.47 mmol) was dissolved in dichloromethane (3 mL) and trifluoroacetic acid (1 mL) was added. The reaction was stirred at ambient temperature for 24 h and the solvents were removed to afford 3-carboxymethyl-3H-benzoimidazol-1-ium trifluoro-acetate (136 mg, 100%). Mass spectrum (ESI) m/z: 177.0. $^1$H NMR (400 MHz, CD$_3$OD) δ ppm 5.3 (s, 2H), 7.5 (m, 2H), 7.8 (m, 2H), 9.4 (s, 1H).

Part C: Synthesis of the title compound

3-Carboxymethyl-3H-benzoimidazol-1-ium trifluoro-acetate (128 mg, 0.44 mmol) was dissolved in a mixture of oxalyl chloride (0.6 mL) and dichloromethane (3.4 mL). The reaction mixture was stirred for 30 min at ambient temperature and the solvent was evaporated. The residue was dissolved in a mixture of dichloromethane (2.5 mL) and anhydrous TBF (2.5 mL) and added to a mixture of 3-chloro4-fluoro-aniline (17 mg, 0.12 mmol) and N,N-(diisopropyl) aminomethylpolystyrene resin (140 mg, Argonaut Technologies, Inc) in anhydrous THF (3 mL). The mixture was shaken overnight. The resin was filtered off, the solvents were evaporated and the crude product was purified on a preparative LC/MS (XTerra Cs column 19×100mm, 0.1 M aqueous NH4Ac/CH$_3$CN). The pooled fractions were lyophilized to afford 7.2 mg (20%) of the title compound. Calculated for C$_{15}$H$_{11}$ClFN$_3$O m/z: 303.7, found 304.7 [M+H]$^+$. $^1$H NMR (400 M, MeOD) δ ppm 5.2 (s, 2H), 7.2 (t, J=9.1 Hz, 1H), 7.3 (m, 2H), 7.5 (m, 1H), 7.5 (d, J=7.1 Hz, 1H), 7.7 (d, J=7.1 Hz, 1H), 7.8 (dd, J=6.6, 2.5 Hz, 1H), 8.2 (s, 1H).

Example 93

2-(1H-Benzimidazol-1-yl)-N-(3-fluoro-4-methylphenyl)acetamide

The title compound was synthesised according to the procedure described in Example 89, from 3-carboxymethyl-3H-benzoimidazol-1-ium trifluoro-acetate and 3-fluoro-4-methyl-aniline. Yield 12 mg (35%). Calculated for C$_{16}$H$_{14}$FN$_3$O m/z: 283.3, found 284.3 [M+H]$^+$. $^1$H NMR (400 MHz, CD$_3$OD) δ ppm 2.2 (s, 3H), 5.1 (s, 2H), 7.1 (m, 2H), 7.3 (m, 2H), 7.4 (d, J=11.6 Hz, 1H), 7.5 (d, J=8.6 Hz, 1H), 7.7 (m, 1H), 8.1 (s, 1H).

Example 94

2-(1H-Benzimidazol-1-yl)-N-(3,4-difluorophenyl)acetamide

The title compound was synthesised according to the procedure described in Example 92, from 3-carboxymethyl-3H-benzoimidazol-1-ium trifluoro-acetate and 3,4-difluoroaniline Yield 9.1 mg (26%). Calculated for C$_{15}$H$_{11}$F$_2$N$_3$O m/z: 287.2, found 288.3 [M+H]$^+$. $^1$H NMR (400 MD, MeOD) δ ppm 5.2 (s, 2H), 7.3 (m, 4 H), 7.5 (d, J=7.1 Hz, 1H), 7.7 (m, 2H),8.2(s, 1H).

Example 95

2-(4-Methyl-1H-benzimidazol-1-yl)-N-[3-(trifluoromethyl)phenyl]acetamide

Part A: Synthesis of 4-methyl-1H-benzoimidazole

A solution of 3-methylbenzene-1,2-diamine (500 mg, 4.1 mmol) in formic acid (4.5 mL, 120 mmol) was irradiated in a microwave oven for 15 min at 135° C. The reaction mixture was cooled to ambient temperature and the formic acid was removed under reduced pressure. The residue was dissolved in ethyl acetate (20 mL) and extracted with saturated aqueous NaHCO$_3$ (2×10 mL), water (10 mL) and brine (10 mL). The organic phase was dried over anhydrous Na$_2$SO$_4$ and the solvent was removed in vacuum yielding 4-methyl-1H-benzoimidazole (519 mg, 96%). Calculated for C$_8$H$_8$N$_2$ m/z: 132.07, found 133.13 [M+H]$^+$. $^1$H NMR (400 MHz, DMSO-d6) δ ppm 2.50 (s, 3H), 6.96 (m, 1H), 7.06 (m, 1H), 7.38 (d, J=7.6 Hz, 1H), 8.15 (s, 1H), 12.41 (s, 1H).

Part B: Synthesis of the title compound

The title compound was synthesized in 39% yield (65 mg) according to a procedure described in Example 92, using 4-methyl-1H-benzoimidazole (66 mg, 0.5 mmol) and 2-bromo-N-(3-trifluoromethyl-phenyl)-acetamide (Example 92, part A) (141 mg, 0.5 mmol). Calculated for C$_{17}$H$_{14}$F$_3$N$_3$O m/z: 333.11, found 334.07 [M+H]$^+$. $^1$H NMR (400 MHz, DMSO-d6) δ ppm 2.54 (s, 3H), 5.18 (s, 2H), 7.01 (d, J=7.6 Hz, 1H), 7.12 (m, 1H), 7.33 (d, J=8.1 Hz, 1H), 7.42 (d, J=7.6 Hz, 1H), 7.57 (t, J=8.1 Hz, 1H), 7.77 (d, J=8.1 Hz, 1H), 8.06 (s, 1H), 8.18 (s, 1H), 10.77 (s, 1H).

Example 96

2-(1H-Benzimidazol-1-yl)-N-[3-(dimethylamino)phenyl]acetamide

Part A: 2-Bromo-N-(3-dimethylamino-phenyl)-acetamide Bromoacetyl bromide (21 μL, 0.24 mmol) was added to a suspension of N,N-dimethyl-benzene-1,3-diamine (27 mg, 0.2 mmol) and PS-diisopropylethylamine (170 mg of the resin, 0.6 mmol) in anhydrous THF (1.5 mL). The mixture was stirred overnight at ambient temperature. The resin was filtered off and the solution containing 2-bromo-N-(3-dimethylamino-phenyl)-acetamide was used directly in the next step (see Part B).

Part B: The title compound was synthesised according to the procedure described in Example 94, from 2-bromo-N-(3-dimethylamino-phenyl)-acetamide and 1H-benzoimidazole. Calculated for $C_{17}H_{18}N_4O$ m/z: 294.3, found 295.3 [M+H]$^+$.

Example 97

2-(1H-Benzimidazol-1-yl)-N-(4-tert-butylphenyl)acetamide

The title compound was synthesised according to the procedure described in Example 94 from 1H-benzoimidazole and 2-bromo-N-(4-tert-butyl-phenyl)-acetamide. The latter was synthesized from bromoacetyl bromide and 4-tert-butyl-aniline. Calculated for $C_{19}H_{21}N_3O$ m/z: 307.3, found 308.4 [M+H]$^+$.

Example 98

2-(1H-Benzimidazol-1-yl)-N-[3-(trifluoromethyl)benzyleacetamide

O-(7-Azabenzotriazo]1-yl)-N,N,N',N'-tetramethyluronium hexafluorophosphate (80 mg, 0.21 mmol) was added under stirring to a solution of 3-carboxymethyl-3H-benzoimidazol-1-ium trifluoro-acetate (Example 92 part B) (32 mg, 0.2 mmol) and N-methyl morpholine (66 μL, 0.6 mmol) in, acetonitrile (1 mL). After 5 min 3-trifluoromethyl-benzylaine (0.2 mmol, 35 mg) was added and the mixture was shaken overnight at ambient temperature. Purification was performed on a preparative LC/MS (XTerra $C_8$ column 19×100 mm, 0.1 M NH$_4$OAc/CH$_3$CN). Product-containing fractions were pooled and lyophilized thus affording 8.3 mg of the title compound (12%). Calculated for $C_{17}H_{14}F_3N_3O$ m/z: 333.32, found 334.1 [M+H]$^+$.

Example 99

2-(1H-Benzimidazol-1-yl)-N-(4-chlorobenzyl)acetamide

The title compound was synthesized according to a procedure described in Example 98 starting from 3-carboxymethyl-3H-benzoimidazol-1-ium trifluoro-acetate (Example 92, Part B) and 4-chloro-benzylamine. Calculated for $C_{16}H_{14}ClN_3O$ m/z: 299.76, found 301.1 [M+H]$^+$.

Example 100

2-(1H-Benzimidazol-1-yl)-N-(3,5-dimethoxyphenyl)acetamide

The title compound was synthesized according to a procedure described in Example 98 starting from 3-carboxymethyl-3H-benzoimidazol-1-ium trifluoro-acetate (Example 92 part B) and 3,5-dimethoxy-aniline. Calculated for $C_{17}H_{17}N_3O_3$ m/z: 311.34, found 311.88 [M+H]$^+$. $^1$H NMR (400 MHz, DMSO-d6) δ ppm 3.69 (s, 6 H), 5.14 (s, 2H), 6.23 (t, J=2.3 Hz, 1H), 6.82 (d, J=2.0 Hz, 2H), 7.22 (m, 2H), 7.51 (d, J=7.6 Hz, 1H), 7.66 (dd, J=7.3, 1.3 Hz, 1H), 8.21 (s, 1H), 10.41 (s, 1H).

Example 101

3-(1H-Benzimidazol-1-yl)-N-(4-tert-butylphenyl)propanamide

Part A: Synthesis of methyl 3-(1H-benzoimidazol-1-yl)propanoate To a solution of 1H-benzoimidazole (1.21 g, 10 mmol) in dry DMF (30 mL) potassium tert-butoxide solution in THF (1 M, 10.5 mL, 10.5 mmol) was added under stirring at ambient temperature. After 15 min methyl 3-bromopropanoate (1.1 mL, 10 mmol) was added drop-wise and the reaction mixture was stirred for 16 h. The mixture was quenched by addition of methanol (1 mL) and formic acid (1 mL), and concentrated in vacuum. The residue was treated with a mixture of ethyl acetate and water (25 and 5 mL, respectively), the organic phase was separated and washed with saturated aqueous NaHCO$_3$. The solvent was removed under reduced pressure and the crude product was purified on a pre-packed 12 g silica column (RediSep™, Isco, Inc.) using ethyl acetate as the eluent. Yield 0.56 g (27%). Calculated for $C_{11}H_{12}N_2O_2$ m/z: 204.09, found 204.97 [M+H]$^+$. $^1$H NMR (400 MHz, CDCl$_3$) δ ppm 2.92 (t, J=6.3 Hz, 2H), 3.67 (s, 3H), 4.57 (t, J=6.3 Hz, 2H), 7.36 (m, 2H), 7.45 (m, 1H), 7.87 (m, 1H), 8.36 (s, 1H).

Part B: Synthesis of 3-(1H-benzoimidazol-1-yl)propanoic acid

To a solution of methyl 3-(1H-benzoimidazol-1-yl)propanoate (0.56 g, 2.7 mmol) in methanol (0.5 mL) an aqueous solution of NaOH (2M, 0.5 mL) was added under stirring at ambient temperature. Upon consumption of the starting material (15 min), methanol was removed from the reaction mixture under reduced pressure. Aqueous HCl (1 M, 1 mL) was added followed by evaporation of the volatiles. To the residue dichloromethane (30 mL) containing triethylamine (1 mL) was added and the slurry was filtered. The filtrate was concentrated and the crude product was purified on a pre-packed 12 g silica column (RediSep™, Isco, Inc.) using 3% methanol and 1% triethylamine in dichloromethane as an eluent. Product-containing fractions were pooled, concentrated under reduced pressure, co-evaporated with ethyl acetate (3×10 mL) and dried under reduced pressure at 40° C. for 24 h. Yield 0.34 g (65%). Calculated for $C_{10}H_{10}N_2O_2$ m/z: 190.07, found 190.91 [M+H]$^+$. $^1$H NMR (400 MHz, DMSO-d6) δ ppm 2.81 (t, J=6.8 Hz, 2H), 4.45 (t, J=6.8 Hz, 2H), 7.22 (m, 2H), 7.61 (dd, J=2.0, 1.0 Hz, 1H), 7.63 (m, 1H), 8.17 (s, 1H).

Part C. The title compound was synthesized according to a procedure described in Example 98 starting from 3-benzoimidazol-1-yl-propanoic acid and 4-tert-butyl-aniline. Calculated for $C_{16}H_{23}N_3O$ m/z: 321.18, found 322.1 $[M+H]^+$.

Example 102

4-(1H-Benzimidazol-1-yl)-N-(4-tert-butylphenyl)butanamide

Part A: Synthesis of methyl 4-(1H-benzoimidazol-1-yl)butanoate Methyl 4-(1H-benzoimidazol-1-yl)butanoate was prepared according to the procedure described in Example 101 (Part A) from 1H-benzomidazole (1.21 g, 10 mmol) and methyl 4-bromobutanoate (1.3 mL, 10 mmol) in the presence of tetra-n-butylammonium iodide (300 mg, 0.8 mmol). Purification was performed using 2% methanol in dichloromethane. Yield 1.41 g (65%). Calculated for $C_{12}H_{14}N_2O_2$ m/z: 218.11, found 219.98 $[M+H]^+$. $^1H$ NMR (400 MHz, $CDCl_3$) δ ppm 2.22 (m, 2H), 2.35 (t, J=6.6 Hz, 2H), 3.67 (s, 3H), 4.31 (t, J=7.1 Hz, 2H), 7.33 (m, 2H), 7.46 (m, 1H), 7.83 (m, 1H), 8.14 (s, 1H).

Part B: Synthesis of 4-(1H-benzoimidazol-1-yl)butanoic acid

The title compound was prepared according to the procedure described in Example 101 (Part B) starting from methyl 4-(1H-benzoimidazol-1-yl)butanoate (1.41 g, 6.5 mmol). Yield 1.1 g (54%). Calculated for $C_{11}H_{12}N_2O_2$ m/z: 204.09, found 204.91 $[M+H]^+$. $^1H$ NMR (400 MHz, DMSO-d6) δ ppm 2.01 (m, 2H), 2.22 (t, J=7.3 Hz, 2H), 4.26 (t, J=7.1 Hz, 2H), 7.22 (m, 2H), 7.62 (dd, J=18.2, 8.1 Hz, 2H), 8.20 (s, 1H), 12.11 (s, 1H).

Part C. The title compound was synthesized according to a procedure described in Example 98 starting from 4-benzoimidazol-1-yl-butyric acid and 4-tert-butyl-aniline. Calculated for C16H23N3O m/z: 335.20, found 336.1 $[M+H]^+$.

Example 103

2-(1H-Benzimidazol-1-yl)-N-(2-methyl-1,3-benzothiazol-5-yl)acetamide

2-Methyl-benzothiazol-5-ylamine (32 mg, 0.2 mmol) and bromoacethyl bromide were added to a suspension of (N,N-diisopropyl)aminomethylpolystyrene resin (170 mg) in anhydrous TBF (2 mL) and the reaction mixture was shaken for 4 h at ambient temperature. The resin was then filtered off. 1H-benzoimidazole (35 mg, 0.3 mmol) and potassium tert-butoxide (0.36 mL of 1 M solution in THF, 0.36 mmol,) were added and the mixture was stirred at 55° C. for 24 h. The crude product was purified on a preparative LC/MS (XTerra $C_8$ column 19×100 mm, 0.1 M aqueous $NH_4Ac/CH_3CN$). The pooled to fractions were lyophilized to afford 4 mg (6%) of the title compound. Calculated for $C_{17}H_{14}N_4OS$ m/z: 322.39, found 323.0 $[M+H]^+$.

Example 104

2-(1H-Benzimidazol-1-yl)-N-[3-(trifluoromethyl)phenyl]acetamide

A solution of potassium tert-butoxide (1.7 mL of 1 M solution in THF, 1.7 mmol,) was added to a solution of 1H-benzoimidazole (165 mg, 1.4 mmol) in anhydrous TBF (3 mL). The reaction mixture was stirred for 20 min at ambient temperature. 2-Bromo-N-(3-trifluoromethyl-phenyl)-acetamide (Example 92 part A) was added (261 mg, 0.93 mmol) and the mixture was stirred at 55° C. for subsequent 24 h. The crude product was purified on a preparative HPLC (XTerra $C_8$ column 19×300 mm, 0.1 M aqueous $NH_4Ac/CH_3CN$). The pooled fractions were lyophilized to afford 81 mg (27%) of the title compound. Calculated for $C_{16}H_{12}F_3N_3O$ m/z: 319.29, found 320.0 $[M+H]^+$. $^1H$ NMR (400 MeOH) δ ppm 5.2 (s, 2H), 7.3 (m, 2H), 7.4 (d, J=7.6 Hz, 1H), 7.5 (m, 2H), 7.7 (d, J=7.1 Hz, 1H), 7.8 (d, J=8.6 Hz, 1H), 8.0 (s, 1H), 8.2 (s, 1H).

Example 105

2-(4-Nitro-1H-benzimidazol-1-yl)-N-[3-(trifluoromethyl)phenyl]acetamide

Potassium tert-butoxide (195 mg, 1.73 mmol,) was added to a stirred solution of 4(7)-nitro-1H-benzoimidazole (270 mg, 1.65 mmol) in DMF (5.5 mL). After 10 min 2-bromo-N-[3-(trifluoromethyl)phenyl]acetamide (466 mg, 1.65 mmol) was added and the mixture was stirred for 3 h at ambient temperature. The solvent was removed under reduced pressure and the residue was treated with ethyl acetate and 0.5 M phosphate buffer (pH 7) (25 mL of each). The organic layer was separated, washed with brine (5 mL), dried over anhydrous $Na_2SO_4$ and concentrated to leave a mixture of 4- and 7-nitro regioisomers. Separation of the mixture of regioisomers was performed on preparative HPLC (XTerra $C_8$ column 19×300 mm, 0.1 M $NH_4OAc/CH_3CN$). Product-containing fractions were pooled and lyophilised affording the pure individual regioisomers. The major product: 2-(4-nitro-1H-benzimidazol-1-yl)-N-[3-(trifluoromethyl)phenyl]acetamide was obtained in 73% (435 mg) yield. $^1H$ NMR (400 MHz, DMSO-d6) δ ppm 5.36 (s, 2H), 7.45 (m, 2H), 7.58 (t, J=7.8 Hz, 1H), 7.77 (d, J=8.6 Hz, 1H), 8.06 (bs, 2H), 8.08 (s, 1H), 8.55 (s, 1 H), 10.83 (s, 1H).

Example 106

2-(4-Amino-1H-benzimidazol-1-yl)-N-[3-(trifluoromethyl)phenyl]acetamide 2-(4-Nitro-1H-benzimidazol-1-yl)-N-[3-(trifluoromethyl)phenyl]acetamide (60 mg, 0.17 mmol) (see Example 105) was dissolved in ethanol (1.44 mL) and tin(II) chloride (192 mg, is 0.85 mmol) was added. The reaction mixture was stirred at 70° C. for 16 h and then poured onto a mixture of ice and saturated aqueous $NaHCO_3$ (20 mL). The basic solution was extracted with ethyl acetate (3×10 mL), washed with brine (10 mL), dried over anhydrous $Na_2SO_4$ and concentrated. The purification of the crude product was performed by preparative HPLC (XTerra $C_8$ column 19×300 mm, 0.1 M $NH_4OAc/CH_3CN$). Product-containing fractions were pooled and lyophilised affording the title compound (11.3 mg, 20%). Calculated for $C_{16}H_{13}F_3N_4O$ m/z: 334.10, found 335.09 $[M+H]^+$. $^1H$ NMR (400 MHz, DMSO-d6) δ ppm 5.07 (s, 2H), 5.24 (s, 2H), 6.37 (dd, J=7.6, 0.8 Hz, 1H), 6.64 (dd, J=8.0, 0.63 Hz, 1H), 6.90 (t, J=7.8 Hz, 1H), 7.42 (d, J=7.8 Hz, 1H), 7.57 (t, J=8.0 Hz, 1H), 7.77 (m, 1H), 7.99 (s, 1H), 8.06 (s, 1H), 10.74 (s, 1H).

Example 107

2-(1H-Benzimidazol-1-yl)-N-heptylacetamide

O-(7-Azabenzotriazol1-yl)-N,N,N',N'-tetramethyluronium hexafluorophosphate (80 mg, 0.21 mmol) was added under stirring to a solution of 1H-benzoimidazol-1-ylacetic acid triethylammonium salt (55.5 mg, 0.2 mmol) and N-methyl morpholine (66 μL, 0.6 mmol) in acetonitrile (1 mL). After 5 min 1-heptylamine (30 μL, 0.2 mmol) was added and mixture was stirred at ambient temperature for 3 h. The solvent was evaporated, the residue was dissolved in ethyl acetate (15 mL) and extracted with saturated aqueous NaHCO$_3$ (5 mL) and brine (5 mL) then dried over anhydrous Na$_2$SO$_4$ and concentrated. Purification of the crude product was performed by preparative HPLC (XTerra C$_8$ column 19×300 mm, 0.1 M NH$_4$OAc/CH$_3$CN). Product-containing fractions were pooled and lyophilised affording the title compound (43.7 mg, 80%). Calculated for C$_{16}$H$_{23}$N$_3$O m/z: 273.18, found 274.03 [M+H]$^+$. $^1$H NMR (400 MHz, DMSO-d6) δ ppm 0.85 (m, 3H), 1.26 (m, 8 H), 1.41 (m, 2H), 3.07 (m, 2H), 4.88 (s, 2H), 7.20 (m, 2H), 7.42 (m, 1H), 7.64 (m, 1H), 8.14 (s, 1H), 8.27 (t, J=5.6 Hz, 1H).

Example 108

2-(5-Fluoro-]H-indol-3-yl)-N-[3-(trifluoromethyl)phenyl]acetamide

The title compound was synthesized in 57% yield (38.5 mg) according to a procedure described in Example 107 starting from (5-fluoro-1H-indol-3-yl)-acetic acid and 3-trifluoromethyl-aniline. Calculated for C$_{16}$H$_{23}$N$_3$O m/z: 336.09, found 336.88 [M+H]$^+$. $^1$H NMR (400 MHz, DMSO-d6) δ 3.73 (s, 2H), 6.91 (m, 1H), 7.34 (m, 4 H), 7.53 (t, J=8.1 Hz, 1H), 7.78 (d, J=8.1 Hz, 1H), 8.09 (s, 1H), 10.42 (s, 1H), 11.03 (s, 1H).

Example 109

2-(1-Methyl-1H-indol-3-yl)-N-[3-(trifluoromethyl)phenyl]acetamide

The title compound was synthesized in 62% yield (41.1 mg) according to a procedure described in Example 107 starting from (1-methyl-1H-indol-3-yl)-acetic acid and 3-trifluoromethyl-aniline. Calculated for C$_{16}$H$_{23}$N$_3$O m/z: 332.11, found 332.89 [M+H]$^+$. $^1$H NMR (400 MHz, DMSO-d6) δ ppm 3.74 (s, 2H), 3.75 (s, 3H), 7.01 (m, 1H), 7.14 (m, 1H), 7.25 (s, 1H), 7.38 (t, J=8.1 Hz, 2H), 7.53 (t, J=7.8 Hz, 1H), 7.60 (d, J=8.1 Hz, 1H), 7.79 (d, J=8.6 Hz, 1H), 8.10 (s, 1H), 10.43 (s, 1H).

Example 110

2-(1H-Indol-1-yl)-N-[3-(trifluoromethyl)phenyl]acetamide

Part A: Synthesis of 2-bromo-N-(3-trifluoromethyl-phenyl)-acetamide Bromoacetyl bromide (1.41 g, 7 mmol) was added under stirring to a solution of 3-trifluoromethyl-aniline (0.77 g, 4.8 mmol) and triethylamine (0.83 mL, 8.2 mmol) in THF (60 mL) at 0° C. The reaction was stirred for 3 h at 0° C. and the solvent was evaporated. The crude product was purified by flash chromatography (Silica, heptane/ethyl acetate 1:1) to afford 2-bromo-N-(3-trifluoromethyl-phenyl)-acetamide (1.35 g, 100%). Mass spectrum (ESI) m/z: 280.0, 282.0. $^1$H NMR (400 MHz, DMSO-d6) δ ppm 3.93 (s, 2H), 7.31 (d, J=8.1 Hz, 1H), 7.44 (t, J=7.8 Hz, 1H), 7.63 (d, J=8.1 Hz, 1H), 7.93 (s, 1H), 10.57 (s, 1H).
Part B: Synthesis of title compound
A solution of potassium tert-butoxide (0.25 mmol) in TBF (0.25 mL) was added to a solution of 1H-indole (30 mg, 0.25 mmol) in a mixture of dioxane (6 m]L) and DMF (1.5 mL) under argon atmosphere at ambient temperature. The solution was stirred for 5 min before a solution of 2-bromo-N-(3-trifluoromethyl-phenyl)-acetamide (0.2 mmol) in DMF (1 mL) was added dropwise. The reaction mixture was stirred overnight at ambient temperature and the solvents were-removed in vacuum. The crude product was purified on a preparative LC/MS (XTerra C$_8$ column 19×100 mm, 0.1 M aqueous NH$_4$Ac/CH$_3$CN). The product-containing fractions were pooled and lyophilized to afford 24 mg (38%) of the title compound. Calculated for C$_{17}$H$_{13}$F$_3$N$_2$O m/z: 318.3, found 319.0 [M+H]$^+$. $^1$H NMR (400 MHz, CDCl$_3$) δ ppm 4.9 (s, 2H), 6.7 (d, J=3.0 Hz, 1H), 7.0 (s, 1H), 7.1 (d, J=3.0 Hz, 1H), 7.2-7.3 (m, 5 H), 7.4 (m, 1H), 7.6 (s, 1H), 7.7 (d, J=8.1 Hz, 1H).

Pharmacology 1. hVR1 FLIPR (Fluorometric Image Plate Reader) screening assay

Transfected CHO cells, stably expessing hVR1 (15,000 cells/well) are seeded in 50 μL media in a black clear bottom 384 plate (Greiner) and grown in a humidified incubator (37° C., 2% CO$_2$), 24-30 hours prior to experiment.

Subsequently, the media is removed from the cell plate by inversion and 2 μM Fluo-4 is added using a multidrop (Labsystems). Following the 40 min dye incubation in the dark at 37° C. and 2% CO$_2$, the extracellular dye present is washed away using an EMBLA (Scatron), leaving the cells in 40 μL of assay buffer (1×HBSS, 10 mM D-Glucose, 1 mM CaCl$_2$, 10 mM HEPES, 10×7.5% NaHCO$_3$ and 2.5 mM Probenecid).

FLIPR assay—IC$_{50}$ determination protocol

For IC$_{50}$ determinations the fluorescence is read using FLIPR filter 1 (em 520-545 nM). A cellular baseline recording is taken for 30 seconds, followed by a 20 μL addition of 10, titrated half-log concentrations of the test compound, yielding cellular concentration ranging from 3 μM to 0.1 nM. Data is collected every 2 seconds for a further 5 min prior to the addition of a VR1 agonist solution: either 50 nM solution of capsaicin or MES (2-[N-morpholino]ethanesulfonic acid) buffer (pH 5.2), by the FLIPR pipettor. The FLIPR continues to collect data for a further 4 min. Compounds having antagonistic properties against the hVR1 will inhibit the increase in intracellular calcium in response to the capsaicin addition. This consequently leading to a reduction in fluorescence signal and providing a reduced fluorescence reading, compared with no compound, buffer controls. Data is exported by the FLIPR program as a sum of fluorescence calculated under the curve upon the addition of capsaicin. Maximum inhibition, Hill slope and IC$_{50}$ data for each compound are generated.

2. DRGs were dissected out from adult Sprague Dawley rats (100-300 gr), and placed on ice in L15 Leibovitz medium. The ganglia were enzyme treated with Collagenase 80 U/ml+ Dispase 34 U/mL dissolved in DMEM+5% serum, overnight at 37° C. The next day, cells were triturated with fire polished pasteur pipettes, and seeded in the center of 58 mm diameter Nunc cell dishes coated with Poly-D Lysine (1 mg/mL). The DRGs were cultured in a defined medium without foetal bovine serum, containing Dulbecco's MEM/NUT MIX F-12 (1:1) without L-glutamine but with pyridoxine, 6 mg/mL D(+)-Glucose, 100 μg/mL apo-transferrin, 1 mg/mL BSA, 20 μg/mL insulin, 2 mM L-glutamine, 50 IU/mL Penicillin, 50 μg/mL Streptomycin and 0.01 μg/mL NGF-7S.

When the cells had grown for 2 days up to 4 weeks, the experiments were done. Cells were chosen based on size and presence of neurites. Small cells with long processes were used for recording (most likely to be C neurons, with native VR1 receptors).

The cells were recorded with conventional whole cell voltage clamp patch clamp, using the following solutions (calcium ion free):

The extracellular solution comprised (in mM): NaCl 137, KCl 5, MgCl$_2$*H$_2$O 1.2, HEPES 10, Glucose 10, EGTA 5, Sucrose 50, pH to 7.4 with NaOH. The intracellular solution comprised K-gluconate 140, NaCl 3, MgCl$_2$*H$_2$O 1.2, HEPES 10, EGTA 1, pH to 7.2 with KOH. When the cells were penetrated with suction, a puff of capsaicin (500 nM) was used to determine if the cell expressed VR1 receptor. If not, a new cell was chosen. If yes, then the compounds were added in increasing doses before the capsaicin pulse (500 nM), to determine an IC$_{50}$ value.

| List of abbreviations | |
| --- | --- |
| VR1 | vanilloid receptor 1 |
| IBS | irritable bowel syndrome |
| IBD | inflammatory bowel disease |
| GERD | gastro-esophageal reflux disease |
| DRG | Dorsal Root Ganglion |
| BSA | Bovine Serum Albumin |
| HEPES | 4-(2-Hydroxyethyl)piperazine-1-ethanesulfonic acid |
| EGTA | Ethylene glycol-bis(2-aminoethylether)-N,N,N',N'-tetraacetic acid |
| DMEM | Dulbeccos Modified Eagle's Medium |

Results

Typical IC$_{50}$ values as measured in the assays described above are 10 μM or less. In one aspect of the invention the IC$_{50}$ is below 500 nM. In another aspect of the invention the IC$_{50}$ is below 100 nM. In a further aspect of the invention the IC$_{50}$ is below 10 nM.

| Results from the hVR1 FLIPR | | |
| --- | --- | --- |
| Example No. | IC$_{50}$ nM (agonist) | |
| 7 | 50 (capsaicin) | 70 (H$^+$/MES buffer) |
| 67 | 160 (capsaicin) | 140 (H$^+$/MES buffer) |

The invention claimed is:

1. A compound having the formula

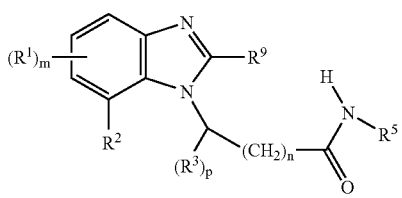

(I)

wherein:
R$^1$ is H, NO$_2$, halo, NR$^6$R$^7$, C$_{1-6}$alkyl, C$_{2-6}$alkenyl, C$_{2-6}$alkynyl, C$_{1-6}$haloalkyl, C$_{1-6}$haloalkylO, R$^6$OC$_{0-6}$alkyl, R$^6$CO, R$^6$OCO or CONR$^6$R$^7$;
m is 0, 1, 2 or 3;
R$^2$ is NO$_2$, halo, NR$^6$R$^7$, C$_{1-6}$alkyl, C$_{2-6}$alkenyl, C$_{2-6}$alkynyl, C$_{1-6}$haloalkyl, C$_{1-6}$haloalkylO, cyano, R$^6$OC$_{0-6}$alkyl, R$^6$CO, R$^6$OCO, R$^6$CONR, R$^6$R$^7$NCO, R$^8$SO$_2$, R$^8$SO$_2$HN, arylC$_{0-6}$alkyl or heteroarylC$_{0-6}$alkyl;
R$^3$ and R$^9$ are each independently H or C$_{1-4}$alkyl;
p is 0, 1 or 2;
n is 0, 2, 3 or 4;
R$^5$ is C$_{1-10}$alkyl, C$_{6-10}$arylC$_{0-6}$alkyl, C$_{3-7}$cycloalkylC$_{0-6}$alkyl or C$_{5-6}$heteroarylC$_{0-6}$alkyl, whereby any aryl, heteroaryl or cycloalkyl may be fused with aryl, heteroaryl, C$_{3-7}$cycloalkyl or C$_{3-7}$heterocycloalkyl, and which R$^5$ may be substituted with one or more A;
A is H, OH, NO$_2$, cyano, R$^6$CO, halo, C$_{1-6}$alkyl, NR$^6$R$^7$, C$_{1-6}$haloalkyl, C$^{1-6}$haloalkylO, R$^6$OC$_{0-6}$alkyl, hydroxyC$_{1-6}$alkyl, R$^8$SO$_2$, R$^8$SO$_2$HN, C$_{5-6}$arylO or CONR$^6$R$^7$;
R$^6$ and R$^7$ are each independently H or C$_{1-6}$alkyl; and
R$^8$ is NR$^6$R$^7$ or C$_{1-4}$alkyl,
or a pharmaceutically acceptable salt thereof.

2. A compound according to claim 1, wherein:
R$^1$ is H, halo, NR$^6$R$^7$, C$_{1-6}$alkyl, C$_{1-6}$haloalkyl, C$_{1-6}$haloalkylO, R$^6$OC$_{0-6}$alkyl, R$^6$CO, R$^6$OCO or CONR$^6$R$^7$;
m is 0 or 1;
R$^2$ is NO$_2$, halo, NR$^6$R$^7$, C$_{1-6}$alkyl, C$_{1-6}$haloalkyl, cyano, R$^6$OCO, R$^6$CONR$^7$, R$^8$SO$_2$, R$^8$SO$_2$HN or heteroarylC$_{0-6}$ alkyl;
R$^3$ and R$^9$ are each independently H or C$_{1-4}$alkyl;
p is 0;
n is 0;
R$^5$ is C$_{1-10}$alkyl, C$_{6-10}$arylC$_{0-6}$alkyl or C$_{5-6}$heteroarylC$_{0-6}$alkyl, whereby any aryl may be fused with C$_{3-7}$cycloalkyl or C$_{3-7}$heterocycloalkyl, and which R$^5$ may be substituted with one or more A;
A is H, cyano, halo, NO$_2$ , C$_{1-6}$alkyl, NR$^6$R$^7$, C$_{1-6}$haloalkyl, C$_{1-6}$haloalkylO, R$^6$OC$_{0-6}$alkyl, hydroxyC$_{1-6}$alkyl, R$^8$SO$_2$ or C$_{5-6}$arylO;
R$^6$ and R$^7$ are each independently H or C$_{1-6}$alkyl; and
R$^8$ is NR$^6$R$^7$ or C$_{1-4}$alkyl, or a pharmaceutically acceptable salt thereof.

3. A compound according to claim 1, wherein
R$^2$ is NO$_2$, halo, NR$^6$R$^7$, C$_{1-4}$alkyl, C$_{1-4}$haloalkyl, C$_{1-2}$haloalkylO, cyano, R$^6$OC$_{0-4}$alkyl, R$^6$CO, R$^6$OCO, R$^6$CONR$^7$, R$^6$R$^7$NCO, R$^8$SO$_2$, R$^8$SO$_2$HN, arylC$_{0-6}$alkyl and heteroaryl and wherein
R$^6$ and R$^7$ are each independently H or C$_{1-4}$alkyl and
R$^8$ is NR$^6$R$^7$ or C$_{1-3}$alkyl, or a pharmaceutically acceptable salt thereof.

4. A compound according to claim 1, wherein R$^2$ is NO$_2$, or a pharmaceutically acceptable salt thereof.

5. A compound according to claim 1, wherein R$^5$ is phenyl, which may be substituted with one or more A, or a pharmaceutically acceptable salt thereof.

6. A compound according to claim 5, wherein A is selected from the group consisting of halo, alkoxy, haloalkoxy, haloalkyl, alkyl, alkanol, cyano, phenoxy, alkylsulfonyl and (di)alkylamino, or a pharmaceutically acceptable salt thereof.

7. A compound according to claim 1, wherein A is selected from the group consisting of fluoro, iodo, chloro, bromo, methoxy, ethoxy, trifluoromethyl, difluoromethoxy, trifluoromethoxy, tetrafluoroethoxy, methyl, ethyl, propyl, butyl, hydroxyethyl, cyano, phenoxymethylsulfonyl and dimethylamino, or a pharmaceutically acceptable salt thereof.

8. A compound according to claim 1, selected from the group consisting of:
N-(3-Fluoro-4-methoxy-phenyl)-2-(7-nitro-1H-benzimidazol-1-yl)-acetamide,
N-[2-Fluoro-4-(trifluoromethyl)phenyl]-2-(7-nitro-1H-benzimidazol-1-yl)acetamide,
N-(3-Chloro-4-iodophenyl)-2-(7-nitro-1H-benzimidazol-1 -yl)acetamide, N-(3-Chloro-4-methoxyphenyl)-2-(7-nitro-1H-benzimidazol-1-yl)acetamide,
N-[3-(Difluoromethoxy)phenyl]-2-(7-nitro-1H-benzimidazol-1-yl)acetamide,
N-[3-Methoxy-5-(trifluoromethyl)phenyl]-2-(7-nitro-1H-benzimidazol-1-yl)acetamide,
N-(3,5-Difluorophenyl)-2-(7-nitro-1H-benzimidazol-1-yl)acetamide,
2-(7-Nitro-1H-benzimidazol-1-yl)-N-[4-(trifluoromethoxy)phenyl]acetamide,
2-(7-Nitro-1H-benzimidazol-1-yl)-N-[3-(1,1,2,2-tetrafluoroethoxy)phenyl]acetamide,
N-(4-tert-Butylphenyl)-2-(7-nitro-1H-benzimidazol-1-yl)acetamide,
N-[3-(1-Hydroxyethyl)phenyl]-2-(7-nitro-1H-benzimidazol-1-yl)acetamide,
2-(7-Nitro-1H-benzimidazol-1-yl)-N-[4-(trifluoromethyl)phenyl]acetamide,
N-(3-Chlorophenyl)-2-(7-nitro-1H-benzimidazol-1-yl)acetamide,
N-Hexyl-2-(7-nitro-1H-benzimidazol-1-yl)acetamide,
N-(3,4-Difluorophenyl)-2-(7-nitro-1H-benzimidazol-1-yl)acetamide,
N-(4-Cyanophenyl)-2-(7-nitro-1H-benzimidazol-1-yl)acetamide,
N-(2,3-Dihydro-1,4-benzodioxin-6-yl)-2-(7-nitro-1H-benzimidazol-1-yl)acetamide,
N-(2-Bromobenzyl)-2-(7-nitro-1H-benzimidazol-1-yl)acetamide,
2-(7-Nitro-1H-benzimidazol-1-yl)-N-[3-(trifluoromethyl)benzyl]acetamide,
N-(4-Methylpyridin-2-yl)-2-(7-nitro-1H-benzimidazol-1-yl)acetamide,
N-(3-Cyanophenyl)-2-(7-nitro-1H-benzimidazol-1-yl)acetamide,
N-(3,5-Dimethoxyphenyl)-2-(7-nitro-1H-benzimidazol-1-yl)acetamide,
N-(4-Methoxyphenyl)-2-(7-nitro-1H-benzimidazol-1-yl)acetamide,
N-(3-Ethoxyphenyl)-2-(7-nitro-1H-benzimidazol-1-yl)acetamide,
N-(3,4-Dimethoxyphenyl)-2-(7-nitro-1H-benzimidazol-1-yl)acetamide,
2-(7-Nitro-1H-benzimidazol-1-yl)-N-(3,4,5-trimethoxyphenyl)acetamide,
2-(7-Nitro-1H-benzimidazol-1-yl)-N-[3-(trifluoromethoxy)phenyl]acetamide,
2-(7-Nitro-1H-benzimidazol-1-yl)-N-(3-phenoxyphenyl)acetamide,
N-(4-Butylphenyl)-2-(7-nitro-1H-benzimidazol-1-yl)acetamide,
N-(2-Fluoro-4-iodophenyl)-2-(7-nitro-1H-benzimidazol-1-yl)acetamide,
2-(7-Nitro-1H-benzimidazol-1-yl)-N-[2-(trifluoromethoxy)phenyl]acetamide,
N-(4-Methoxyphenyl)-2-(7-nitro-1H-benzimidazol-1-yl)acetamide,
2-(7-Nitro-1H-benzimidazol-1-yl)-N-(2-phenoxyphenyl)acetamide,
N-(4-Bromo-2-fluorophenyl)-2-(7-nitro-1H-benzimidazol-1-yl)acetamide,
N-[3-(Methylsulfonyl)phenyl]-2-(7-nitro-1H-benzimidazol-1-yl)acetamide,
N-[4-(Methylsulfonyl)phenyl]-2-(7-nitro-1H-benzimidazol-1-yl)acetamide,
2-(7-Nitro-1H-benzimidazol-1-yl)-N-[4-trifluoromethyl)benzyl]acetamide,
N-(4-tert-Butylbenzyl)-2-(7-nitro-1H-benzimidazol-1-yl)acetamide,
N-(2,3-dihydro-1H-inden-5-yl)-2-(7-nitro-1H-benzimidazol-1-yl)acetamide,
2-(7-Nitro-1H-benzimidazol-1-yl)-N-[4-(trifluoromethoxy)benzyl]acetamide,
N-(4-Isopropylphenyl)-2-(7-nitro-1H-benzimidazol-1-yl)acetamide,
N-(3,4-Dimethylphenyl)-2-(7-nitro-1H-benzimidazol-1-yl)acetamide,
N1,3-Benzodioxol-5-yl-2-(7-nitro-1H-benzimidazol-1-yl)acetamide,
N-[3-Bromo-4-(trifluoromethoxy)phenyl]-2-(7-nitro-1H-benzimidazol-1-yl)acetamide,
N-(3-Fluoro-2-methoxyphenyl)-2-(7-nitro-1H-benzimidazol-1-yl)acetamide,
N-(3,5-dimethoxyphenyl)-2-(7-nitro-1H-benzimidazol-1-yl)propanamide,
N-(3-Ethoxyphenyl)-2-(7-nitro-1H-benzimidazol-1-yl)propanamide,
2-(7-Nitro-1H-benzimidazol-1-yl)-N-[3-(trifluoromethyl)phenyl]propanamide,
N-(3,5-Dimethylphenyl)-2-(7-nitro-1H-benzimidazol-1-yl)acetamide,
2-(7-Nitro-1H-benzimidazol-1-yl)-N-[3-(trifluoromethyl)phenyl]acetamide,
2-(7-Bromo-1H-benzimidazol-1-yl)-N-(3,5-dimethoxyphenyl)acetamide,
2-(7-Bromo-1H-benzimidazol-1-yl)-N-(3-methoxyphenyl)acetamide,
2-(7-Bromo-1H-benzimidazol-1-yl)-N-[3-(trifluoromethyl)phenyl]acetamide,
2-(7-Chloro-1H-benzimidazol-1-yl)-N-(3,5-dimethoxyphenyl)acetamide,
2-(7-Chloro-1H-benzimidazol-1-yl)-N-[3-(trifluoromethyl)phenyl]acetamide,
2-(7-Chloro-1H-benzimidazol-1-yl)-N-(4-methylphenyl)acetamide,
2-(7-Chloro-1H-benzimidazol-1-yl)-N-(2,3-dihydro-1H-inden-5-yl)acetamide,
2-(7-Methyl-1H-benzimidazol-1-yl)-N-(4-methylphenyl)acetamide,
N-(3,5-Dimethoxyphenyl)-2-(7-methyl-1H-benzimidazol-1-yl)acetamide,
2-(7-Methyl-1H-benzimidazol-1-yl)-N-[3-(trifluoromethyl)phenyl]acetamide,
N-(2,3-Dihydro-1H-inden-5-yl)-2-(7-methyl-1H-benzimidazol-1-yl)acetamide,
Methyl 1-{2-[(3,4-dimethylphenyl)amino]-2-oxoethyl}-1H-benzimidazole-7-carboxylate,
Methyl 1-[2-(2,3-dihydro-1H-inden-5-ylamino)-2-oxoethyl]-1H-benzimidazole-7-carboxylate,
Methyl 1-{2-[(4-tert-butylbenzyl)amino]-2-oxoethyl}-1H-benzimidazole-7-carboxylate,
Methyl 1-(2-{[3-methoxy-5 -(trifluoromethyl)phenyl]amino}-2-oxoethyl)-1H-benzimidazole-7-carboxylate,
Methyl 1-{2-[(3,5-dimethoxyphenyl)amino]-2-oxoethyl}-1H-benzimidazole-7-carboxylate,
N-(3,5-Dimethoxyphenyl)-2-{7-[(dimethylamino)sulfonyl]-1H-benzimidazol-1-yl}acetamide,
2-{7-[(Dimethylamino)sulfonyl]-1H-benzimidazol-1-yl}-N-[3-(trifluoromethyl)phenyl]acetamide,
N-(3,5-Dimethoxyphenyl)-2-[7-(propylsulfonyl)-1H-benzimidazol-1-yl]acetamide,
2-[7-(Propylsulfonyl)-1H-benzimidazol-1-yl]-N-[3-(trifluoromethyl)phenyl]acetamide, N-[3-Methoxy-5-(trifluoromethyl)phenyl]-2-[7-(methylsulfonyl)-1H-benzimidazol-1-yl]acetamide,
N-(3,5-Dimethoxyphenyl)-2-[7-(trifluoromethyl)-1H-benzimidazol-1-yl]acetamide,
N-(3,4-Dimethylphenyl)-2-[7-(trifluoromethyl)-1H-benzimidazol-1-yl]acetamide,
N-(4-tert-Butylbenzyl)-2-[7-(trifluoromethyl)-1H-benzimidazol-1-yl]acetamide,
N-(2,3-Dihydro-1H-inden-5-yl)-2-[7-(trifluoromethyl)-1H-benzimidazol-1-yl]acetamide,
2-(7-Cyano-1H-benzimidazol-1-yl)-N-(3,5-dimethoxyphenyl)acetamide,
2-(7-Cyano-1H-benzimidazol-1-yl)-N-(3-methoxyphenyl)acetamide,
2-(7-Cyano-1H-benzimidazol-1-yl)-N-[3-(trifluoromethyl)phenyl]acetamide,
2-(7-Cyano-1H-benzimidazol-1-yl)-N-(2,3-dihydro-1H-inden-5-yl)acetamide,
N-(2,3-Dihydro-1H-inden-5-yl)-2-(7-fluoro-1H-benzimidazol-1-yl)acetamide,
N-(3,5-Dimethoxyphenyl)-2-(7-fluoro-1H-benzimidazol-1-yl)acetamide,
N-(4-tert-Butylbenzyl)-2-(7-fluoro-1H-benzimidazol-1-yl)acetamide,
2-(7-Amino-1H-benzoimidazol-1-yl)-N-[3-(trifluoromethyl)phenyl]acetamide,
2-[7-(Acetylamino)-1H-benzoimidazol-1-yl]-N-[3-(trifluoromethyl)phenyl]acetamide,
2-{7-[(Methylsulfonyl)amino]-1H-benzoimidazol-1-yl}-N-[3-(trifluoromethyl)phenyl]acetamide, 2-[7-(Dimethylamino)-1H-benzoimidazol-1-yl]-N-[3-(trifluoromethyl)phenyl]acetamide,
2-[7-(Isopropylamino)-1H-benzoimidazol-1-yl]-N-[3-(trifluoromethyl)phenyl]acetamide,
N-(3,5-Dimethoxyphenyl)-2-[7-(1H-tetrazol-5-yl)-1H-benzimidazol-1-yl]acetamide, and
2-(6,7-Difluoro-1H-benzimidazol-1-yl)-N-[3-(trifluoromethyl)phenyl]acetamide, or a pharmaceutically acceptable salt thereof.

9. A pharmaceutical composition comprising as active ingredient a therapeutically effective amount of the compound according to claim 1, in association with one or more pharmaceutically acceptable diluents, excipients and/or inert carriers.

* * * * *